US011155641B2

(12) United States Patent
Kim et al.

(10) Patent No.: US 11,155,641 B2
(45) Date of Patent: Oct. 26, 2021

(54) CYTOSOL-PENETRATING ANTIBODY AND USE THEREOF

(71) Applicant: ORUM THERAPEUTICS INC., Daejeon (KR)

(72) Inventors: Yong Sung Kim, Gyeonggi-do (KR); Ji Sun Kim, Gyeonggi-do (KR); Jae Yeong Park, Gyeonggi-do (KR)

(73) Assignee: ORUM THERAPEUTICS INC., Daejeon (KR)

(*) Notice: Subject to any disclaimer, the term of this patent is extended or adjusted under 35 U.S.C. 154(b) by 0 days.

(21) Appl. No.: 16/304,444

(22) PCT Filed: May 26, 2017

(86) PCT No.: PCT/KR2017/005559
§ 371 (c)(1),
(2) Date: Nov. 26, 2018

(87) PCT Pub. No.: WO2017/204606
PCT Pub. Date: Nov. 30, 2017

(65) Prior Publication Data
US 2019/0144566 A1    May 16, 2019

(30) Foreign Application Priority Data

May 27, 2016  (KR) .................. 10-2016-0065365
May 27, 2016  (KR) .................. 10-2016-0065379
May 26, 2017  (KR) .................. 10-2017-0065670

(51) Int. Cl.
*C07K 16/46* (2006.01)
*C07K 16/00* (2006.01)
*C07K 16/30* (2006.01)
*C07K 16/32* (2006.01)
*C07K 16/18* (2006.01)
*A61K 39/00* (2006.01)

(52) U.S. Cl.
CPC ............ *C07K 16/464* (2013.01); *C07K 16/00* (2013.01); *C07K 16/18* (2013.01); *C07K 16/30* (2013.01); *C07K 16/32* (2013.01); *A61K 2039/505* (2013.01); *C07K 2317/24* (2013.01); *C07K 2317/515* (2013.01); *C07K 2317/522* (2013.01); *C07K 2317/524* (2013.01); *C07K 2317/526* (2013.01); *C07K 2317/56* (2013.01); *C07K 2317/565* (2013.01); *C07K 2317/77* (2013.01); *C07K 2317/82* (2013.01); *C07K 2317/94* (2013.01)

(58) Field of Classification Search
CPC ...... C07K 16/464; C07K 16/32; C07K 16/18; C07K 16/00; C07K 16/30; C07K 2317/82; C07K 2317/56; C07K 2317/515; C07K 2317/24; C07K 2317/522; C07K 2317/524; C07K 2317/526; C07K 2317/565; C07K 2317/77; C07K 2317/94; A61K 2039/505
See application file for complete search history.

(56) References Cited

U.S. PATENT DOCUMENTS

| | | | |
|---|---|---|---|
| 9,815,866 B2 | 11/2017 | Shiba et al. | |
| 10,787,487 B2 | 9/2020 | Kim et al. | |
| 10,844,136 B2 | 11/2020 | Kim et al. | |
| 10,851,177 B2 | 12/2020 | Kim et al. | |
| 2005/0288492 A1 | 12/2005 | Rabbitts et al. | |
| 2011/0189206 A1 | 8/2011 | Barbas | |
| 2011/0263829 A1 | 10/2011 | Kim et al. | |
| 2013/0266570 A1 | 10/2013 | Weisbart et al. | |
| 2014/0179543 A1 | 6/2014 | Rabbitts et al. | |
| 2015/0246945 A1 | 9/2015 | Shiba et al. | |
| 2016/0229892 A1 | 8/2016 | Hazlehurst et al. | |
| 2017/0158777 A1* | 6/2017 | Kim ................. | C07K 16/44 |
| 2017/0218084 A1* | 8/2017 | Kim ................. | C07K 16/32 |
| 2019/0231872 A1 | 8/2019 | Kwon et al. | |
| 2019/0389910 A1 | 12/2019 | Kim et al. | |
| 2020/0385428 A1 | 12/2020 | Kim et al. | |

FOREIGN PATENT DOCUMENTS

| | | |
|---|---|---|
| CN | 1241574 A | 1/2000 |
| CN | 101402675 A | 4/2009 |
| CN | 102209726 A | 10/2011 |
| CN | 103874710 A | 6/2014 |
| JP | H 8-511162 A | 11/1996 |
| JP | 2006521088 A | 9/2006 |
| JP | 2006523086 A | 10/2006 |

(Continued)

OTHER PUBLICATIONS

Paul et al, Fundamental Immunology, (textbook), pp. 292-295 (Year: 1993).*
Rudikoff et all., Proc. Natl. Acad. Sci. USA vol. 79 p. 1979 (Year: 1982).*
Kussie et al., J. Immunol. 152: 146-152 (Year: 1994).*
Wu et al., J. Mol. Biol. 294: 151-162 (Year: 1999).*
Kim et al., J Controlled Release 235: 165-175 (Year: 2016).*
Choi et al., MAbs 6(6): 1402-1414 (Year: 2014).*
Al-Lazikani et al., 1997, "Standard conformations for the canonical structures of immunoglobulins," J Mol Biol, 273(4):927-948.
Altmann et al., 2017, "Identification of a Novel ITGαvβ6-Binding Peptide Using Protein Separation and Phage Display," Clin Cancer Res., 23(15):4170-4180.

(Continued)

*Primary Examiner* — Phuong Huynh
(74) *Attorney, Agent, or Firm* — Jones Day

(57) ABSTRACT

The present disclosure relates to a cytosol-penetrating antibody and the use thereof, and more specifically to identification of a structural mechanism that induces escape from endosomes into the cytosol after cellular internalization into living cells through a cell membrane protein, a light-chain variable region and/or heavy-chain variable region, which is based on this identification and has a significantly improved ability to escape from endosomes into the cytosol, a cytosol-penetrating antibody comprising the same, a method for producing the same, and the use thereof.

27 Claims, 34 Drawing Sheets
(31 of 34 Drawing Sheet(s) Filed in Color)
Specification includes a Sequence Listing.

(56) References Cited

FOREIGN PATENT DOCUMENTS

| | | |
|---|---|---|
| JP | 2011519370 A | 7/2011 |
| KR | 10-2009-0008290 A | 1/2009 |
| KR | 10-2010-0045683 A | 5/2010 |
| KR | 1020100053466 A | 5/2010 |
| KR | 1020160011598 A | 2/2016 |
| KR | 10-1790669 B1 | 10/2017 |
| KR | 10-2019-0056340 A | 5/2019 |
| WO | WO 2003077945 A1 | 9/2003 |
| WO | WO 2004046186 A2 | 6/2004 |
| WO | WO 2004046186 A3 | 6/2004 |
| WO | WO 2004046188 A2 | 6/2004 |
| WO | WO 2004046188 A3 | 6/2004 |
| WO | WO 2007133835 A2 | 11/2007 |
| WO | WO 2007133835 A3 | 11/2007 |
| WO | WO 2009134025 A2 | 11/2009 |
| WO | WO 2009134025 A3 | 11/2009 |
| WO | WO 2009134027 A2 | 11/2009 |
| WO | WO 2009134027 A3 | 11/2009 |
| WO | WO 2010056043 A2 | 5/2010 |
| WO | WO 2010056043 A3 | 5/2010 |
| WO | WO 2010056043 A9 | 5/2010 |
| WO | WO 2011026641 A1 | 3/2011 |
| WO | WO 2011026641 A9 | 3/2011 |
| WO | WO 2011140151 A1 | 11/2011 |
| WO | WO 2012135831 A1 | 10/2012 |
| WO | WO 2014042209 A1 | 3/2014 |
| WO | WO 2016013870 A1 | 1/2016 |
| WO | WO 2016013871 A1 | 1/2016 |
| WO | WO 2016161390 A1 | 10/2016 |

OTHER PUBLICATIONS

Avrameas et al., 1998, "Polyreactive anti-DNA monoclonal antibodies and a derived peptide as vectors for the intracytoplasmic and intranuclear translocation of macromolecules," Proc Natl Acad Sci USA, 95(10):5601-5606.

Baek et al., 2014, "Construction of a large synthetic human Fab antibody library on yeast cell surface by optimized yeast mating," J Microbiol Biotechnol., 24(3):408-420.

Baek et al., 2014, "DNA Assembly Tools and Strategies for the Generation of Plasmids," Microbiol Spectr, 2(5), pp. 1-12.

Baek et al., 2015, "Humanization of a phosphothreonine peptide-specific chicken antibody by combinatorial library optimization of the phosphoepitope-binding motif," Biochem Biophys Res Commun., 463(3):414-420.

Barbas et al., 2007, "Quantitation of DNA and RNA," Cold Spring Harb. Protoc., retreived from internet: http://cshprotocols.cshlp.org/content/2007/11/pdb.ip47.long on Nov. 1, 2019 (2 pages).

Barrette-Ng et al., 2013, "The structure of the SBP-Tag-streptavidin complex reveals a novel helical scaffold bridging binding pockets on separate subunits," Acta Crystallogr D Biol Crystallogr., 69(Pt 5):879-887.

Benatuil et al., 2010, "An improved yeast transformation method for the generation of very large human antibody libraries," Protein Eng Des Sel., 23(4):155-159.

Blundell et al., 2006, "Structural biology and bioinformatics in drug design: opportunities and challenges for target identification and lead discovery," Philos Trans R Soc Lond B Biol Sci., 361(1467):413-423.

Caldas et al., 2003, "Humanization of the anti-CD18 antibody 6.7: an unexpected effect of a framework residue in binding to antigen," Mol Immunol., 39(15):941-952.

Cao et al., 2008, "Enhancement of antitumor properties of TRAIL by targeted delivery to the tumor neovasculature," Mol Cancer Ther., 7(4):851-861.

Casset et al., 2003, "A peptide mimetic of an anti-CD4 monoclonal antibody by rational design," Biochem Biophys Res Commun., 307(1):198-205.

Chang et al., 2014, "Loop-sequence features and stability determinants in antibody variable domains by high-throughput experiments," Structure, 22(1):9-21.

Chauhan et al., 2007, "The taming of the cell penetrating domain of the HIV Tat: myths and realities," J Control Release, 117(2):148-162.

Chen et al., 1995, "Enhancement and destruction of antibody function by somatic mutation: unequal occurrence is controlled by V gene combinatorial associations," EMBO J., 14(12):2784-2794.

Chien et al., 1989, "Significant structural and functional change of an antigen-binding site by a distant amino acid substitution: proposal of a structural mechanism," Proc Natl Acad Sci USA, 86(14):5532-5536.

Colman, 1994, "Effects of amino acid sequence changes on antibody-antigen interactions," Res Immunol., 145(1):33-36.

De Pascalis et al., 2002, "Grafting of "abbreviated" complementarity-determining regions containing specificity-determining residues essential for ligand contact to engineer a less immunogenic humanized monoclonal antibody," J Immunol., 169(6):3076-3084.

Di Paolo et al., 2003, "A recombinant immunotoxin derived from a humanized epithelial cell adhesion molecule-specific single-chain antibody fragment has potent and selective antitumor activity," Clin Cancer Res, 9(7):2837-2848.

Dohi et al., 2001, "Elimination of colonic patches with lymphotoxin receptor-Ig prevents Th2 cell-type colitis," The Journal of Immunology, 167(5):2781-2790.

Edman, 1959, "Chemistry of amino acids and peptides," Annu Rev Biochem, 28:69-96.

Ehrenstein et al., 1995, "Human IgG anti-DNA antibodies deposit in kidneys and induce proteinuria in SCID mice," Kidney Int., 48(3):705-711.

Ewert et al., 2004, "Stability improvement of antibodies for extracellular and intracellular applications: CDR grafting to stable frameworks and structure-based framework engineering," Methods, 34(2):184-199.

Extended European Search Report and Written Opinion of European Patent Application No. 15825418.5 dated Jan. 4, 2018 (8 pages).

Falnes et al., 2001, "Ability of the Tat basic domain and VP22 to mediate cell binding, but not membrane translocation of the diphtheria toxin A-fragment," Biochemistry, 40(14):4349-4358.

Fernandes et al., 2016, "Context-dependent roles for lymphotoxin-β receptor signaling in cancer development," Biochim Biophys Acta., 1865(2):204-219.

Garrigues et al., 1993, "Ley specific antibody with potent anti-tumor activity is internalized and degraded in lysosomes," Am J Pathol., 142(2):607-622.

Gerber et al., 2013, "The antibody-drug conjugate: an enabling modality for natural product-based cancer therapeutics," Nat Prod Rep., 30(5):625-639.

Giusti et al., 1987, "Somatic diversification of S107 from an antiphosphocholine to an anti-DNA autoantibody is due to a single base change in its heavy chain variable region," Proc Natl Acad Sci USA, 84(9):2926-2930.

Gouttefangeas et al., 2014, "Flow Cytometry in Cancer Immunotherapy: Applications, Quality Assurance, and Future," N. Rezaei (ed.), Cancer Immunology: A Translational Medicine Context, Springer-Verlag Berlin Heidelberg, Chapter 25, pp. 471-490.

Guidotti et al., 2017, "Cell-Penetrating Peptides: From Basic Research to Clinics," Trends in Pharmacological Sciences, 38(4):406-424.

Guillard et al., 2015, "Engineering therapeutic proteins for cell entry: the natural approach," Trends in biotechnology, 33(3):163-171.

Gussow et al., 1991, "Humanization of monoclonal antibodies," Methods Enzymol., 203:99-121.

Holig et al., 2004, "Novel RGD lipopeptides for the targeting of liposomes to integrin-expressing endothelial and melanoma cells," Prot Eng Des Sel, 17(5):433-441.

Hollingshead, 2008, "Antitumor efficacy testing in rodents," J Natl Cancer Inst., 100(21):1500-1510.

Holm et al., 2007, "Functional mapping and single chain construction of the anti-cytokeratin 8 monoclonal antibody TS1," Mol Immunol., 44(6):1075-1084.

Horth et al., 1991, "Theoretical and functional analysis of the SIV fusion peptide," EMBO J., 10(10):2747-2755.

(56) References Cited

OTHER PUBLICATIONS

Horton et al., 2002, "Exploring privileged structures: the combinatorial synthesis of cyclic peptides," J Comput Aided Mol Des., 16(5-6):415-430.

Hu et al., 2013, "Comparison of the inhibition mechanisms of adalimumab and infliximab in treating tumor necrosis factor α-associated diseases from a molecular view," J Biol Chem., 288(38):27059-27067.

Imai et al., 2006, "Comparing antibody and small-molecule therapies for cancer," Nat Rev Cancer, 6(9):714-727.

International Search Report and Written Opinion dated Oct. 11, 2019 of International Patent Application No. PCT/IB2019/055193 (14 pages).

International Search Report and Written Opinion dated Oct. 7, 2015 of International Patent Application No. PCT/KR2015/007626 (published as WO 2016013870) (12 pages).

International Search Report and Written Opinion dated Sep. 29, 2017 of International Patent Application No. PCT/KR2017/005559 (published as WO 2017204606) (10 pages).

International Search Report and Written Opinion dated Sep. 30, 2015 of International Patent Application No. PCT/KR2015/007627 (published as WO 2016013871) (12 pages).

Jang et al., 2009, "A nucleic acid-hydrolyzing antibody penetrates into cells via caveolae-mediated endocytosis, localizes in the cytosol and exhibits cytotoxicity," Cell Mol Life Sci., 66(11-12):1985-1997.

Kabat et al., 1991, "Sequences of Proteins of Immunological Interest," vol. 1 (24 pages).

Kim et al., 2005, "Antibody engineering for the development of therapeutic antibodies," Mol Cells, 20(1):17-29.

Kim et al., 2006, "Heavy and light chain variable single domains of an anti-DNA binding antibody hydrolyze both double- and single-stranded DNAs without sequence specificity," J Biol Chem., 281(22):15287-15295.

Kim et al., 2012, "Interfering transbody-mediated Her2 gene silencing induces apoptosis by G0/G1 cell cycle arrest in Her2-overexpressing SK-BR-3 breast cancer cells," Biotechnology and Bioprocess Engineering, 17(2):413-419.

Kim et al., 2015, "Quantitative assessment of cellular uptake and cytosolic access of antibody in living cells by an enhanced split GFP complementation assay," Biochem Biophys Res Commun., 467(4):771-777.

Kim, 2014, "General Strategy for Generating Intact, full-lenght IgG antibodies that penetrate into the cytosol of living cells," KSBB, IP306, Oct. 5, 2014, XP002776743, retreived from the internet: URL:www.ksbb.or.kr/board/download.php?code=notice&num=1913 &comm= [retrieved on Dec. 11, 2017].

Koivunen et al., 1995, "Phage libraries displaying cyclic peptides with different ring sizes: ligand specificities of the RGD-directed integrins," Biotechnology (NY), 13(3):265-270.

Kussie et al., 1994, "A single engineered amino acid substitution changes antibody fine specificity," J Immunol., 152(1):146-152.

Lee et al., 2010, "Gene silencing by cell-penetrating, sequence-selective and nucleic-acid hydrolyzing antibodies," Nucleic Acids Res., 38(5):1596-1609.

Lee et al., 2011, "Generation of bivalent and bispecific kringle single domains by loop grafting as potent agonists against death receptors 4 and 5," J Mol Biol., 411(1):201-219.

Lee et al., 2013, "Functional consequences of complementarity-determining region deactivation in a multifunctional anti-nucleic acid antibody," J Biol Chem., 288(50):35877-35885.

Leem et al., 2016, "ABodyBuilder: Automated antibody structure prediction with data-driven accuracy estimation," MAbs, 8(7):1259-1268.

Leshchiner et al., 2015, "Direct inhibition of oncogenic KRAS by hydrocarbon-stapled SOS1 helices," Proc Natl Acad Sci USA, 112(6):1761-1766.

MacCallum et al., 1996, "Antibody-antigen interactions: contact analysis and binding site topography," J Mol Biol., 262(5):732-745.

Madaio et al., 1996, "Spontaneously produced anti-DNA/DNase I autoantibodies modulate nuclear apoptosis in living cells," Eur J Immunol., 26(12):3035-3041.

Madgdelaine-Beuzelin et al., 2007, "Structure-function relationships of the variable domains of monoclonal antibodies approved for cancer treatment," Crit Rev Oncol Hematol., 64(3):210-225.

Manikandan et al., 2007, "Protein i: interference at protein level by intrabodies," Front Biosci., 12:1344-1352.

Marchisio et al., 1984, "Immunofluorescence localization of phosphotyrosine containing proteins in RSV-transformed mouse fibroblasts," Exp Cell Res., 154(1):112-124.

Mariuzza et al., 1987, "The structural basis of antigen-antibody recognition," Annu Rev Biophys Biophys Chem., 16:139-159.

Marschall et al., 2011, "Targeting antibodies to the cytoplasm," MAbs, 3(1):3-16.

Mauri et al., 1998, "LIGHT, a new member of the TNF superfamily, and lymphotoxin alpha are ligands," Immunity, 8(1):21-30.

Min et al., 2016, "Cell-free production and streamlined assay of cytosol-penetrating antibodies," Biotechnol Bioeng, 113(10):2107-2112.

Munz et al., 2009, "The emerging role of EpCAM in cancer and stem cell signaling," Cancer Res., 69(14):5627-5629.

Nakajima et al., 2004, "Method for delivering radiolabeled single-chain fv antibody to the brain," Journal of health science, 50(2):159-163.

Patel et al., 2007, "Cell penetrating peptides: intracellular pathways and pharmaceutical perspectives," Pharm Res., 24(11):1977-1992.

Patgiri et al., 2011, "An orthosteric inhibitor of the Ras-Sos interaction," Nat Chem Biol, 7(9):585-587.

Perrimon et al., 2000, "Specificities of heparan sulphate proteoglycans in developmental processes," Nature, 404(6779):725-728.

Pimenta et al., 2014, "Role of tertiary lymphoid structures (TLS) in antitumor immunity. Potential tumor-induced cytokines/chemokines that regulate TLS formation in epithelial-derived cancers," Cancer, 6(2):969-997.

Rezai et al., 2006, "Testing the conformational hypothesis of passive membrane permeability using synthetic cyclic peptide diastereomers," J Am Chem Soc., 128(8):2510-2511.

Rudikoff et al., 1982, "Single amino acid substitution altering antigen-binding specificity," Proc Natl Acad Sci USA, 79(6):1979-1983.

Sapra et al., 2002, "Internalizing antibodies are necessary for improved therapeutic efficacy of antibody-targeted liposomal drugs," Cancer Res., 62(24):7190-7194.

Scheffzek et al., 1997, "The Ras-RasGAP complex: structural basis for GTPase activation and its loss in oncogenic Ras mutants," Science, 277(5324):333-338.

Shin et al., 2017, "Antibody targeting intracellular oncogenic Ras mutants exerts anti-tumour effects after systemic administration," Nat Commun., 8:15090 (14 pages).

Simon et al., 2013, "Epithelial cell adhesion molecule-targeted drug delivery for cancer therapy, Expert opinion on drug delivery," Expert Opin Drug Deliv., 10(4):451-468.

Singh et al., 2016, "A New Triglycyl Peptide Linker for Antibody-Drug Conjugates (ADCs) with Improved Targeted Killing of Cancer Cells," Mol Cancer Ther., 15(6):1311-1320.

Stuible et al., 2014, "Mechanism and function of monoclonal antibodies targeting siglec-15 for therapeutic inhibition of osteoclastic bone resorption," J Biol Chem., 289(10):6498-6512.

Sudhamsu et al., 2013, "Dimerization of LTβR by LTα1β2 is necessary and sufficient for signal transduction," Proc Natl Acad Sci USA, 110(49):19896-19901.

Supplemental European Search Report and Written Opinion of European Patent Application No. 15825508.3 dated dated Feb. 8, 2018 (10 pages).

Tanaka et al., 2003, "Intrabodies based on intracellular capture frameworks that bind the RAS protein with high affinity and impair oncogenic transformation," EMBO J., 22(5):1025-1035.

Tanaka et al., 2003, "Single domain intracellular antibodies: a minimal fragment for direct in vivo selection of antigen-specific intrabodies," J Mol Biol., 331(5):1109-1120.

(56) References Cited

OTHER PUBLICATIONS

Tanaka et al., 2007, "Tumour prevention by a single antibody domain targeting the interaction of signal transduction proteins with RAS," EMBO J., 26(13):3250-3259.
Teicher, 2009, "In vivo/ex vivo and in situ assays used in cancer research: a brief review," Toxicol Pathol, 37(1):114-122.
Vajdos et al., 2002, "Comprehensive functional maps of the antigen-binding site of an anti-ErbB2 antibody obtained with shotgun scanning mutagenesis," J Mol Biol., 320(2):415-428.
Vargas-Madrazo et al., 2003, "An improved model of association for VH-VL immunoglobulin domains: asymmetries between VH and VL in the packing of some interface residues," J Mol Recognit, 16(3):113-120.
Wang et al., 2001, "The regulation of T cell homeostasis and autoimmunity by T cell-derived Light," J Clin Invest, 108(12):1771-1780.
Weinstein, 2015, "Lymphotoxin Therapeutic Lymphoid Organogenesis in the Tumor Microenvironment," Adv Cancer Res., 128:197-233.
Weisbart et al., 2012, "A cell-penetrating bispecific antibody for therapeutic regulation of intracellular targets," Mol Cancer Ther., 11(10):2169-2173.
Went et al., 2006, "Frequent high-level expression of the immunotherapeutic target Ep-CAM in colon, stomach, prostate and lung cancers," Br J Cancer, 94(1):128-135.
Winkler et al., 2000, "Changing the antigen binding specificity by single point mutations of an anti-p24 (HIV-1) antibody," J Immunol., 165(8):4505-4514.
Wu et al., 1999, "Humanization of a murine monoclonal antibody by simultaneous optimization of framework and CDR residues," J Mol Biol., 294(1):151-162.
Xiong et al., 2002, "Crystal structure of the extracellular segment of integrin alpha Vbeta3 in complex with an Arg-Gly-Asp ligand," Science, 296(5565):151-155.
Yamaguchi et al., 2014, "Development of a sensitive screening method for selecting monoclonal antibodies to be internalized by cells," Biochem Biophys Res Commun., 454(4):600-603.
Yu et al., 2012, "Rationalization and design of the complementarity determining region sequences in an antibody-antigen recognition interface," PLoS One, 7(3):e33340 (15 pages).
Zack et al., 1996, "Mechanisms of cellular penetration and nuclear localization of an anti-double strand DNA autoantibody," J Immunol., 157(5):2082-2088.
Williams et al., 2018, "Peptide ligands for targeting the extracellular domain of EGFR: Comparison between linear and cyclic peptides," Chem Biol Drug Des., 91(2):605-619.
Bissig, C., et al., "Lipid Sorting and Multivesicular Endosome Biogenesis", "Cold Spring Harbor Perspectives in Biology", 2013, pp. 1-19, vol. 5, No. 5;a016816.
Bonvin, P., et al., "De Novo Isolation of Antibodies With pH-Dependent Binding Properties", "mAbs", 2015, pp. 294-302, vol. 7, No. 2.
Cabantous, S., et al., "Protein Tagging and Detection with Engineered Self-Assembling Fragments of Green Fluorescent Protein", "Nature Biotechnology", Jan. 2005, pp. 102-107, vol. 23, No. 1.
Choi, D., et al., "A General Strategy for Generating Intact, Full-Length IgG Antibodies that Penetrate into the Cytosol of Living Cells", "mAbs", 2014, pp. 1402-1414, vol. 6, No. 6.
Cross, K., et al., "Mechanisms of Cell Entry by Influenza Virus", "Expert Review in Molecular Medicine", Aug. 2001, pp. 1-17.
Devanaboyina, S., et al., "The Effect of pH Dependence of Antibody-Antigen Interactions on Subcellular Trafficking Dynamics", "mAbs", 2013, pp. 851-859, vol. 5, No. 6.

Di Russo, N., et al., "pH-Dependent Conformational Changes in Proteins and Their Effect on Experimental pKaS: The Case of Nitrophorin 4", "PLOS Computational Biology", Nov. 2012, pp. 19, vol. 8, No. 11; e1002761.
Du, Z., et al., "pKa Coupling at the Intein Active Site: Implications for the Coordination Mechanism of Protein Splicing with a Conserved Aspartate", "J. Am. Chem. Soc.", Jul. 6, 2011, pp. 10275-10282, vol. 133, No. 26.
Dudgeon, K., et al., "General Strategy for the Generation of Human Antibody Variable Domains With Increased Aggregation Resistance", "PNAS Early Edition", 2012, pp. 10879-10884.
Gingis-Velitski, S., et al., "Heparanase Uptake is Mediated by Cell Membrane Heparan Sulfate Proteoglycans", "The Journal of Biological Chemistry", 2004, pp. 44084-44092, vol. 279, No. 42.
Guglielmi, L., et al., "Selection for Intrabody Solubility in Mammalian Cells Using GFP Fusions", "Protein Engineering, Design and Selection", 2011, pp. 873-881, vol. 24, No. 12.
Herce, H., et al., "Arginine-Rich Peptides Destabilize the Plasma Membrane, Consistent with a Pore Formation Translocation Mechanism of . . . ", "Biophysical Journal", Oct. 2009, pp. 1917-1925, vol. 97.
Jenssen, H., et al., "Peptide Antimicrobial Agents", "Clinical Microbiology Reviews", Jul. 2006, pp. 491-511, vol. 19, No. 3.
Kamide, K., et al., "Isolation of Novel Cell-Penetrating Peptides From a Random Peptide Library Using In Vitro Virus and Their Modifications", "International Journal of Molecular Medicine", 2010, pp. 41-51, vol. 25.
Kim, J., et al., "Endosomal Acidic pH-Induced Conformational Changes of a Cytosol-Penetrating Antibody Mediate Endosomal Escape", "Journal of Controlled Release", 2016, pp. 165-175, vol. 235.
Korte, T., et al., "pH-Dependent Hydrophobicity Profile of Hemagglutinin of Influenza Virus and its Possible Relevance in Virus Fusion", "Bioscience Reports", 1992, pp. 397-406, vol. 12, No. 5.
Li, S., et al., "pH-Controlled Two-Step Uncoating of Influenza Virus", "Biophysical Journal", Apr. 2014, pp. 1447-1456, vol. 106.
Lin, C., et al., "Effect of Chemical Functionalities in Poly(Amido Amine)s for Non-Viral Gene Transfection", "Journal of Controlled Release", 2008, pp. 267-272, vol. 132.
Lonn, P., et al., "Enhancing Endosomal Escape for Intracellular Delivery of Macromolecular Biologic Therapeutics", "Scientific Reports", 2016, pp. 1-9, vol. 6, No. 32301.
Morita, M., et al., "Lipid Recognition Propensities of Amino Acids in Membrane Proteins From Atomic Resolution Data", "BMC Biophysics", 2011, pp. 112, vol. 4, No. 21.
Munyendo, W., et al., "Cell Penetrating Peptides in the Delivery of Biopharmaceuticals", "Biomolecules", 2012, pp. 187-202, vol. 2.
Perchiacca, J., et al., "Mutational Analysis of Domain Antibodies Reveals Aggregation Hotspots Within and Near the Complementary Determining Regions", "Proteins", 2011, pp. 2637-2647.
Qin, B., et al., "Structural Basis of the Tanford Transition of Bovine Beta-Lactoglobulin", "Biochemistry", 1998, pp. 14014-14023, vol. 37.
Quadir, M., et al., "PEG—Polypeptide Block Copolymers as pH-Responsive Endosome-Solubilizing Drug Nanocarriers", "Molecular Pharmaceutics", 2014, pp. A-K.
NCBI, "Chain H, Heavy Chain of Fab Fragment Variable Region of Antibody D5", "NCBI database", Feb. 10, 2016.
Claro et al., 2017, "Chapter 4—Design and applications of cyclic peptides" in Peptide Applications in Biomedicine, Biotechnology and Bioengineering, Woodhead Publishing Series in Biomaterials, Nov. 27, 2017, pp. 87-129.
Kim et al., 2009, "Generation of Humanized anti-DNA Hydrolyzing Catalytic Antibodies by Complementarity Determining Region Grafting," Biochem Biophys Res Commun., 379(2):314-318 (Epub 2008).

* cited by examiner

[Figure 1]
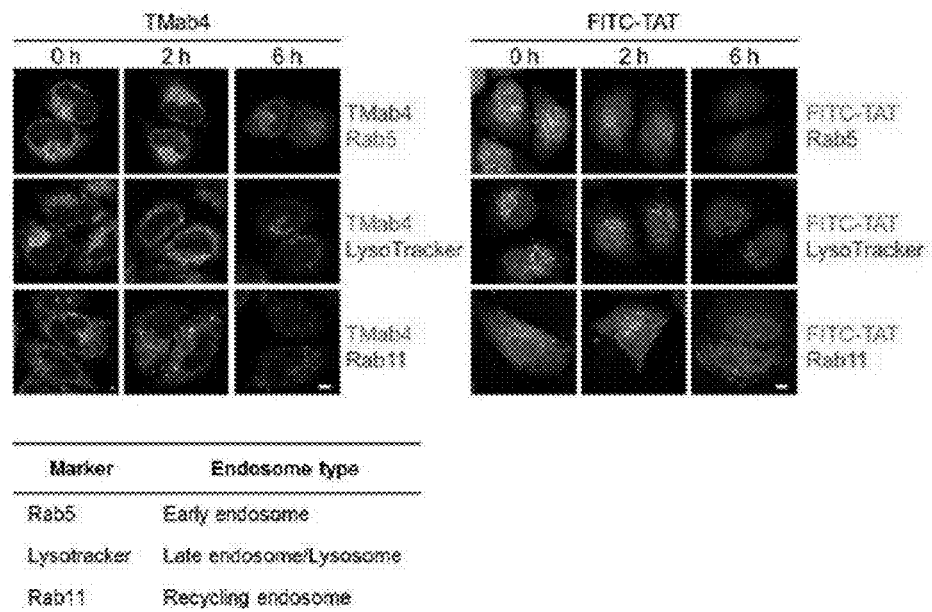
[Figure 2a]
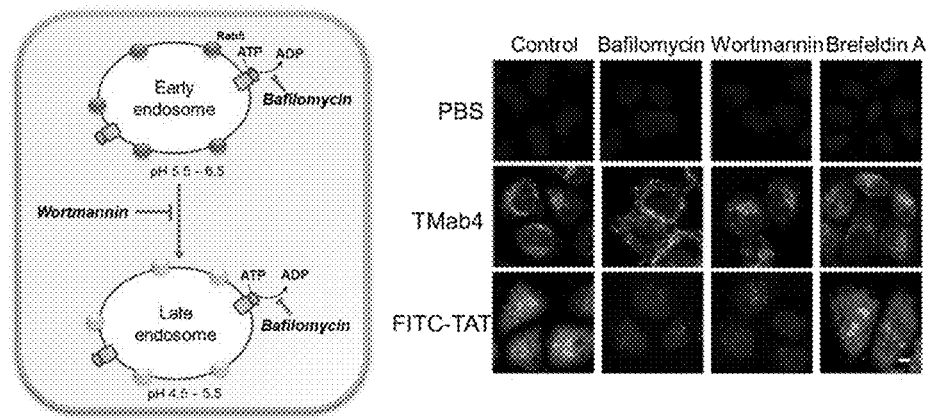

[Figure 2b]
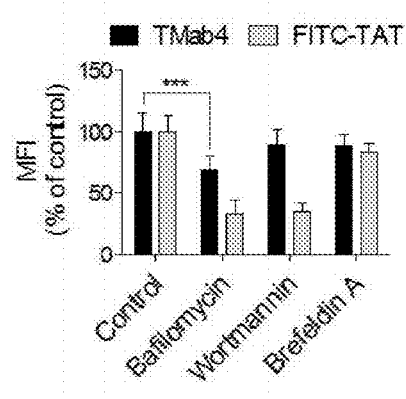
[Figure 2c]
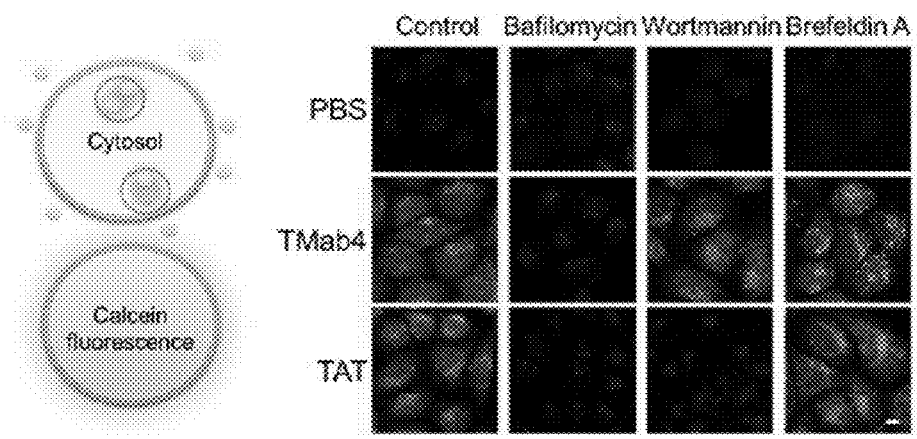

[Figure 2d]
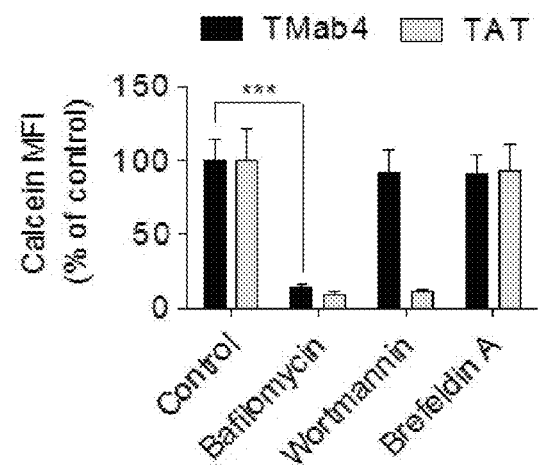
[Figure 3a]
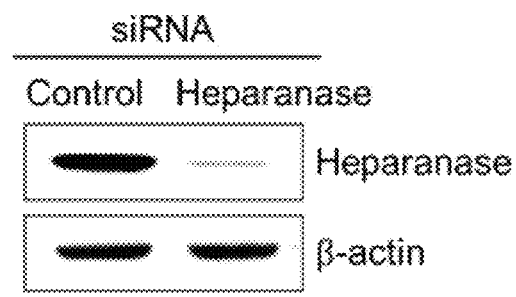

[Figure 3b]
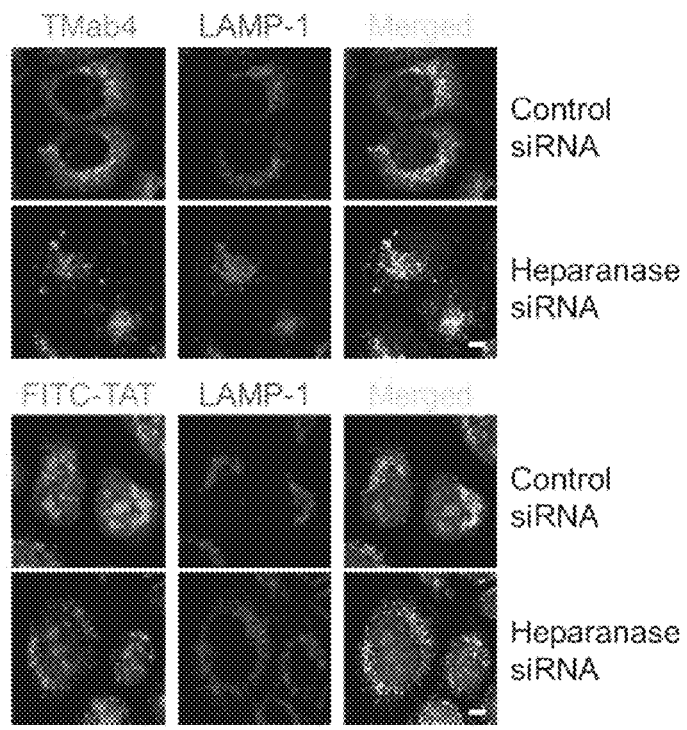
[Figure 3c]
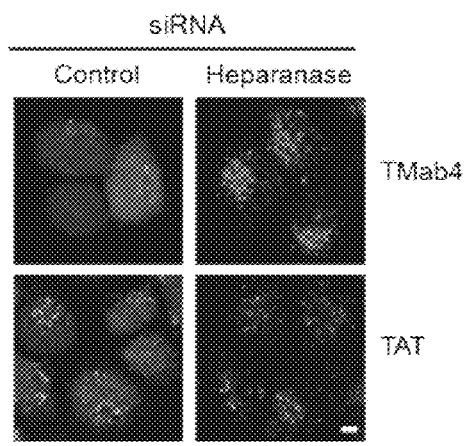

[Figure 4]
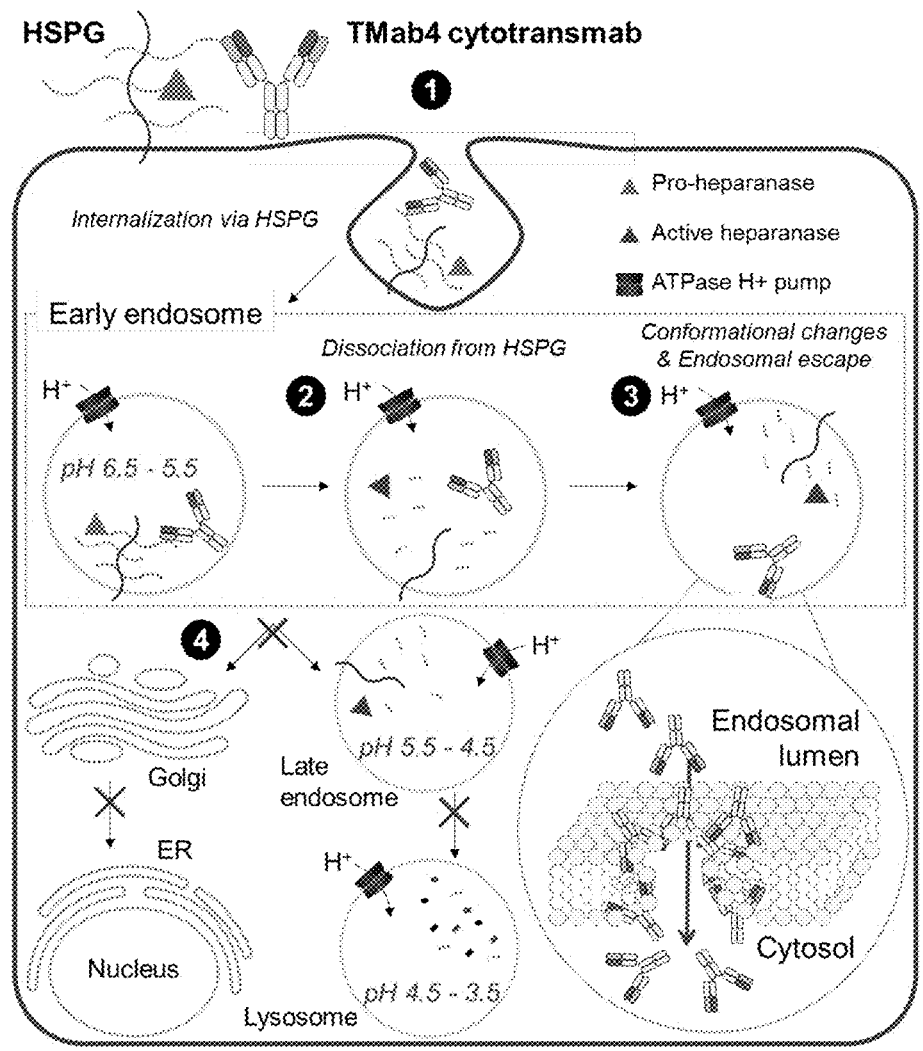

[Figure 5]
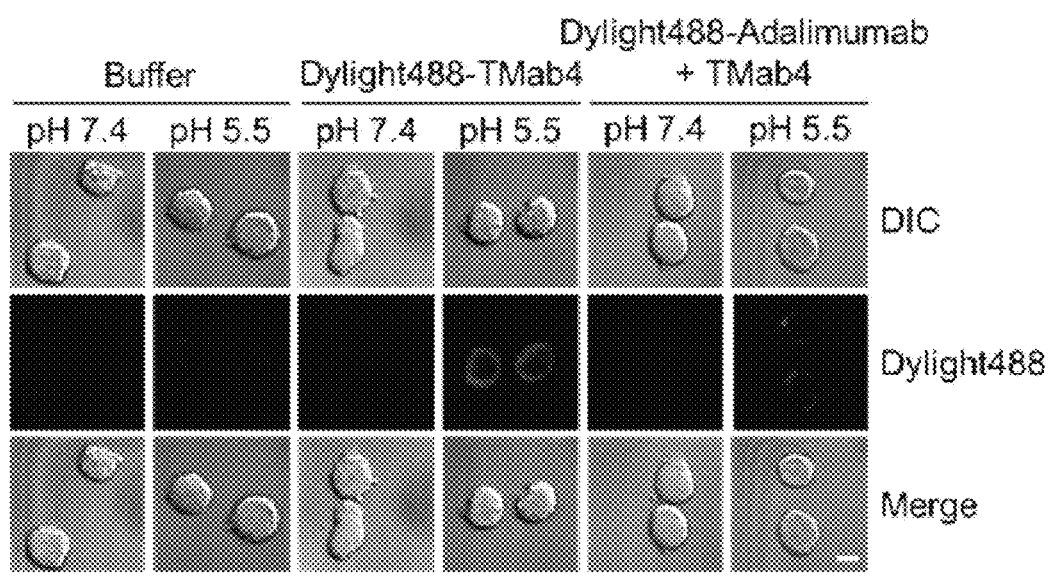
[Figure 6a]
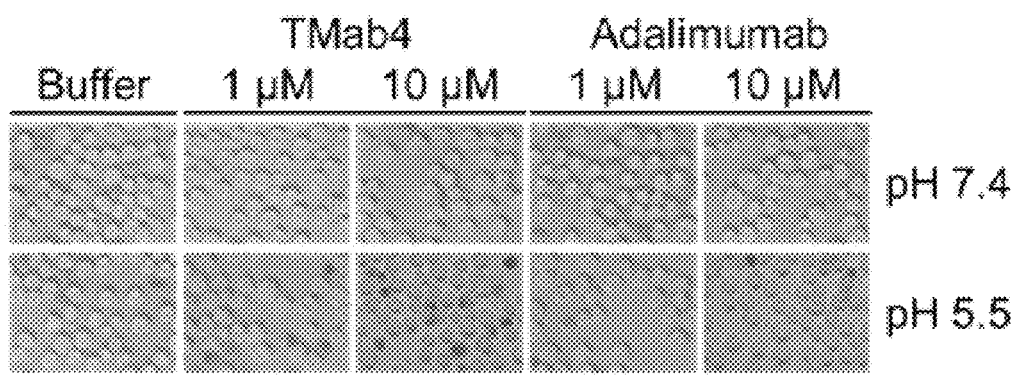

[Figure 6b]
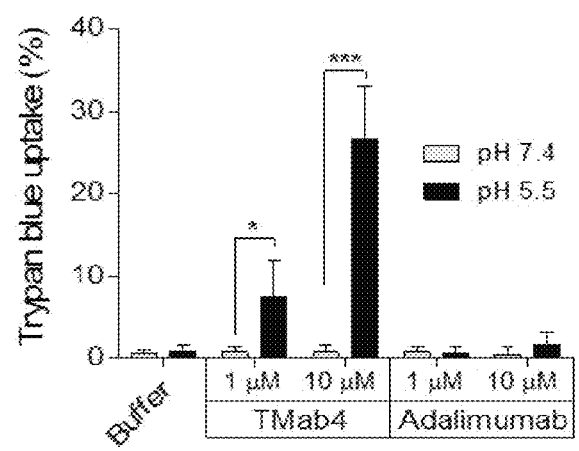
[Figure 7a]
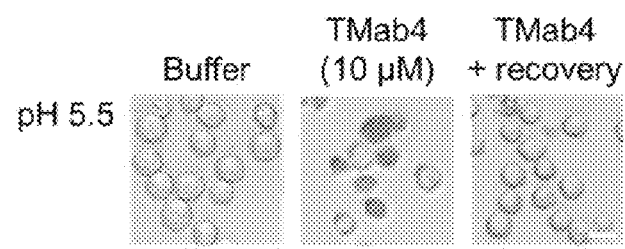

[Figure 7b]
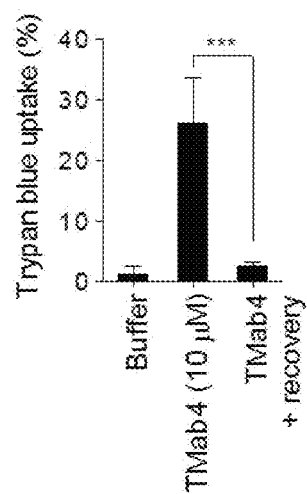
[Figure 8]
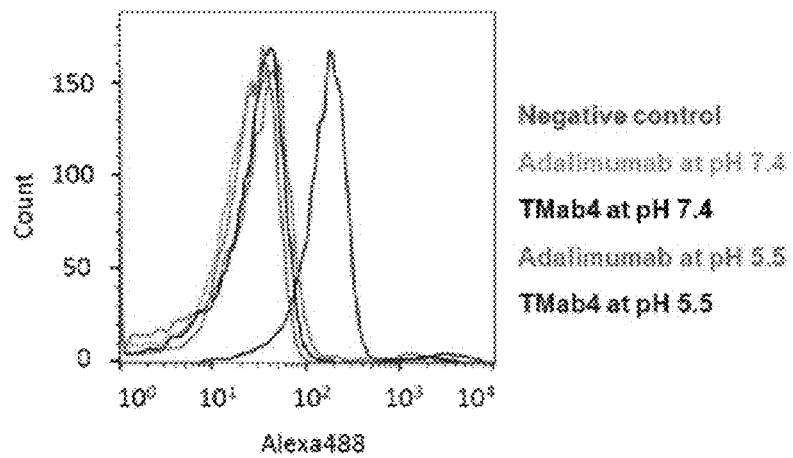

[Figure 9]
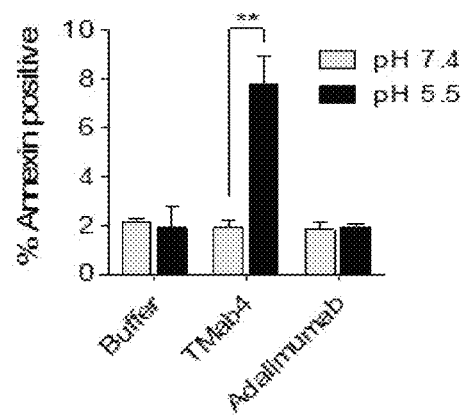
[Figure 10]
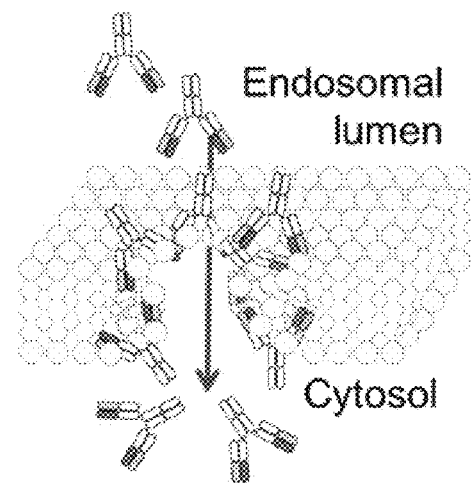

[Figure 11]
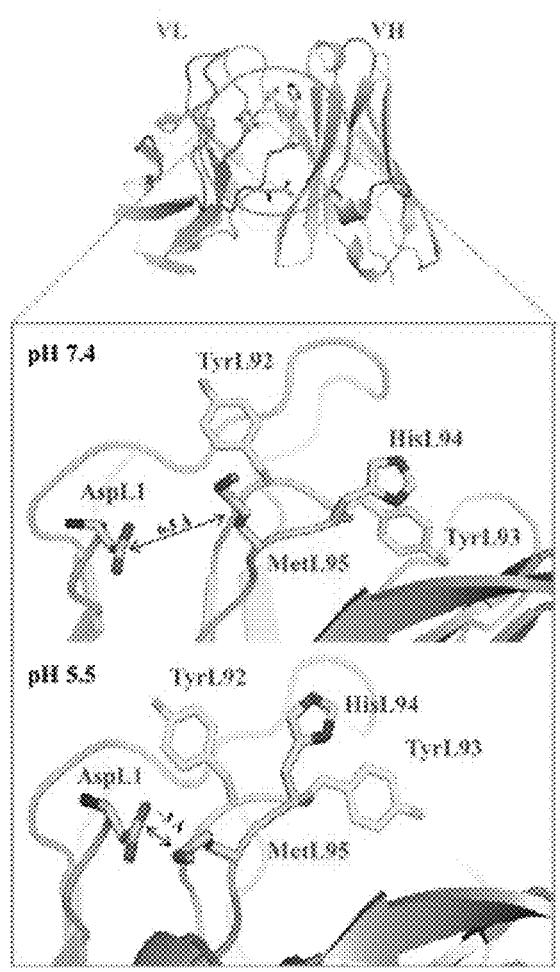

[Figure 12]
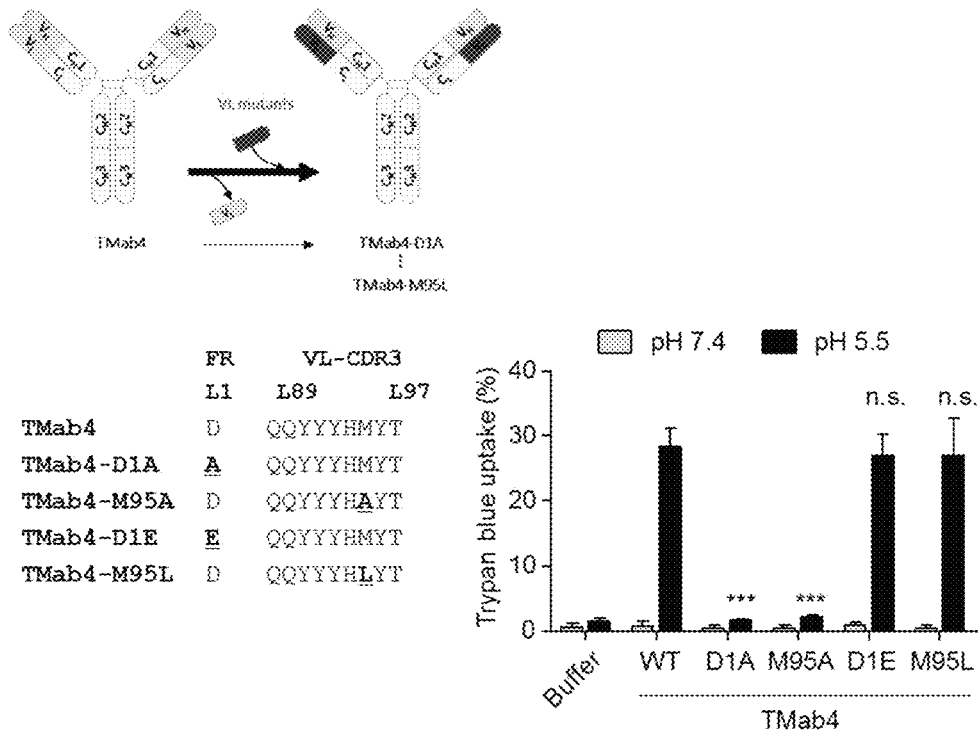
[Figure 13]
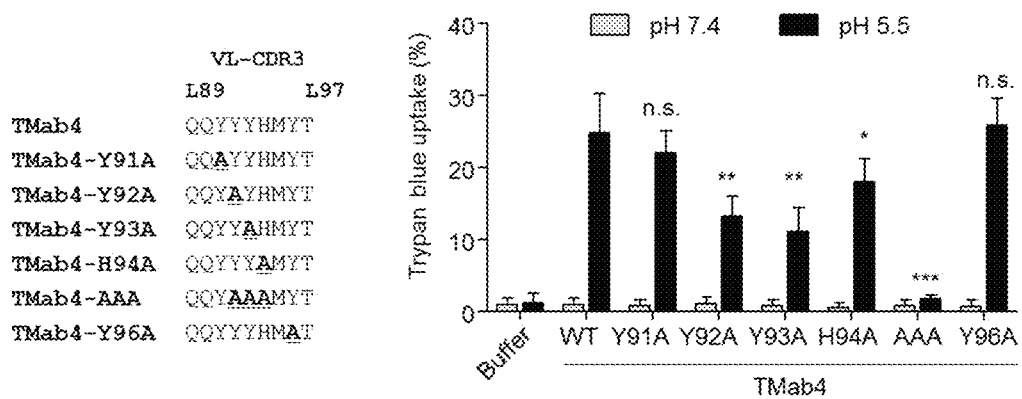

[Figure 14a]
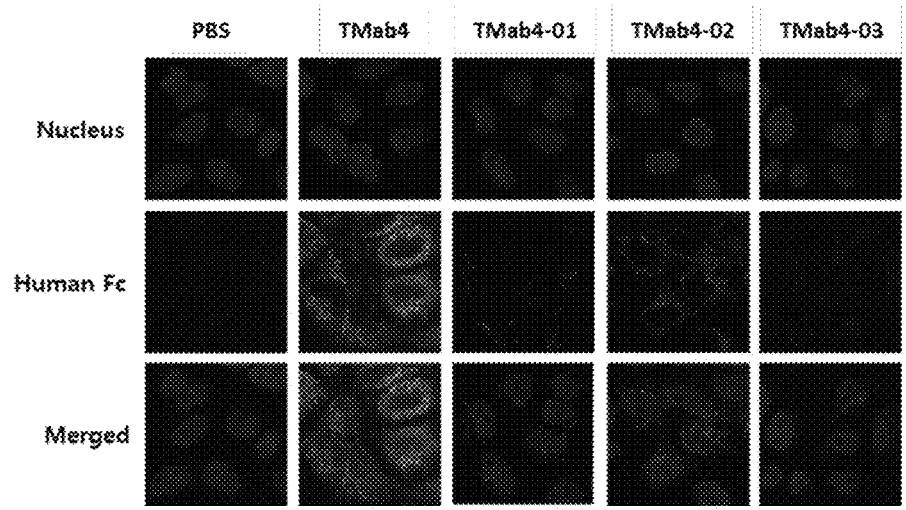
[Figure 14b]
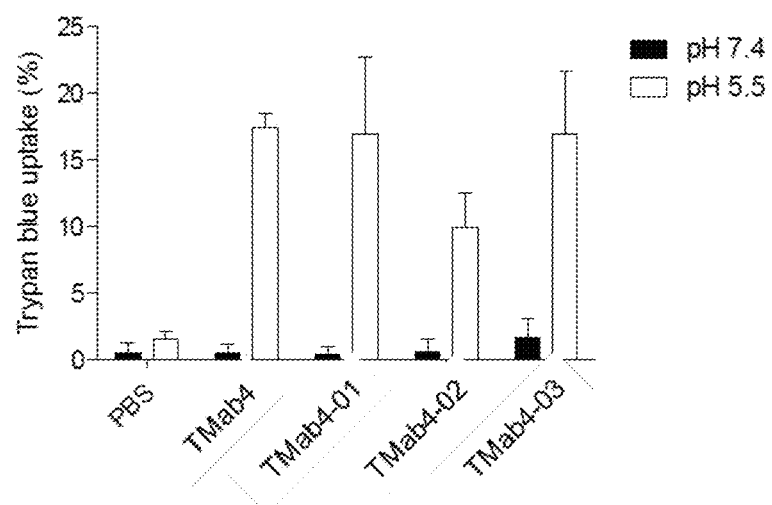

[Figure 15a]
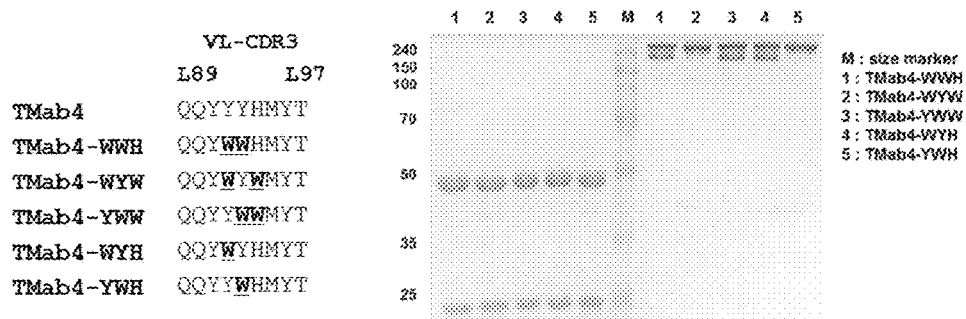
[Figure 15b]
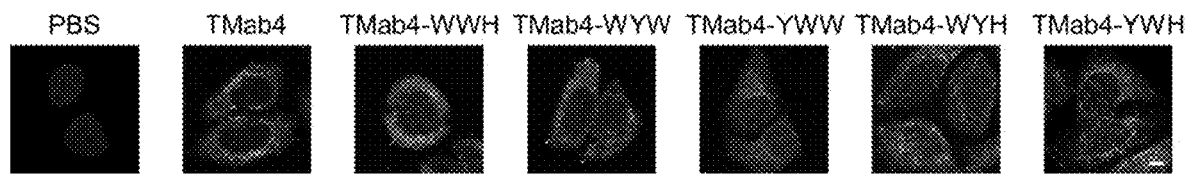
[Figure 16]
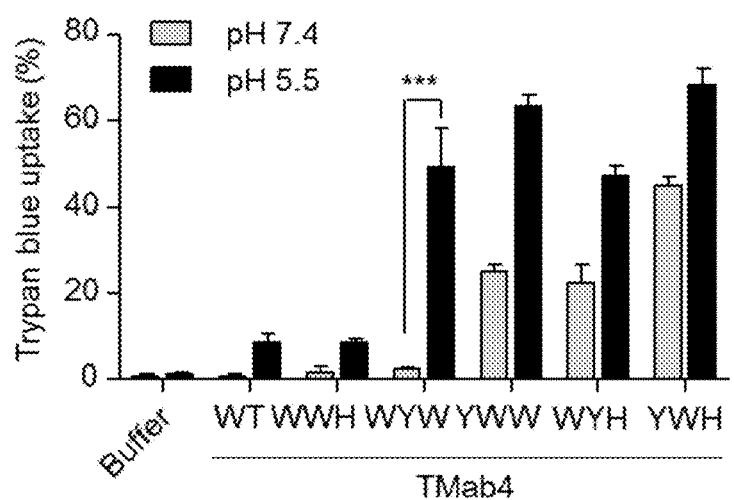

[Figure 17a]
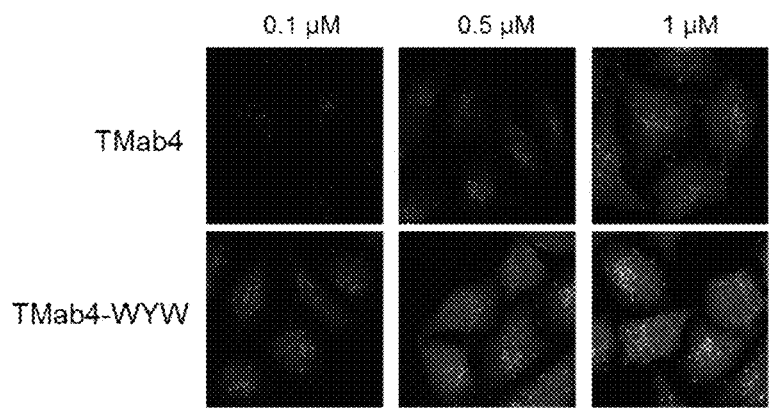
[Figure 17b]
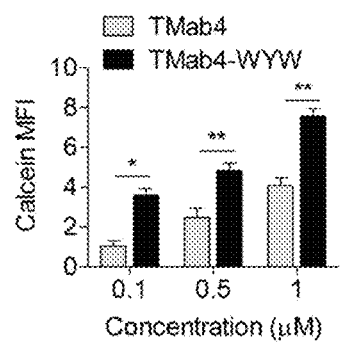
[Figure 18]
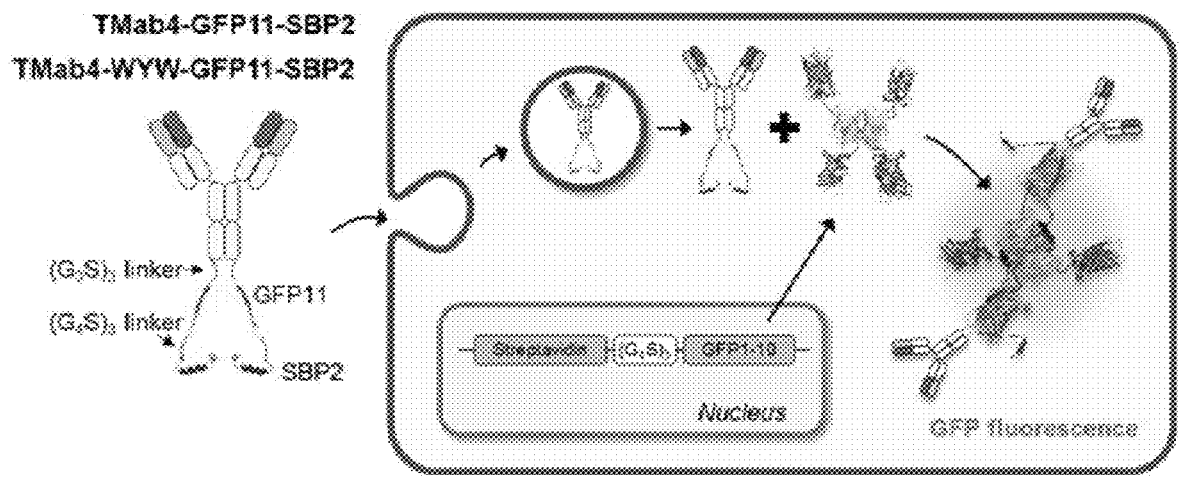

[Figure 19]
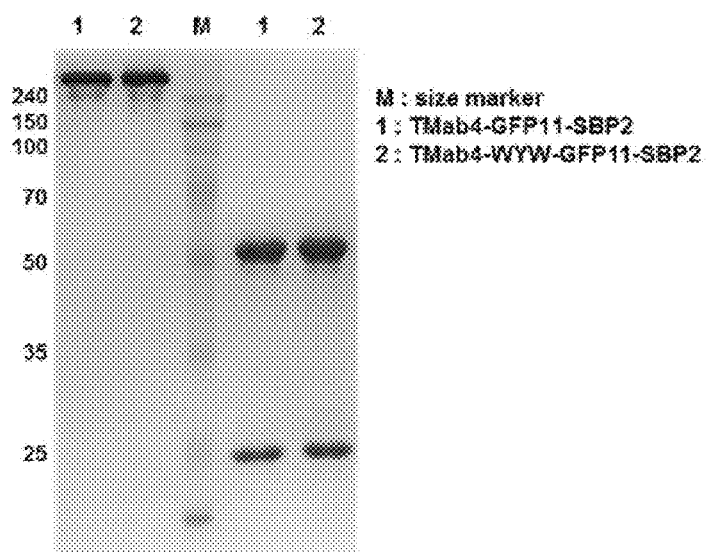
[Figure 20a]
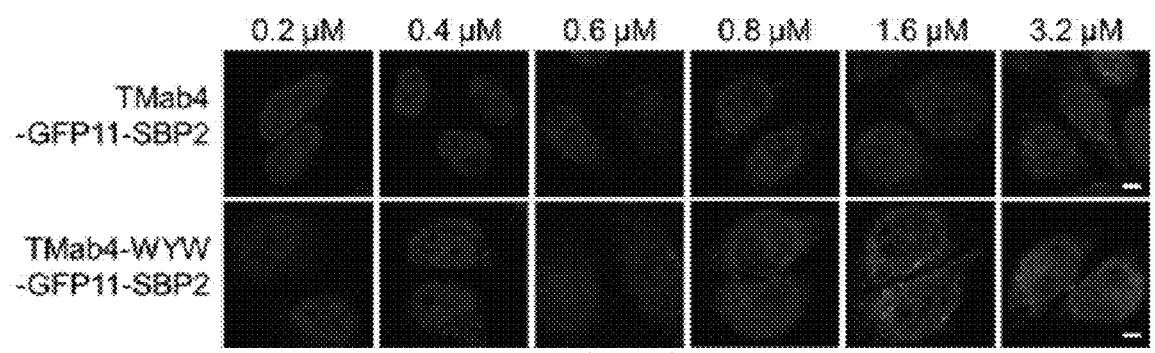

[Figure 20b]
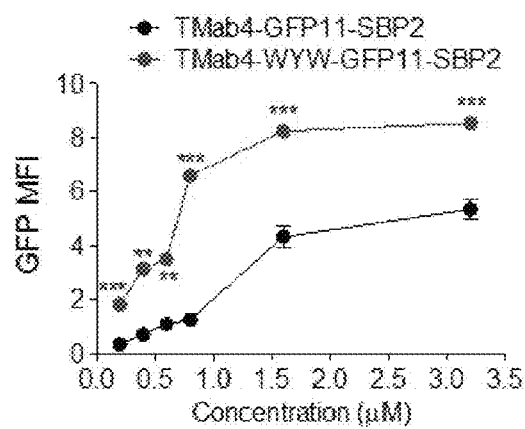
[Figure 21a]
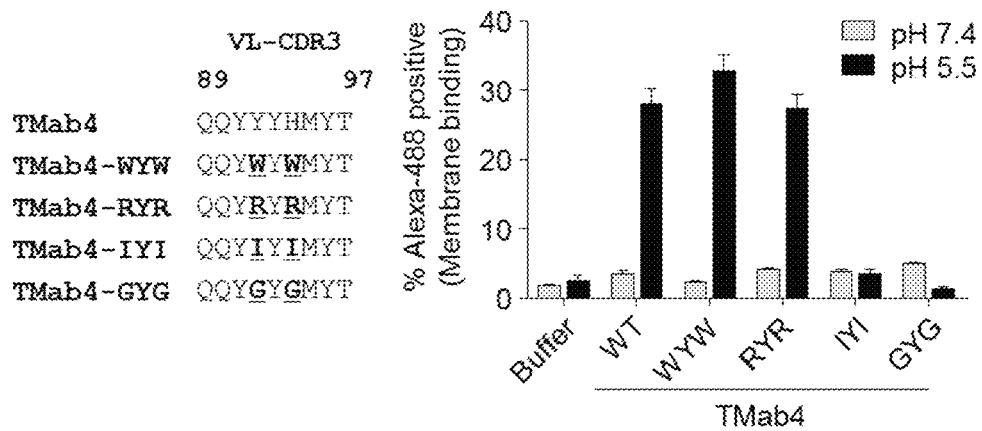

[Figure 21b]
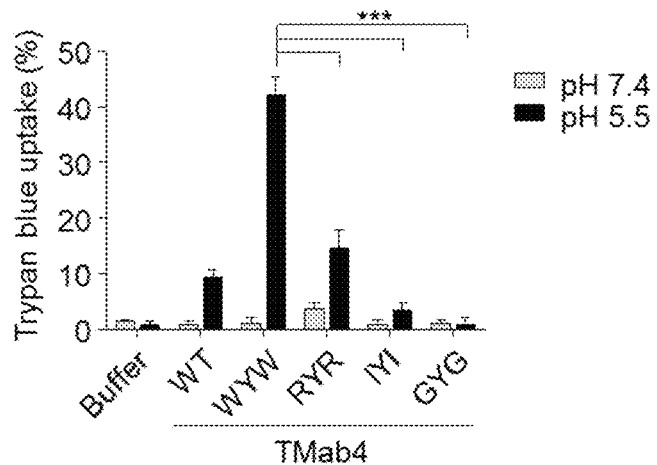
[Figure 21c]
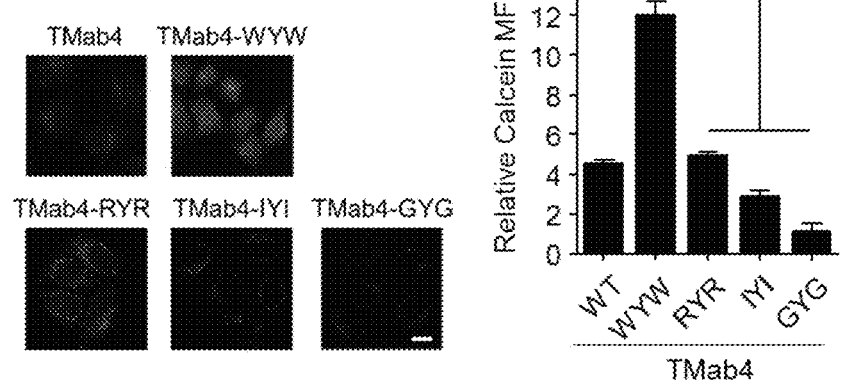

[Figure 22a]
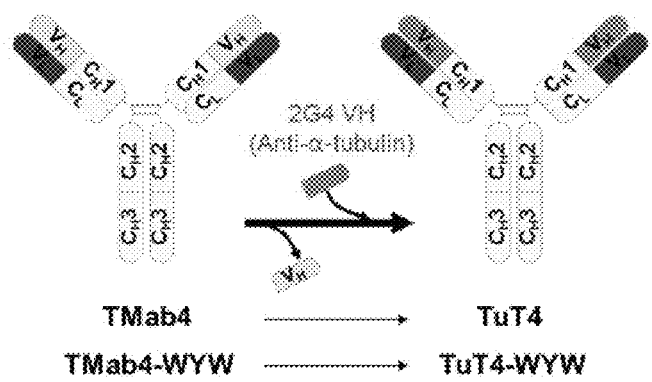
[Figure 22b]
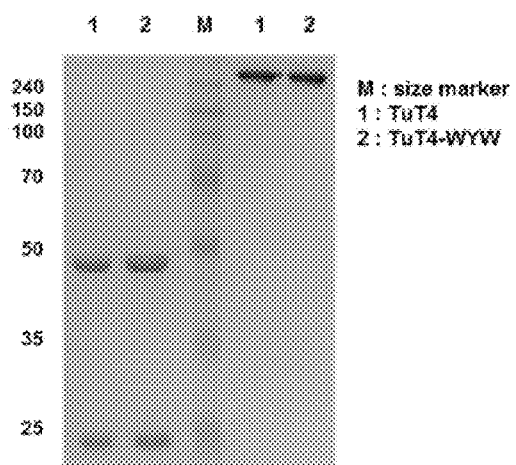

[Figure 22c]
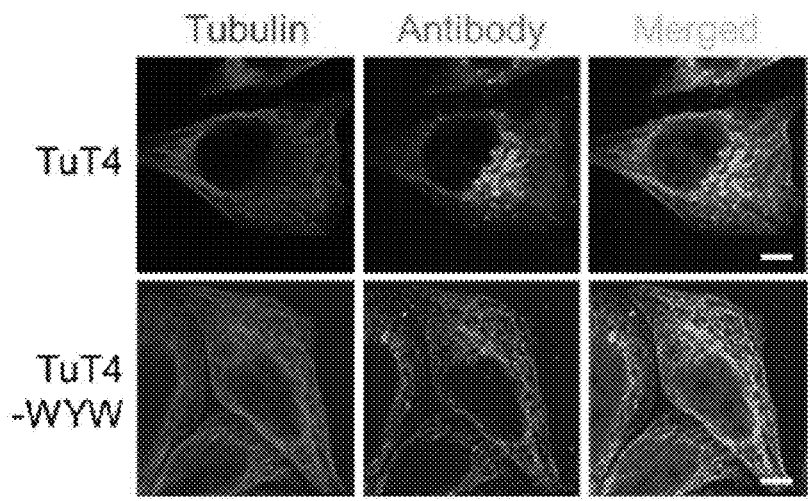
[Figure 23a]
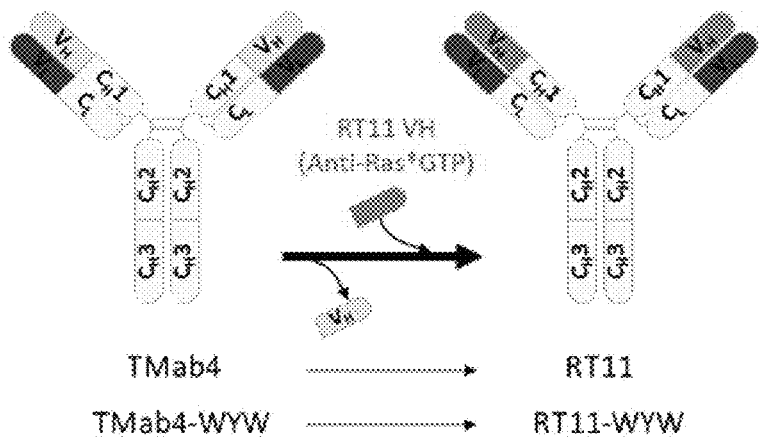

[Figure 23b]
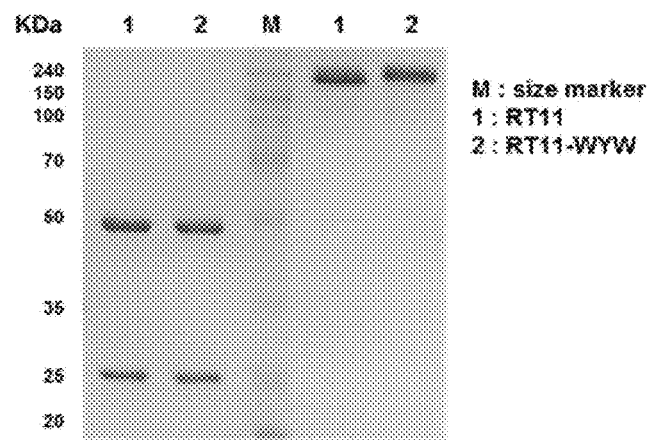
[Figure 23c]
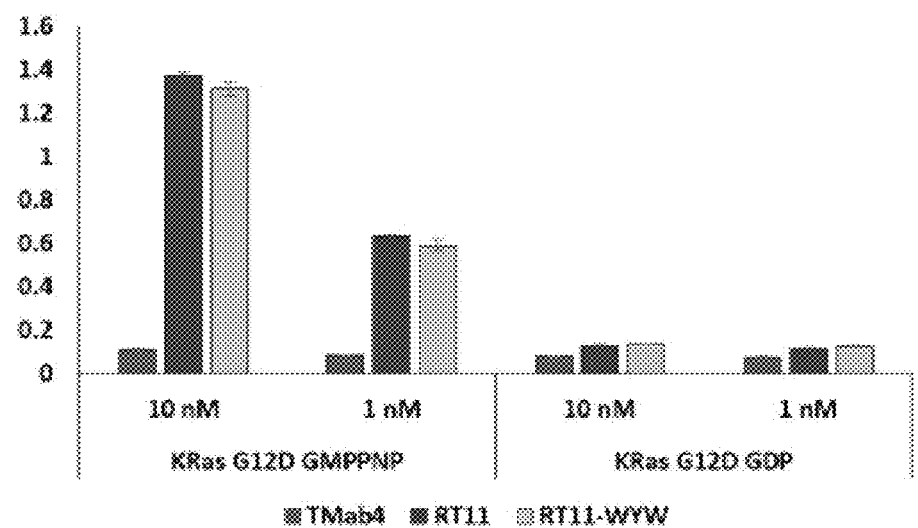

[Figure 24]
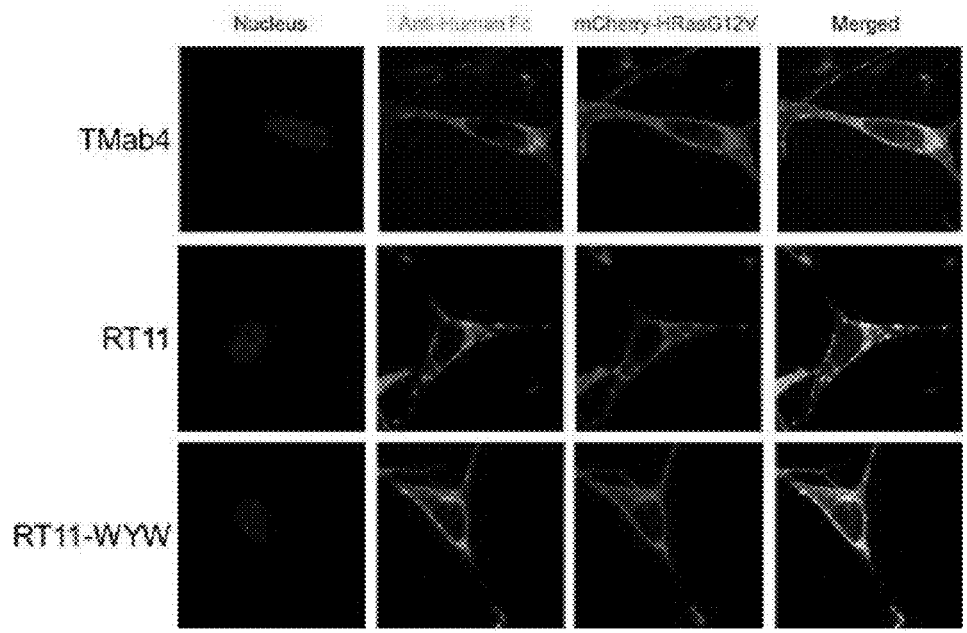
[Figure 25a]
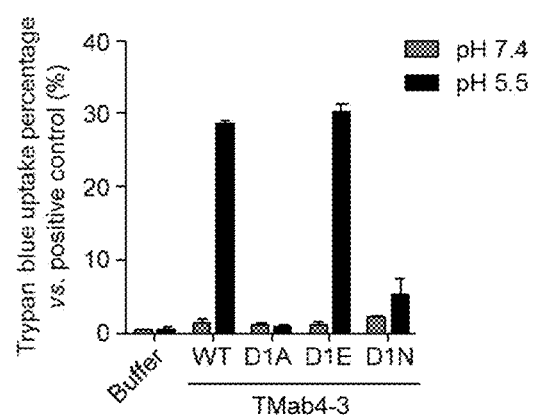

[Figure 25b]
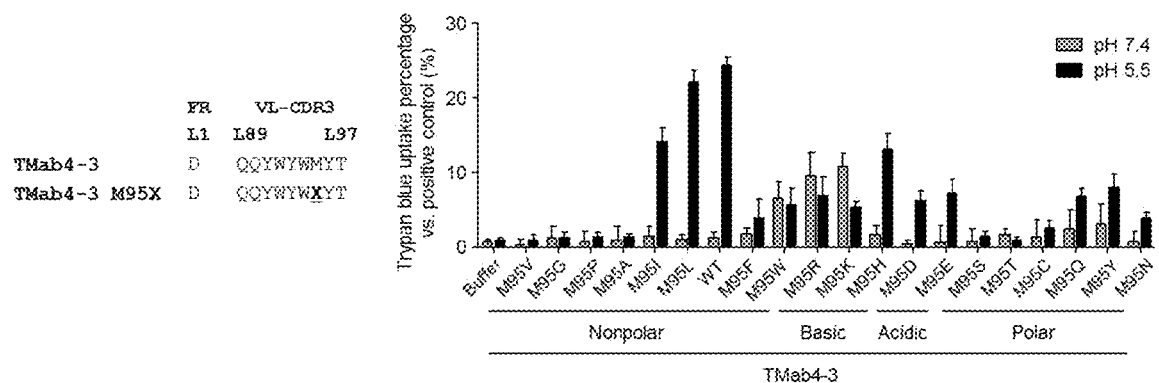
[Figure 26a]
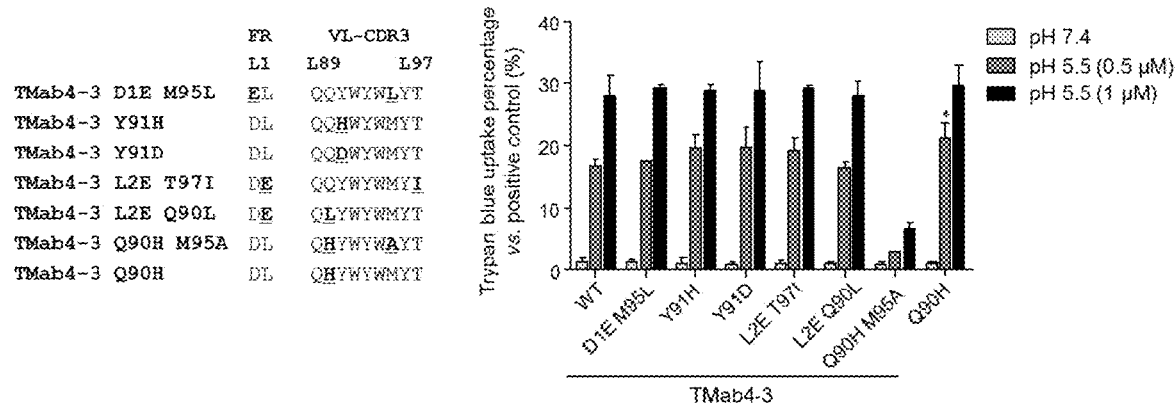
[Figure 26b]
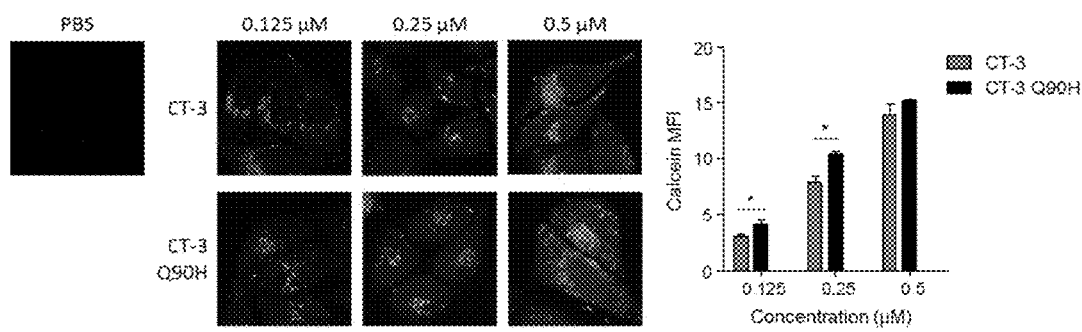

[Figure 27]
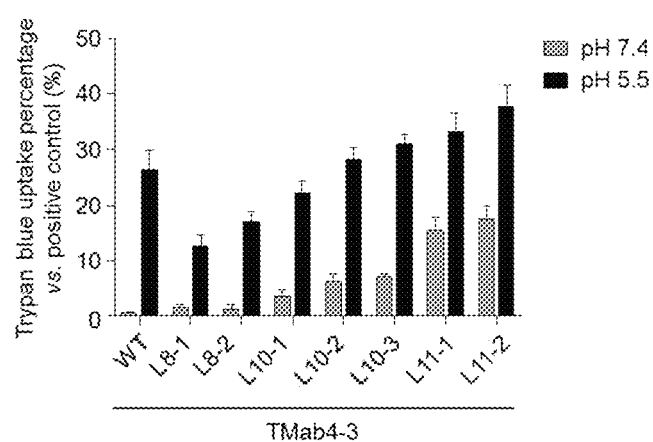
[Figure 28a]
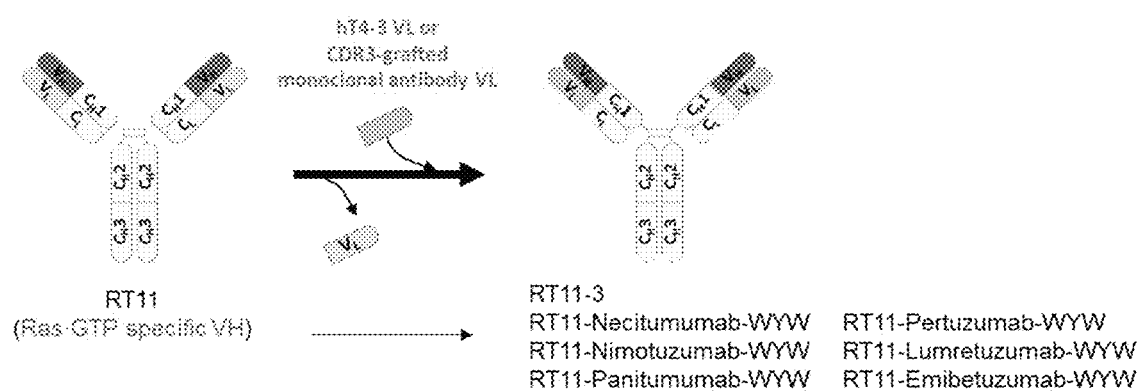

[Figure 28b]
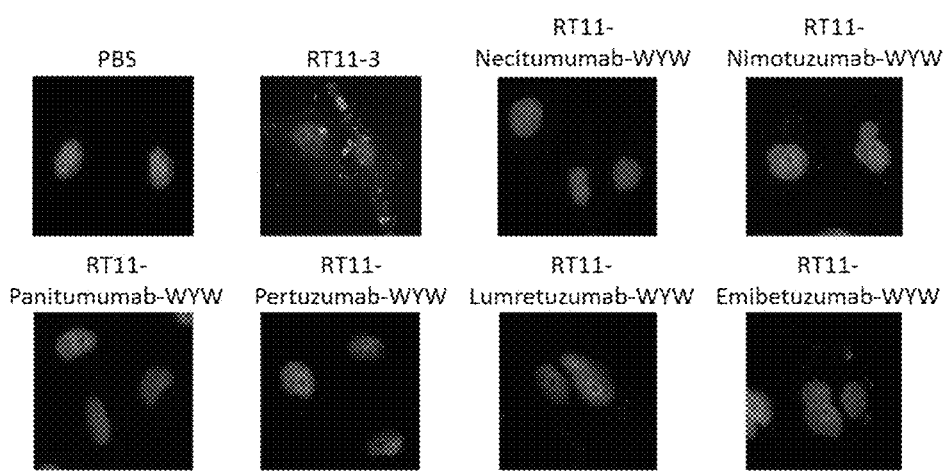
[Figure 28c]
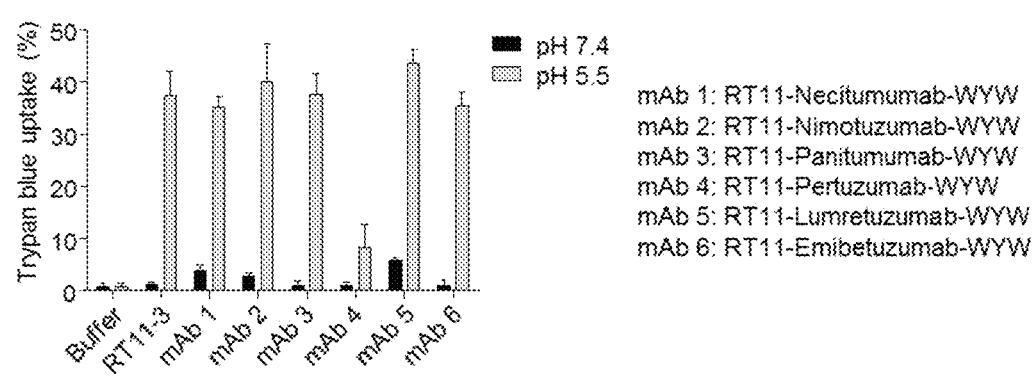

[Figure 29a]
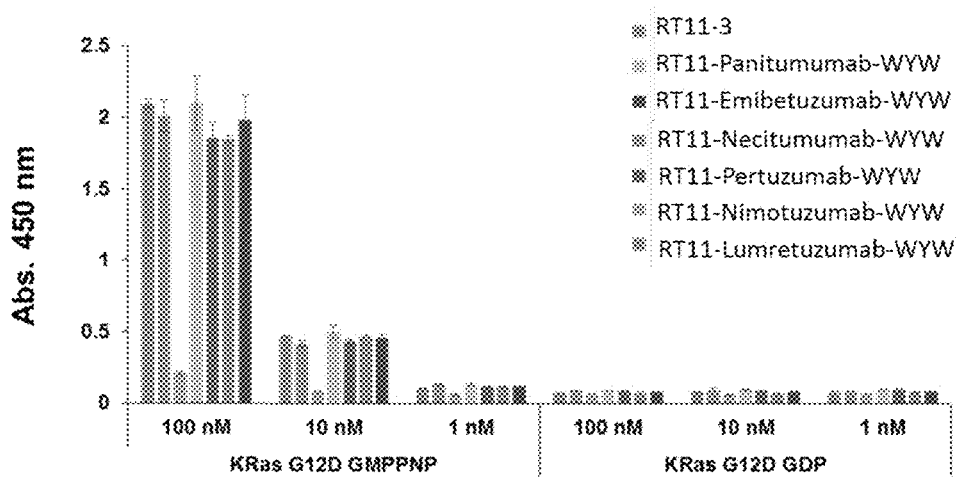
[Figure 29b]
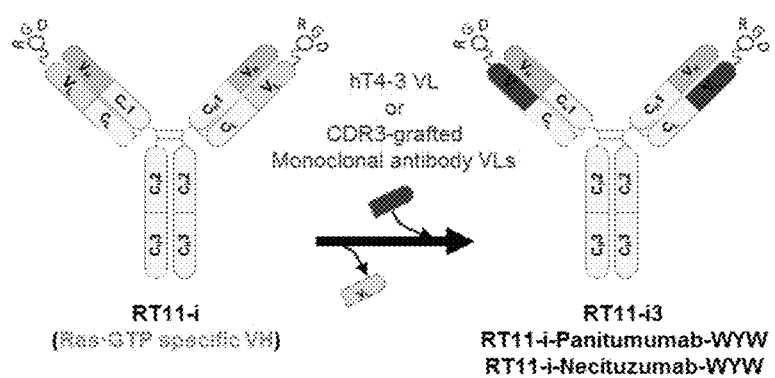

【Figure 29c】
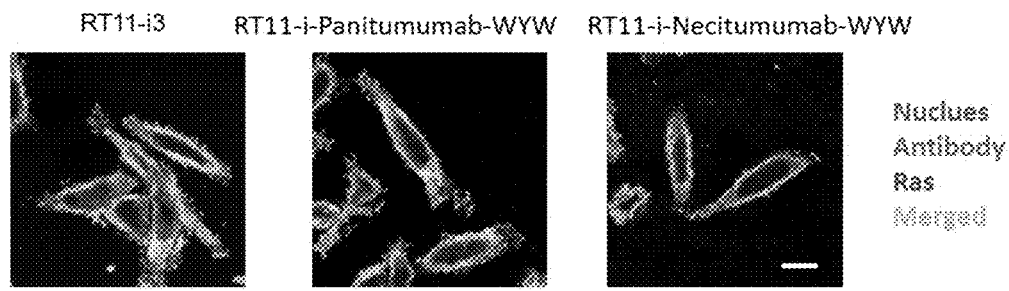
【Figure 30a】
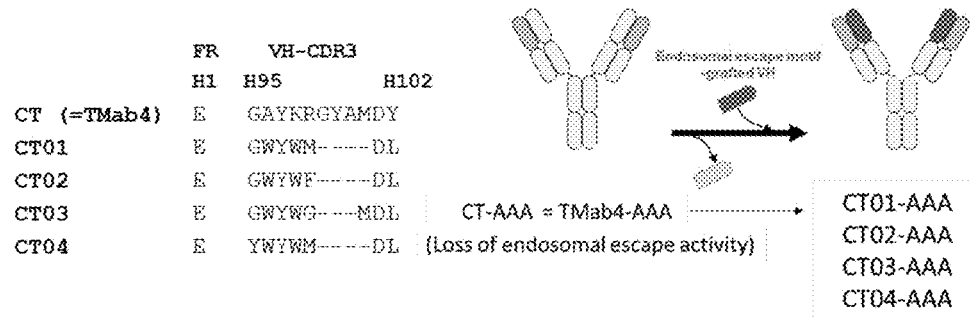
【Figure 30b】
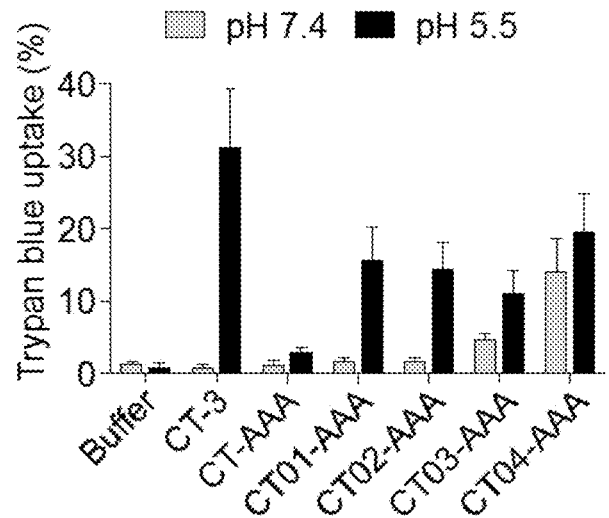

[Figure 30c]
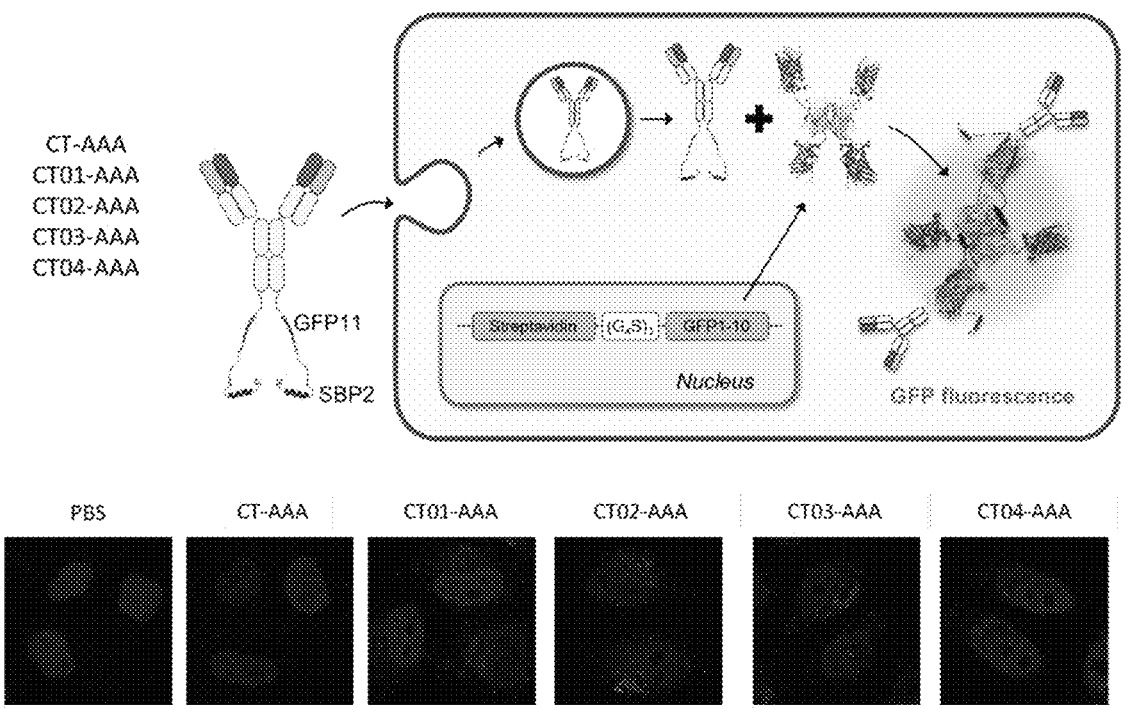
[Figure 30d]
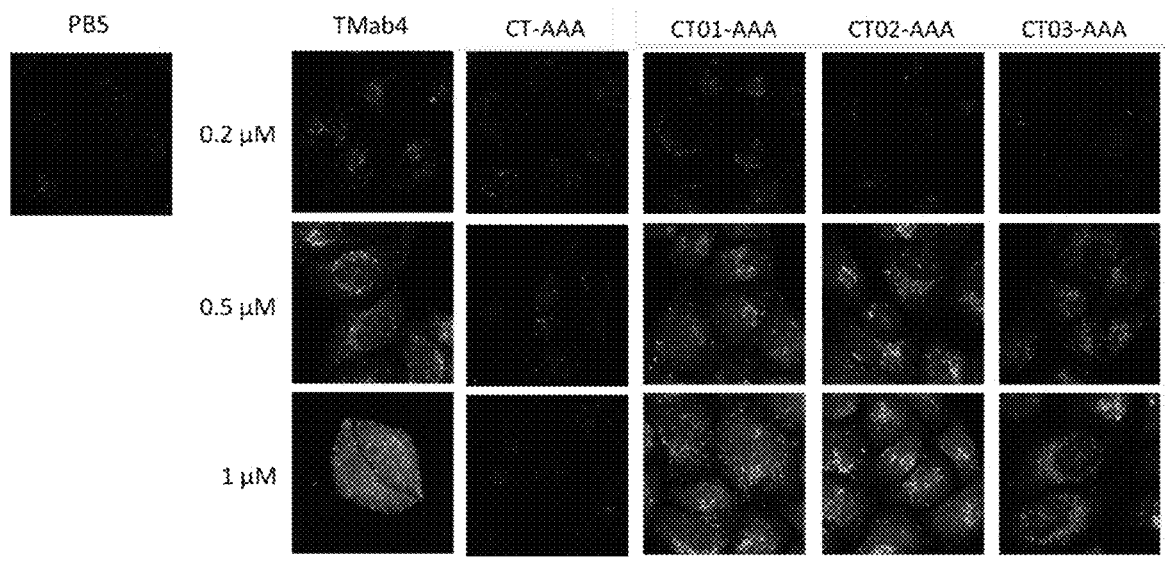

[Figure 31a]
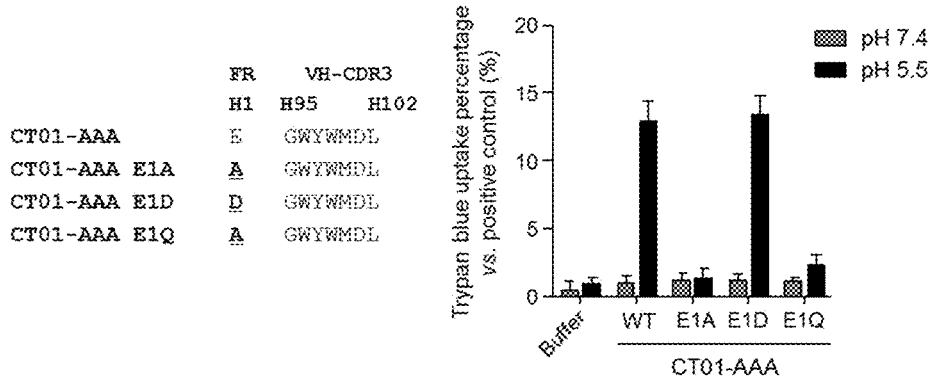
[Figure 31b]
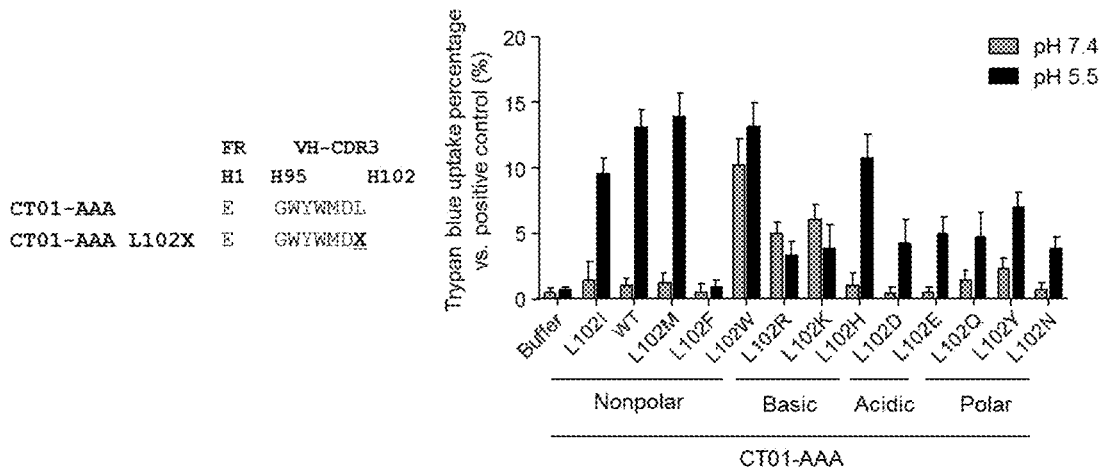

[Figure 32a]
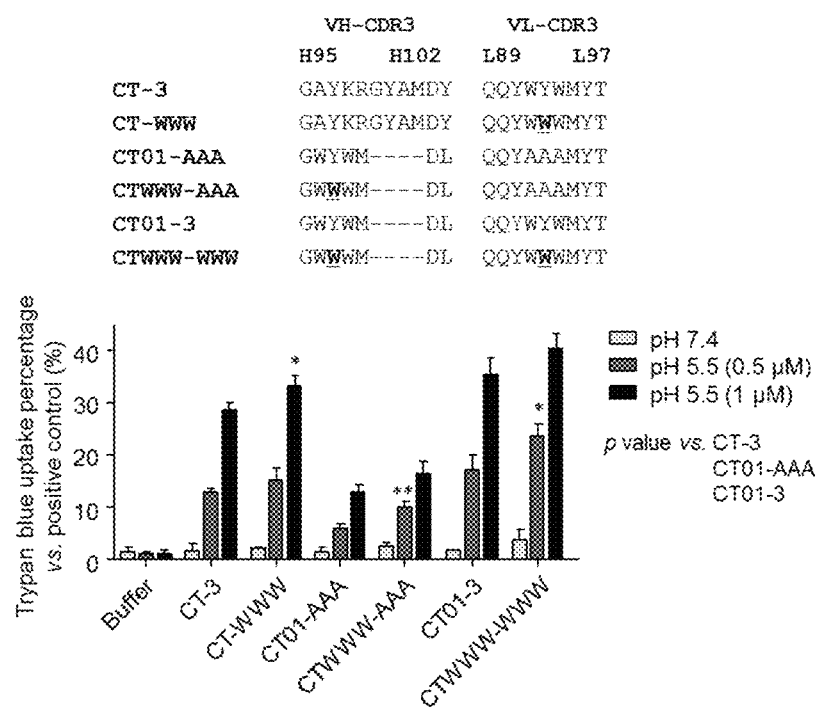

[Figure 32b]
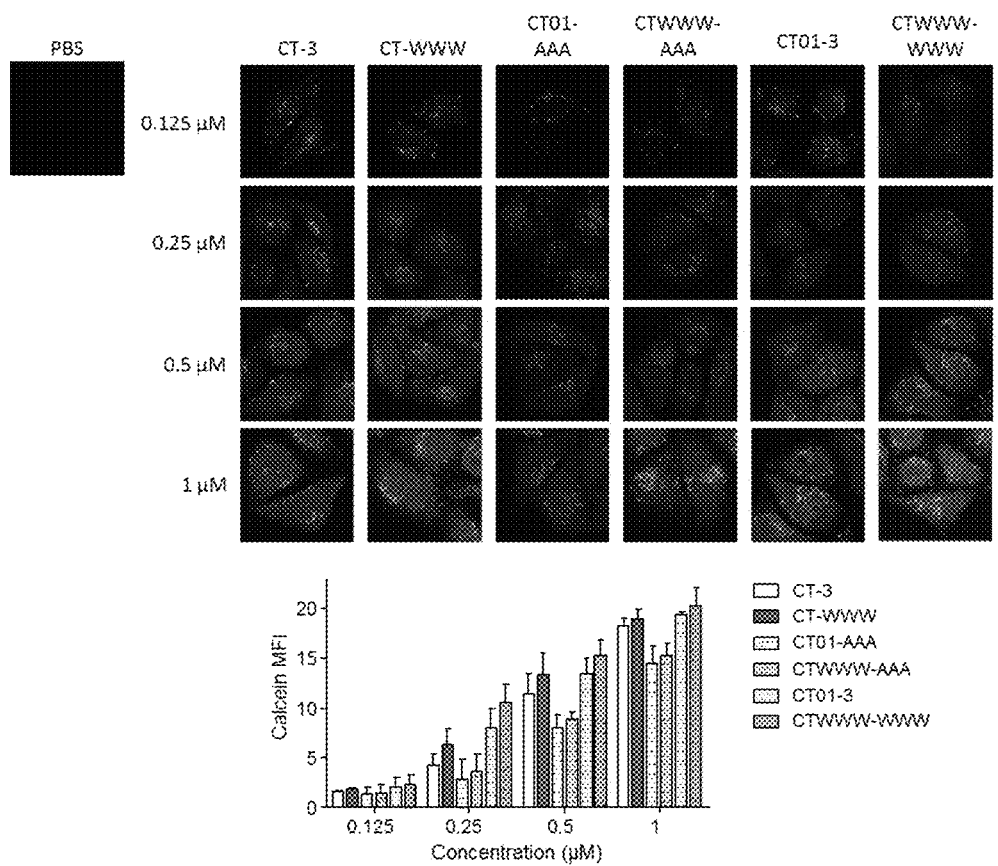
[Figure 33a]
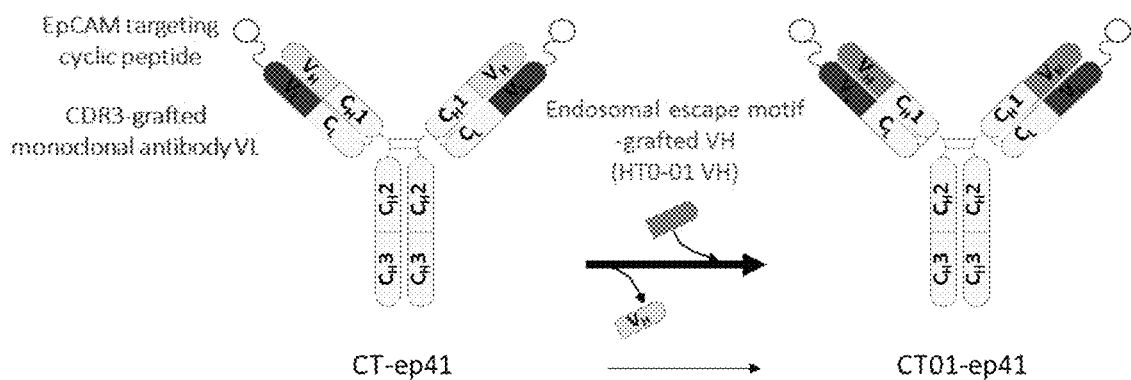

[Figure 33b]
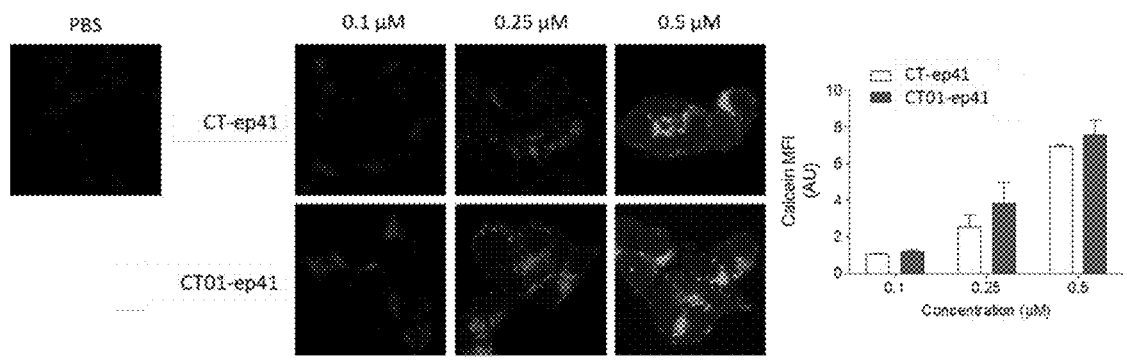
[Figure 33c]
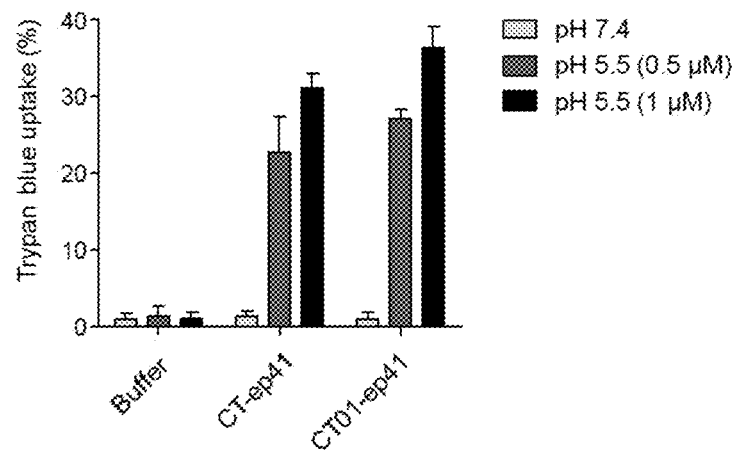

[Figure 34a]
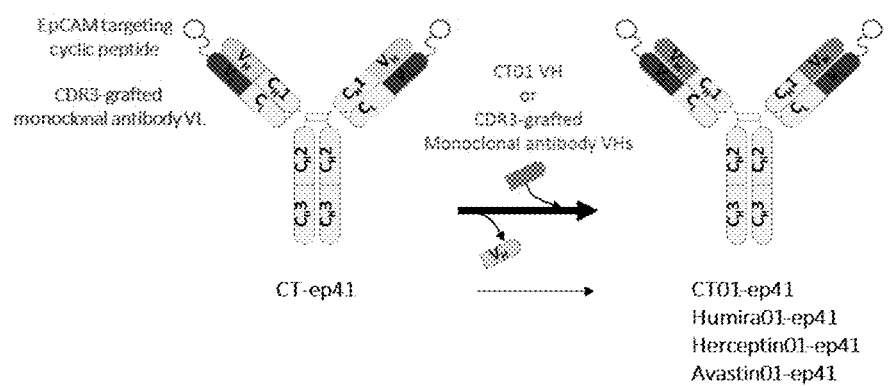
[Figure 34b]
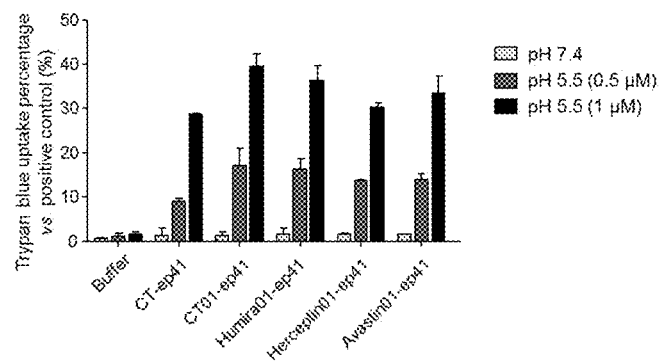

[Figure 35]

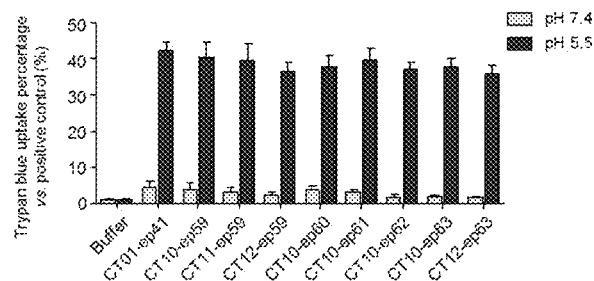

|  | FR1 | VH-CDR1 | VH-CDR2 |
|---|---|---|---|
|  | H1 | H32 | H58 |
| CT10 VH | E ... AASGFTFS | [DFSMS] | YISRTSHTTYYADSVKG |
| CT11 VH | E ... AASGFT<u>DD</u> | [DFSMS] | YISRTSHTTYYADSVKG |
| CT12 VH | E ... AASGFT<u>DD</u> | [DFSMS] | YISRTSHTT<u>D</u>YADSVKG |

|  | FR1 | VL-CDR1 | VL-CDR2 |
|---|---|---|---|
|  | L1 | L27b | L50 |
| hT4-59 | D | KSSQSLLNSRDGKNYLA | WASTRES |
| hT4-60 | D | KSSQS<u>D</u>LNSRDGKNYLA | WASTRES |
| hT4-61 | D | KSSQSLLNSRDGKNYLA | <u>D</u>ASTRES |
| hT4-62 | D | KSSQSLLNSRDGKNYLA | <u>DD</u>STRES |
| hT4-63 | D | KSSQS<u>D</u>LNSRDGKNYLA | <u>DD</u>STRES |

[Figure 36a]

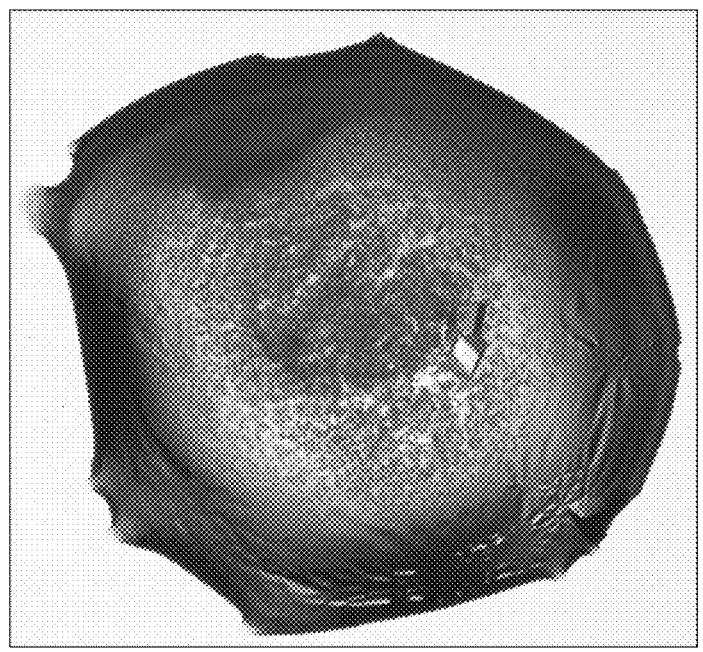

[Figure 36b]
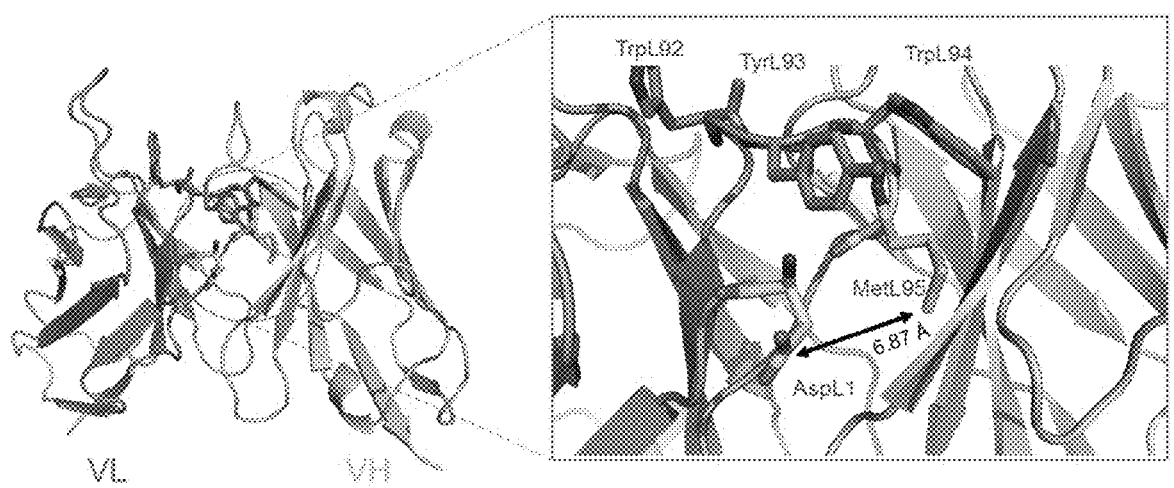

CYTOSOL-PENETRATING ANTIBODY AND USE THEREOF

CROSS-REFERENCE TO RELATED APPLICATIONS

This application is a U.S. national phase under the provisions of 35 U.S.C. § 371 of International Patent Application No. PCT/KR17/05559 filed May 26, 2017, which in turn claims priority of Korean Patent Application No. 10-2016-0065365 filed May 27, 2016, Korean Patent Application No. 10-2016-0065379 filed May 27, 2016, and Korean Patent Application No. 10-2017-0065670 filed May 26, 2017. The disclosures of such international patent application and Korean priority patent applications are hereby incorporated herein by reference in their respective entireties, for all purposes.

This application incorporates by reference in its entirety the Computer Readable Form (CRF) of a Sequence Listing in ASCII text format submitted via EFS-Web. The Sequence Listing text file submitted via EFS-Web, entitled "14532-005-999_Substitute_Seq_Listing.txt", was created on Apr. 16, 2021 and is 78,930 bytes in size.

TECHNICAL FIELD

The present disclosure relates to a cytosol-penetrating antibody and the use thereof, and more particularly to an endosomal escape motif which can increase the endosomal escape efficacy of a cytosol-penetrating antibody (Cytotransmab) so as to have a significantly improved ability to escape from endosomes into the cytosol after cellular internalization into living cells through a cell membrane protein, a light-chain variable region and/or heavy-chain variable region comprising the same, a cytosol-penetrating antibody comprising the same, a method for producing the same, and the use thereof.

BACKGROUND ART

General antibodies and macromolecular bio-drugs have limitations in that they cannot pass the hydrophobic cell membrane, and thus cannot bind to and inhibit various disease-related substances. In addition, conventional antibodies cannot directly penetrate living cells due to their large size and hydrophilic nature.

Thus, most conventional antibodies specifically target extracellularly secreted proteins or cell membrane proteins.

Further, generally, commercial antibodies binding specifically to intracellular substances which are used in experiments for studies on mechanisms such as the growth, specific inhibition, etc. of cells, cannot be used directly to treat living cells, and in order for these antibodies to bind to intracellular substances, a pretreatment process for forming pores in the cell membrane by a cell membrane permeabilization process using the amphipathic glycoside saponin is necessarily required.

A number of therapeutic antibodies that target cell membrane proteins or extracellularly secreted proteins due to their property of binding to target proteins with high specificity and high affinity have been developed. Antibodies that target cell membrane proteins can bind to cell membrane proteins, and then enter the cells via an endosomal pathway through a receptor-mediated endocytosis process.

This process includes various pathways after the early endosome stage. That is, 1) most antibodies can be transported from early endosomes to late endosomes and lysosomes, and can be completely degraded by proteases under acidic conditions; and 2) some antibodies can bind to FcRn (neonatal Fc receptor) in early endosomes under acidic conditions and come out of the cells through the recycling endosome pathway.

Thus, most antibodies bind strongly to the target membrane proteins and are mostly degraded through the lysosomal pathway. In the endosomal pathway, endosomes are matured while the inside thereof is gradually acidified by proton pumps. It is known that the pH of early endosomes is about 5.5-6.5, the pH of late endosomes is about 4.5-5.5, and the pH of lysosomes is about pH 3.5-4.5 (Quadir M A et al., 2014; Li S et al., 2014). Many proteinases in endosomes are activated, and endocytosed proteins are degraded in endosomes.

Consequently, when antibodies move through the endosomal pathway after receptor-mediated endocytosis, they should be separated from the target membrane proteins and form pores in endosomes in order to escape from early or late endosomes into the cytosol before trafficking to lysosomes.

Among naturally occurring intracellular substances, viruses and toxins are known to actively penetrate living cells through endocytosis. "Endosomal escape", a process of escaping from endosomes into the cytosol, is essential so that a substance that penetrated into cells by endocytosis exhibits activity in the cytosol.

Although the endosomal escape mechanism has not yet been clearly found, three hypotheses for the endosomal escape are known to date.

The first hypothesis is a mechanism by which a pore is formed in the endosomal membrane. In this hypothesis, substances such as cationic amphiphilic peptides in the endosomal membrane bind to a negatively charged cellular lipid bilayer to cause internal stress or inner membrane contraction to thereby form a barrel-stave pore or a toroidal channel (Jenssen et al., 2006), which is called a pore formation mechanism.

The second hypothesis is a mechanism by which the endosome bursts as a consequence of the proton-sponge effect. In this hypothesis, due to the high buffering effect of a substance having a protonated amino group, the osmotic pressure of the endosome can be increased so that the endosomal membrane can be degraded (Lin and Engbersen, 2008).

In the third hypothesis, a specific motif, which maintains a hydrophilic coil shape in a neutral environment but is changed into a hydrophobic helical structure in an acidic environment such as endosome, is fused to the endosomal membrane so that viruses and toxins including a motif escape from the endosome, which is called a lipid membrane fusion mechanism. These three hypothese has been proposed as endosome escape mechanisms after endocytosis of a viral protein and a toxic protein derived from plants/bacteria, but such endosome escape mechanism in antibodies has not been specifically identified yet.

The common phenomenon observed in the above-described endosomal escape mechanism is that endosomal escape occurs under acidic pH conditions which are endosomal and lysosomal environments. Proteins whose function changes depending on pH have the property of changing their structure depending on pH. Negatively charged amino acids (asparaginic acid (D) and glutamic acid (E)) and hydrophobic amino acids (methionine (M), leucine (L), and isoleucine (I)) do not interact under neutral pH conditions. However, as pH decreases, the carboxylic acids (COO—) in the side chains of the negatively charged amino acids become hydrophobic by protonation (Korte et al., 1992), and then can hydrophobically interact with the surrounding hydrophobic amino acids. As a result, the distance between the two amino acids becomes closer, and the overall structure and function of the protein change. The phenomenon that causes this change is known as the Tanford transition (Qin et al., 1998).

As one example, nitrophorin 4, a nitrogen transporting enzyme, has an open structure under neutral pH conditions. However, as the pH decreases from neutral pH (pH 7.4) to weakly acidic pH (pH 6.0), the structure of nitrophorin 4 changes to a closed structure by the hydrophobic interaction of asparaginic acid and leucine, and thus nitrophorin 4 functions to transport nitrogen (Di Russo et al., 2012).

However, this pH-dependent structural change has not yet been found in antibodies. In particular, this change has not yet been observed in antibodies that undergo endocytosis.

As one example, an antibody engineering improvement technology for inducing pH-dependent antigen binding among conventional antibody technologies is a method of screening pH-dependent antigen-binding antibodies from libraries introduced either with histidine (H) of CDRs (complementary determining regions) or with random mutations including histidine (Bonvin P et al., 2015). However, the two methods all cause no structural change, and have a limitation in that library-based screening should be performed in order to induce pH-dependent antigen binding.

In order to increase the effect of a substance that exhibits its activity in the cytosol, the amount of the substance located in the cytosol should ultimately increase. Hence, studies have been conducted to increase the endosomal escape ability. Such studies have been conducted mainly on cell-penetrating peptides (CPPs). Although it has been reported that some cell-penetrating peptides localize in the cytosol through an endosomal escape pathway, there is no detailed study on an exact endosomal escape mechanism, and it is known that only about 0.1 to 4% of endocytosed peptides localize to the cytosol due to very low endosomal escape efficiency.

Under this technical background, the present inventors have identified an endosomal escape motif capable of increasing the endosomal escape efficacy of a cytosol-penetrating antibody (Cytotransmab) that penetrates cells and localizes in the cytosol (Choi et al., 2014), and have found that it is possible to develop a light-chain or heavy-chain variable region including an endosomal escape motif having an increased ability to escape from endosomes, and an antibody or an antigen-binding fragment thereof comprising the same.

In addition, the present inventors have found that a cytosol-penetrating antibody having endosomal escape ability can be produced by grafting this endosomal escape motif into other kinds of light-chain or heavy-chain variable regions, thereby completing the present disclosure.

The information disclosed in the Background Art section is only for the enhancement of understanding of the background of the present disclosure, and therefore may not contain information that forms a prior art that would already be known to a person of ordinary skill in the art.

DISCLOSURE OF INVENTION

Technical Problem

It is an object of the present disclosure to provide a cytosol-penetrating antibody having endosome escape ability or an antigen-binding fragment thereof.

Another object of the present disclosure is to provide a nucleic acid encoding the antibody or antigen-binding fragment thereof.

Still another object of the present disclosure is to provide a vector comprising the above-described nucleic acid, a cell transformed with the above-described vector, and a method of producing the above-described antibody or antigen-binding fragment thereof.

Yet another object of the present disclosure is to provide an antibody-drug conjugate comprising the above-described antibody or antigen-binding fragment thereof.

A further object of the present disclosure is to provide a composition for delivering an active substance into cytosol, comprising the above-described cytosol-penetrating antibody or antigen-binding fragment thereof.

A still further object of the present disclosure is to provide a method for producing the above-described cytosol-penetrating antibody or antigen-binding fragment thereof.

Technical Solution

To achieve the above object, the present disclosure provides a cytosol-penetrating antibody or an antigen-binding fragment thereof comprising a light-chain variable region and/or heavy-chain variable region that comprises a sequence represented by the following formula in its CDR3:

X1-X2-X3-Z1 wherein X1-X2-X3 is an endosomal escape motif, and each of X1, X2 and X3 is selected from the group consisting of tryptophan (W), tyrosine (Y), histidine (H) and phenylalanine (F);

Z1 is selected from the group consisting of methionine (M), isoleucine (I), leucine (L), histidine (H), asparaginic acid (D), and glutamic acid (E);

the light-chain variable region and/or heavy-chain variable region comprising Z1 induces a change in properties of the antibody under endosomal acidic pH conditions; and the antibody exhibits an ability to escape from endosomes into the cytosol through the change in properties of the antibody.

In the cytosol-penetrating antibody or antigen-binding fragment thereof according to the present disclosure, the first amino acid of the light-chain variable region and/or heavy-chain variable region may be asparaginic acid (D) or glutamic acid (E).

The present disclosure also provides a nucleic acid encoding the above-described cytosol-penetrating antibody or antigen-binding fragment thereof.

The present disclosure also provides a vector comprising the above-described nucleic acid.

The present disclosure also provides a cell transformed with the above-described vector.

The present disclosure also provides a composition for delivering an active substance into cytosol, comprising the above-described cytosol-penetrating antibody or antigen-binding fragment thereof.

The present disclosure also provides a method for producing the above-described cytosol-penetrating antibody or antigen-binding fragment thereof, the method comprising a step of grafting the endosomal escape motif X1-X2-X3-Z1 (wherein X1-X2-X3 is selected from the group consisting of tryptophan (W), tyrosine (Y), histidine (H), and phenylalanine (F)) into the CDR3 of a light-chain and/or heavy-chain variable region.

Advantageous Effects

The cytosol-penetrating antibody or antigen-binding fragment thereof comprising the light-chain variable region and/or heavy-chain variable region comprising the endosomal escape motif according to the present disclosure penetrates living cells and localizes in the cytosol, and ultimately the antibody or antigen-binding fragment thereof can be penetrate living cells and localize in the cytosol without having to use a special external protein delivery system.

The cytosol-penetrating antibody or antigen-binding fragment thereof according to the present disclosure is a cytosol-penetrating antibody or antigen-binding fragment thereof comprising a light-chain variable region or a heavy-chain variable region that easily interacts with and binds to various human light-chain variable regions or heavy-chain variable regions (VHs), and has the ability to escape from endosomes into the cytosol. The antibody or antigen-binding fragment thereof can penetrate cells and localize in the cytosol, and does not show non-specific cytotoxicity for target cells.

Based on the endosomal escape mechanism for the high efficiency cytosol-penetrating antibody or an antigen-binding fragment thereof according to the present disclosure, a design of antibody libraries for improving the endosomal escape ability and mutants can be performed.

The endosomal escape motif included in the cytosol-penetrating antibody or antigen-binding fragment thereof according to the present disclosure is introduced into other antibodies so that it can be expected to impart the endosomal escape ability.

In addition, the cytosol-penetrating antibody or antigen-binding fragment thereof according to the present disclosure can be utilized as a carrier that delivers an active substance into the cytosol of a living cell, and can also be utilized as a pharmaceutical composition for treatment and prevention of diseases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows of a pulse-chase experiment and confocal microscopy observation performed to observe the transport process and stability of the cytosol-penetrating antibody (cytotransmab) TMab4 or cell-penetrating peptide TAT introduced into cells.

FIG. 2*a* shows the results of confocal microscopy observation of the cytosol-penetrating ability of the cytosol-penetrating antibody TMab4 or the cell-penetrating peptide TAT in the presence or absence of an inhibitor thereof.

FIG. 2*b* is a bar graph showing the results of quantifying the FITC (green fluorescence) fluorescence of the confocal micrographs shown in FIG. 2*a*.

FIG. 2*c* shows the results of observing the cytosolic localization of the cytosol-penetrating antibody TMab4 or the cell-penetrating peptide TAT by confocal microscopy using calcein in the presence or absence of an inhibitor thereof.

FIG. 2*d* is a bar graph showing the results of quantifying the calcein fluorescence of the confocal micrographs shown in FIG. 2*c*.

FIG. 3*a* shows the results of Western blot analysis performed to confirm siRNA (short interfering RNA)-induced inhibition of heparanase expression.

FIG. 3*b* shows the results of confocal microscopy observation of cytosol penetrating antibody/lysosome merging caused by inhibition of heparanase expression.

FIG. 3*c* shows the results of confocal microscopy observation performed to confirm the cytosolic localization of a cytosol-penetrating antibody, which is caused by inhibition of heparanase expression.

FIG. 4 is a schematic view showing an overall trafficking process ranging from cellular internalization of a cytosol-penetrating antibody to localization of the antibody in the cytosol.

FIG. 5 shows the results of observing a fluorescence-labeled cytosol-penetrating antibody in Ramos cells by confocal microscopy in order to examine whether the antibody can be introduced through the cell membrane depending on pH or whether the antibody can induce cell membrane permeation of other substances.

FIG. 6*a* shows the results of observing Ramos cells by an optical microscope in order to examine whether a cytosol-penetrating antibody can form pores and take up trypan blue having no membrane-permeating ability, depending on pH.

FIG. 6*b* is a graph quantitatively comparing the number of cells that have taken up trypan blue.

FIG. 7*a* shows the results of optical microscopic observation performed to confirm whether cell membrane pores produced by a cytosol-penetrating antibody at pH 5.5 is temporary and reversible.

FIG. 7*b* is a graph quantitatively comparing the number of cells that have taken up trypan blue uptake.

FIG. 8 shows the results of analyzing the cell membrane binding of a cytosol-penetrating antibody and control antibody adalimumab by flow cytometry (FACS) at varying pHs.

FIG. 9 shows the results of analyzing the cell membrane flip-flop inducing abilities of a cytosol-penetrating antibody and control antibody adalimumab by flow cytometry (FACS) at varying pHs.

FIG. 10 is a schematic view showing a pore formation model of a cytosol-penetrating antibody, expected based on the above-described experiments.

FIG. 11 shows the results of predicting the pH-dependent structural change of a cytosol-penetrating antibody on the basis of the WAM modeling structure of the light-chain variable region of the cytosol-penetrating antibody, and shows amino acids, which are involved in the structural change, and amino acids which are exposed by the structural change.

FIG. 12 is a graph quantitatively comparing the number of cells that have taken up trypan blue depending on pH by mutants constructed by substituting the 1st amino acid asparaginic acid and 95th amino acid methionine of a light-chain variable region (VL), which induce a change in properties of a cytosol-penetrating antibody at acidic pH, with alanine, glutamic acid and leucine, respectively. The VL CDRs of TMab4 (QQYYYHMYT, SEQ ID NO: 79), TMab4-D1A (QQYYYHMYT, SEQ ID NO: 79), TMab4-M95A (QQYYYHAYT, SEQ ID NO: 80), TMab4-D1E (QQYYYHMYT, SEQ ID NO: 79), and TMab4-M95L (QQYYYHLYT, SEQ ID NO: 81) are shown.

FIG. 13 is a graph quantitatively comparing the number of cells that have taken up trypan blue depending on pH by mutants constructed by substituting particular amino acids of the CDR3 of the light-chain variable region (VL) of a cytosol-penetrating antibody, which can possibly be involved in endosomal escape, with alanine. The VL CDR3 of TMab4 (QQYYYHMYT, SEQ ID NO: 79), TMab4-Y91A (QQAYYHMYT, SEQ ID NO: 82), TMab4-Y92A (QQYAYHMYT, SEQ ID NO: 83), TMab4-Y93A (QQYYAHMYT, SEQ ID NO: 84), TMab4-H94A (QQYYYAMYT SEQ ID NO: 85), TMab4-AAA (QQYAAAMYT, SEQ ID NO: 86), and TMab4-Y96A (QQYYYHMAT, SEQ ID NO: 87)

FIG. 14a shows the results of confocal microscopy performed to analyze the cytosol-penetrating ability of mutants constructed by substituting the CDR1 and CDR2 of the light-chain variable region (VL) of a cytosol-penetrating antibody, which bind to HSPG receptor and are involved in cytosol-penetrating ability, with human germline sequences.

FIG. 14b shows a graph quantitatively comparing the number of cells that have taken up trypan blue depending on pH by mutants constructed by substituting the CDR1 and CDR2 of the light-chain variable region (VL) of a cytosol-penetrating antibody, which bind to HSPG receptor and are involved in cytosol-penetrating ability, with human germline sequences.

FIG. 15a shows the results of 12% SDS-PAGE analysis under reducing or non-reducing conditions after purification of cytosol-penetrating antibody mutants expected to have improved endosomal escape ability. The VL CDR3 of TMab4 (QQYYYHMYT, SEQ ID NO: 79), TMab4-WWH (QQYWWHMYT, SEQ ID NO: 8), TMab4-WYH (QQYWYWMYT, SEQ ID NO: 9), TMab4-YWW (QQYYYWWYT, SEQ ID NO: 10), TMab4-WYH (QQYWYHMYT, SEQ ID NO: 11), and TMab4-YWH (QQYYYWMYT, SEQ ID NO: 12) are shown.

FIG. 15b shows the results of confocal microscopy performed to examine whether the cytosol-penetrating ability of cytosol-penetrating antibody mutants expected to have improved endosomal escape ability is maintained.

FIG. 16 is a graph quantitatively comparing the number of cells that have taken up trypan blue depending on pH by a cytosol-penetrating antibody wild-type and cytosol-penetrating antibody mutants expected to have improved endosomal escape ability.

FIG. 17a shows the results of observing the cytosolic localization of a cytosol-penetrating antibody wild-type and cytosol-penetrating antibody mutants expected to have improved endosomal escape ability, by confocal microscopy using calcein.

FIG. 17b is a bar graph showing the results of quantifying the calcein fluorescence of the confocal micrographs shown in FIG. 17a.

FIG. 18 is a schematic view showing a process in which GFP fluorescence by enhanced split-GFP complementation is observed when a cytosol-penetrating antibody wild-type and a mutant having improved endosomal escape ability localizes in the cytosol.

FIG. 19 shows the results of 12% SDS-PAGE analysis under reducing or non-reducing conditions after purification of a GFP11-SBP2-fused cytosol-penetrating antibody wild-type and a GFP11-SBP2-fused mutant having improved endosomal escape ability.

FIG. 20a shows the results of confocal microscopy performed to examine the GFP fluorescence of a GFP11-SBP2-fused cytosol-penetrating antibody wild-type and a GFP11-SBP2-fused mutant having improved endosomal escape ability by enhanced split-GFP complementation.

FIG. 20b is a graph showing the results of quantifying the GFP fluorescence of the confocal micrographs shown in FIG. 20a.

FIG. 21a is a graph showing the results of flow cytometry (FACS) performed to analyze the cell membrane binding of mutants obtained by substitution with arginine, isoleucine and glycine, which are amino acids having properties opposite to those of tryptophan. The VL CDR3 of TMab4 (QQYYYHMYT, SEQ ID NO: 79), TMab4-WYW (QQYWYWMYT, SEQ ID NO: 9), TMab4-RYR (QQYRYRMYT, SEQ ID NO: 88), TMab4-IYI (QQYIYIMYT, SEQ ID NO: 89), TMab4-GYG (QQYGYGMYT, SEQ ID NO: 90) are shown.

FIG. 21b is a graph quantitatively comparing the number of cells that have taken up trypan blue depending on pH by mutants obtained by substitution with arginine, isoleucine and glycine, which are amino acids having properties opposite to those of tryptophan.

FIG. 21c is a bar graph showing the results of observing the cytosolic localization of mutants obtained by substitution with arginine, isoleucine and glycine, which are amino acids having properties opposite to those of tryptophan by confocal microscopy using calcein and quantifying the calcein fluorescence of the confocal micrographs.

FIG. 22a is a schematic view showing a process of constructing an intact IgG-format anti-tubulin cytosol-penetrating antibody to be used to examine the activity of cytosol-penetrating antibody mutants having improved endosomal escape ability.

FIG. 22b shows the results of 12% SDS-PAGE analysis under reducing or non-reducing conditions after purification of an intact IgG-format anti-tubulin cytosol-penetrating antibody.

FIG. 22c shows the results of confocal microscopy performed to examine whether an intact IgG-format anti-tubulin cytosol-penetrating antibody would merge with cytoskeletal tubulin localized in the cytosol.

FIG. 23a is a schematic view showing a process of constructing an intact IgG-format RAS-targeting cytosol-penetrating antibody to be used to examine the activity of mutants having improved endosomal escape ability.

FIG. 23b shows the results of 12% SDS-PAGE analysis under reducing or non-reducing conditions after purification of intact IgG-format RAS-targeting cytosol-penetrating antibodies.

FIG. 23c shows the results of enzyme linked immunosorbent assay performed to measure the affinities of antibodies for GppNHp-bound K-RAS G12D and GDP-bound K-RAS G12D, which are K-RAS mutants.

FIG. 24 shows the results of confocal microscopy observation performed to examine whether intact IgG-format RAS-targeting cytosol-penetrating antibodies would merge with intracellular H-RAS G12V mutants.

FIG. 25a is a graph showing the results of quantitatively comparing the number of cells that have taken up trypan blue depending on pH by mutants constructed by substituting the 1st amino acid asparaginic acid of the light-chain variable region (VL) of a cytosol-penetrating antibody, which induce a change in properties of the cytosol-penetrating antibody at acidic pH 5.5, with various amino acids.

FIG. 25b is a graph showing the results of quantitatively comparing the number of cells that have taken up trypan blue depending on pH by mutants constructed by substituting 95th amino acid methionine of the light-chain variable region (VL) of a cytosol-penetrating antibody, which induce a change in properties of the cytosol-penetrating antibody at acidic pH 5.5, with various amino acids. The VL CDR3 of TMab4-3 (QQYWYWMYT, SEQ ID NO: 9) and TMab4-3 M95X (QQYWYWXYT, SEQ ID NO: 91) are shown.

FIG. 26a shows a graph showing quantitatively comparing the number of cells that have taken up trypan blue depending on pH by mutants designed for the purpose of inducing an additional change in properties in response to pH. The VL CDR3 of TMab4-3 DILE M95L (QQYYYHLYT, SEQ ID NO: 81), TMab4-3 Y91H (QQHWYWMYT, SEQ ID NO: 92), TMab4-3 Y91D (QQDWYWMYT, SEQ ID NO: 93), TMab4-3 L2E T97I (QQYWYWMYI, SEQ ID NO: 94), TMab4-3 L2E T9OL (QLYWYWMYT, SEQ ID NO: 95), TMab4-3 Q9OH M95A (QHYWYWAYT, SEQ ID NO: 96), and TMab4-3 Q9OH (QHYWYWMYT, SEQ ID NO: 24) are shown.

FIG. 26b shows a bar graph showing the results of observing the cytosolic localization of mutants designed for the purpose of inducing an additional change in properties in response to pH by confocal microscopy using calcein and quantifying the calcein fluorescence of the confocal micrographs.

FIG. 27 is a graph quantitatively comparing the number of cells that taken up trypan blue depending on pH by mutants obtained by changing the amino acid number of the CDR3 of the light-chain variable region of a cytosol-penetrating antibody. The VL CDR3 of TMab4-3 (QQYWYWMYT. SEQ ID NO: 9), TMab4-3 L8-1 (QQYWYW---MT, SEQ ID NO: 97), TMab4-3 L8-2 (QQWYWM---PT, SEQ ID NO: 98), TMab4-3 L10-1 (QQYWYWPM-YT, SEQ ID NO: 99), TMab4-3 L10-2 (QQYWYWYM-YT, SEQ ID NO: 100), TMab4-3 L10-3 (QQYWYWYM-YT, SEQ ID NO: 101), TMab4-3 L11-1 (QQYWYWLYMYT, SEQ ID NO: 102), and TMab4-3 L11-2 (QQYPWYWPMYT SEQ ID NO: 103) are shown.

FIG. 28a shows a process of constructing an intact IgG-format RAS-targeting cytosol-penetrating antibody in which an improved endosomal escape motif is introduced into the light-chain variable region of a conventional therapeutic antibody.

FIG. 28b shows the results of fluorescence microscopic observation performed to examine whether the HSPG binding affinity and cytosol-penetrating ability of an intact IgG-format RAS-targeting cytosol-penetrating antibody in which an improved endosomal escape motif is introduced into the light-chain variable region of a conventional therapeutic antibody would be reduced or eliminated.

FIG. 28c shows a graph quantitatively comparing the number of cells that taken up trypan blue at acidic pH by an intact IgG-format RAS-targeting cytosol-penetrating antibody in which an improved endosomal escape motif is introduced into the light-chain variable region of a conventional therapeutic antibody.

FIG. 29a shows the results of ELISA performed to measure the affinities of an intact IgG-format RAS-targeting cytosol-penetrating antibody, in which an improved endosomal escape motif is introduced into the light-chain variable region of a conventional therapeutic antibody, for GppNHp-bound K-RAS G12D and GDP-bound K-RAS G12D, which are K-RAS mutants.

FIG. 29b shows a schematic view showing a process of constructing an intact IgG-format RAS-targeting cytosol-penetrating antibody in which an improved endosomal escape motif is introduced into the RGD10 peptide-fused light-chain variable region of a conventional therapeutic antibody.

FIG. 29c shows the results of confocal microscopy performed to examine whether an intact IgG-format RAS-targeting cytosol-penetrating antibody in which an improved endosomal escape motif is introduced into the RGD10 peptide-fused light-chain variable region of a conventional therapeutic antibody would merge with intracellular activated H-RAS G12V mutants.

FIG. 30a shows a process of constructing a cytosol-penetrating antibody having a light-chain variable region from which endosomal escape ability has been removed and a heavy-chain variable region into which an improved endosomal 25 escape motif has been introduced. The VH CDR3 of CT/TMab4 (GAYKRGYAMDY, SEQ ID NO: 104), CT01 (GWYWM----DL, SEQ ID NO: 46), CTO2 (GWYWF----DL, SEQ ID NO: 105), CTO3 (GWYWG---MDL, SEQ ID NO: 106), CTO4 (YWYWM----DL, SEQ ID NO: 49).

FIG. 30b shows a graph quantitatively comparing the number of cells that have taken up trypan blue depending on pH by a cytosol-penetrating antibody having a light-chain variable region from which endosomal escape ability is removed and a heavy-chain variable region into which an improved endosomal escape motif is introduced.

FIG. 30c shows the results of confocal microscopy performed to observe the GFP fluorescence by enhanced split-GFP complementation of a GFP11-SBP2-fused cytosol-penetrating antibody having a light-chain variable region from which endosomal escape ability has been removed, and a heavy-chain variable region into which an improved endosomal escape motif has been introduced.

FIG. 30d shows the results of confocal microscopy performed using calcein in order to observe the cytosolic localization of a cytosol-penetrating antibody having a light-chain variable region from which endosomal escape ability has been removed and a heavy-chain variable region into which an improved endosomal escape motif has been introduced.

FIG. 31a is a graph quantitatively comparing the number of cells that taken up trypan blue depending on pH by mutants constructed by substituting the pt amino acid glutamic acid of the heavy-chain variable region (VH) of a cytosol-penetrating antibody, which induces a change in properties of the antibody at acidic pH 5.5, with various amino acids. The VH CDR3 of CT01-AAA (GWYWMDL, SEQ ID NO: 46), CT01-AAA E1A (GWYWMDL, SEQ ID NO: 46), CT01-AAA E1D (GWYWMDL, SEQ ID NO: 46), and CT01-AAA El Q (GWYWMDL, SEQ ID NO: 46) are shown.

FIG. 31b is a graph quantitatively comparing the number of cells that taken up trypan blue depending on pH by mutants constructed by substituting 102nd amino acid leucine of the heavy-chain variable region (VH) of a cytosol-penetrating antibody, which induces a change in properties of the antibody at acidic pH 5.5, with various amino acids. The VH CDR3 of CT01-AAA (GWYWMDL, SEQ ID NO: 46) and CT01-AAA 1102x (GWYWMDX, SEQ ID NO: 107) are shown.

FIG. 32a shows a graph quantitatively comparing the number of cells that have taken up trypan blue depending on pH by intact IgG-format cytosol-penetrating antibodies having a light-chain variable region and/or a heavy-chain variable region introduced with an endosomal escape motif having three tryptophan residues. The VH CDR3 for CT-3 (GAYKRGYAMDY, SEQ ID NO: 104), CT-WWW (GAYKRGYAMDY, SEQ ID NO: 104), CT01-AAA (GWYWM----DL, SEQ ID NO: 46), CTWWW-AAA (GWWWM----DL, SEQ ID NO: 108), CT01-3 (GWYWM----DL, SEQ ID NO: 46), and CTWWW-WWW (GWWWM----DL, SEQ ID NO: 53), and the VL CDR3 of CT-3 (QQYWYWMYT, SEQ ID NO: 9), CT-WWW (QQYWWWMYT, SEQ ID NO: 51), CT01-AAA (QQYAAAMYT, SEQ ID NO: 86), CTWWW-AAA (QQYAAAMYT, SEQ ID NO: 86), CT01-3 (QQYWYWMYT, SEQ ID NO: 9), and CTWWW-WWW (QQYWWWMTY, SEQ ID NO: 122) are shown.

FIG. 32b shows a bar graph showing the results of observing the cytosolic localization of intact IgG-format cytosol-penetrating antibodies having a light-chain variable region and/or a heavy-chain variable region introduced with an endosomal escape motif having three tryptophan residues by confocal microscopy using calcein and quantifying the calcein fluorescence of the confocal micrographs.

FIG. 33a shows a schematic view showing a process of constructing an intact IgG-format cytosol-penetrating antibody in which an improved endosomal escape motif has been introduced into a heavy-chain variable region thereof and an improved endosomal escape motif has been introduced into a light-chain variable region of a conventional therapeutic antibody fused with an EpCAM-targeting peptide.

FIG. 33*b* shows a bar graph showing the results of observing the cytosolic localization of an intact IgG-format cytosol-penetrating antibody, in which an improved endosomal escape motif has been introduced into a heavy-chain variable region thereof and an improved endosomal escape motif has been introduced into a light-chain variable region of a conventional therapeutic antibody fused with an EpCAM-targeting peptide, by confocal microscopy using calcein and quantifying the calcein fluorescence of the confocal micrographs.

FIG. 33*c* shows a graph quantitatively comparing the number of cells that have taken up trypan blue depending on pH by an intact IgG-format cytosol-penetrating antibody in which an improved endosomal escape motif has been introduced into a heavy-chain variable region thereof and an improved endosomal escape motif has been introduced into a light-chain variable region of a conventional therapeutic antibody fused with an EpCAM-targeting peptide.

FIG. 34*a* is a schematic view showing a process of constructing an intact IgG-format cytosol-penetrating antibody in which an improved endosomal escape motif has been introduced into the heavy-chain variable region of a conventional therapeutic antibody.

FIG. 34*b* is a graph quantitatively comparing the number of cells that have taken up trypan blue depending on pH by an intact IgG-format cytosol-penetrating antibody in which an improved endosomal escape motif has been introduced into the heavy-chain variable region of a conventional therapeutic antibody.

FIG. 35 is a graph quantitatively comparing the number of cells that have taken up trypan blue depending on pH by an intact IgG-format cytosol-penetrating antibody comprising a light-chain variable region and/or a heavy-chain variable region introduced with asparaginic acid. The VH CDR1 of CT10 (AASGFTFS[DFSMS], SEQ ID NO: 109), CT11 (AASGFTDD[DFSMS, SEQ ID NO: 111), and CT12 (AASGFTDD[DFSMS], SEQ ID NO: 111), the VH CDR2 of CT10 (YISRTSHTTYYADSVKG, SEQ ID NO: 110), CT11 (YISRTSHTTYYADSVKG, SEQ ID NO: 110), and CT12 (YISRTSHTTDYADSVKG, SEQ ID NO: 112), the VL CDR1 of hT4-59 (KSSQSLLNSRDGKNYLA, SEQ ID NO: 113), hT4-60 (KSSQSDLNSRDGKNYLA, SEQ ID NO: 115), hT4-61 (KSSQSLLNSRDGKNYLA, SEQ ID NO: 113), hT4-62 (KSSQSLLNSRDGKNYLA, SEQ ID NO: 113), and hT4-63 (KSSQSDLNSRDGKNYLA, SEQ ID NO: 115), and the VL CDR2 of hT4-59 (WASTRES, SEQ ID NO: 114), hT4-60 (WASTRES, SEQ ID NO: 114), hT4-61 (DASTRES, SEQ ID NO: 116), hT4-62 (DDSTRES, SEQ ID NO: 117), and hT4-63 (DDSTRES, SEQ ID NO: 117) are shown.

FIG. 36*a* shows the results of observing a crystal of CT-59 Fab, formed under Index G1 conditions, by RI1000 (Rock Imager1000; automatic protein crystal image analysis system).

FIG. 36*b* shows the three-dimensional structure of CT-59 refined and validated using the pymol program. The $1^{st}$ amino acid asparaginic acid (D) and $95^{th}$ amino acid methionine (M) are shown in yellow, and the $92^{nd}$ to $94^{th}$ amino acids are shown in orange.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In one aspect, the present disclosure is directed to a cytosol-penetrating antibody or an antigen-binding fragment thereof comprising a light-chain variable region and/or heavy-chain variable region that comprises a sequence represented by the following formula in its CDR3:

X1-X2-X3-Z1 wherein X1-X2-X3 is an endosomal escape motif, and each of X1, X2 and X3 is selected from the group consisting of tryptophan (W), tyrosine (Y), histidine (H) and phenylalanine (F);

Z1 is selected from the group consisting of methionine (M), isoleucine (I), leucine (L), histidine (H), asparaginic acid (D), and glutamic acid (E);

the light-chain variable region and/or heavy-chain variable region comprising Z1 induces a change in properties of the antibody under endosomal acidic pH conditions; and the antibody exhibits an ability to escape from endosomes into the cytosol through the change in properties of the antibody.

"Endosomal escape" in the present disclosure may mean actively penetrating living cells by endocytosis, and then escaping from endosomes into the cytosol under acidic conditions.

"Endosomal escape motif" in the present disclosure includes a one-dimensional structure comprising a specific amino acid sequence having the property of inducing endosomal escape under acidic conditions, and a three-dimensional structure formed thereby. "Endosomal escape motif" may be used interchangeably with "motif having endosomal escape ability". An antibody comprising a light-chain variable region (VL) or heavy-chain variable region (VH) that comprises an "endosomal escape motif" is capable of "penetrating the cytosol". "Cytosol-penetrating antibody" means that an antibody that penetrated cells by endocytosis escapes from endosomes into the cytosol under acidic conditions. "Cytosol-penetrating antibody" may be used interchangeably with "antibody having cytosol-penetrating ability".

In the present disclosure, Z1 included in the endosomal escape motif X1-X2-X3-Z1 may be located at the $95^{th}$ amino acid of the light-chain variable region or the $102^{nd}$ amino acid of the heavy-chain variable region, as numbered by the Kabat numbering system, and is the hydrophobic amino acid methionine (M), isoleucine (I) or leucine (L), the negatively charged amino acid asparaginic acid (D) or glutamic acid (E), or the positively charged amino acid histidine (H). The 1st amino acid of the light-chain variable region or heavy-chain variable region of the cytosol-penetrating antibody according to the present disclosure can interact with negatively charged asparaginic acid (D) or glutamic acid (E) and Z1, which is the $95^{th}$ amino acid of the light-chain variable region or the $102^{nd}$ amino acid of the heavy-chain variable region, under endosomal acidic pH conditions, thereby inducing a change in the properties of the antibody and allowing the antibody to have the ability to escape from endosomes into the cytosol.

In the present disclosure, the 1st amino acid of the light-chain variable region and/or heavy-chain variable region of the cytosol-penetrating antibody of the cytosol-penetrating antibody or antigen-binding fragment thereof may interact with Z1 under endosomal acidic pH conditions to induce a change in properties of the cytosol-penetrating antibody.

In addition, as pH 7.4 changes to endosomal acidic pH 5.5, the interaction between Z1 of the endosomal escape motif and the 1st amino acid of the light-chain variable region and/or heavy-chain variable region changes. Namely, when Z1 is composed of the hydrophobic amino acid methionine (M), isoleucine (I) or leucine (L) or the negatively charged amino acid asparaginic acid (D) or glutamic acid (E), the carboxylic acid in the side chain of the negatively charged amino acid becomes hydrophobic by partial protonation under the acidic conditions, and thus Z1 hydrophobically interacts with asparaginic acid (D) or glutamic acid (E), which is the 1st amino acid of the light-chain variable region or heavy-chain variable region.

In addition, regarding induction of a pH-dependent change in properties of the antibody by interaction between Z1 of the endosomal escape motif and the 1st amino acid of the light-chain variable region or heavy-chain variable region, when Z1 is composed of the hydrophobic amino acid methionine (M), isoleucine (I) or leucine (L), it does not interact with the negatively charged amino acid asparaginic acid (D) or glutamic acid (E), which is the 1st amino acid of the light-chain variable region or heavy-chain variable region, under neutral pH conditions. However, as pH decreases, the negatively charged amino acid becomes hydrophobic by protonation, and thus hydrophobically interacts with Z1. As a result, the distance between the two amino acids becomes closer, thereby inducing a change in the structure and function of the protein. This phenomenon is known as the Tanford transition.

In addition, when Z1 is composed of histidine (H), as pH changes from 7.4 to 5.5, the net charge of the amino acid side chains becomes positive, and Z1 electrostatically interacts with asparaginic acid (D) or glutamic acid (E), which is the $1^{st}$ amino acid of the light-chain variable region or heavy-chain variable region.

In an example of the present disclosure, in order to confirm whether a pH-dependent change in the properties of the antibody is induced by a pair of the 1st and $95^{th}$ amino acids of the light-chain variable region, endosomal escape ability was analyzed using alanine substitution mutants. As a result, the alanine substitution mutations showed no pH-dependent endosomal escape ability. In addition, endosomal escape ability was analyzed using mutations obtained by substituting the $95^{th}$ amino acid with 20 different amino acids, and as a result, mutants in which the $95^{th}$ amino acid of the light-chain variable region of the cytosol-penetrating antibody according to the present disclosure is composed of methionine (M), leucine (L), isoleucine (I), asparaginic acid (D), glutamic acid (E) and histidine (H) showed pH-dependent endosomal escape ability.

In an example of the present disclosure, regarding a pair of the $1^{st}$ and $102^{th}$ amino acids of the heavy-chain variable region, which induces a pH-dependent change in the properties of the antibody, which has been found through the alanine substitution mutation experiment in the same manner as that in the above example, endosomal escape ability was analyzed using mutations obtained by substituting the 102th amino acid with 13 different amino acids, and as a result, mutants in which the $102^{th}$ amino acid of the heavy-chain variable region of the cytosol-penetrating antibody according to the present disclosure is composed of methionine (M), leucine (L), isoleucine (I), asparaginic acid (D), glutamic acid (E) and histidine (H) showed pH-dependent endosomal escape ability.

In addition, in one embodiment of the present disclosure, the cytosol-penetrating antibody may further comprise, between X3 and Z1, an amino acid sequence represented by (a1- . . . -an) (where n is an integer ranging from 1 to 10). In one embodiment of the present disclosure, when the cytosol-penetrating antibody further comprises, between X3 and Z1, an amino acid sequence represented by (a1- . . . -an) (where n is an integer ranging from 1 to 10), a change in the properties of the endosomal escape motif can be promoted while the length of the CDR3 increases.

In the present disclosure, the endosomal escape motif has a structure of X1-X2-X3-Z1 included in the light-chain variable region; the heavy-chain variable region; or the light-chain variable region and heavy-chain variable region, and each of X1, X2 and X3 is selected from the group consisting of tryptophan (W), tyrosine (Y), histidine (H) and phenylalanine (F).

In the present disclosure, the endosomal escape motif X1-X2-X3 can react at intracellular endosomal weakly acidic pH, for example, a pH of 5.5 to 6.5, which is early endosomal pH, and thus Z1 can interact with the 1st amino acid of the light-chain variable region or heavy-chain variable region, thereby changing the properties of the antibody and significantly increasing the endosomal escape efficiency of the antibody.

In the present disclosure, the endosomal escape motif X1, X2 and X3 are selected from the group consisting of amino acids that easily interact with the hydrophilic head portion and hydrophobic tail portion of 1-palmitoyl-2-oleoyl-sn-glycero-3-phosphatidylcholine (POPC) which is the major phospholipid component of the inner endosomal membrane.

Specifically, the average binding activity of 20 different amino acids for 1-palmitoyl-2-oleoyl-sn-glycero-3-phosphatidylcholine (POPC) is higher in the order of tryptophan (W), phenylalanine (F), tyrosine (Y), leucine (L), isoleucine (I), cysteine (C), and methionine (M).

Specifically, the binding activity of 20 different amino acids for the hydrophilic head portion of 1-palmitoyl-2-oleoyl-sn-glycero-3-phosphatidylcholine (POPC) is higher in the order of arginine (R), tryptophan (W), tyrosine (Y), histidine (H), asparagine (N), glutamine (Q), lysine (K), and phenylalanine (F). In addition, the binding activity of 20 different amino acids for the hydrophobic head portion of 1-palmitoyl-2-oleoyl-sn-glycero-3-phosphatidylcholine (POPC) is higher in the order of tryptophan (W), phenylalanine (F), leucine (L), methionine (M), isoleucine (I), valine (V), and tyrosine (Y).

In the present disclosure, amino acids constituting X1, X2 and X3 of the endosomal escape motif may include tyrosine (Y) and histidine (H), which constitute a wild-type cytosol-penetrating antibody. Thus, these amino acids may include tryptophan (W) and phenylalanine (F), which have a higher average binding affinity than tyrosine (Y) for 1-palmitoyl-2-oleoyl-sn-glycero-3-phosphatidylcholine (POPC).

In an example of the present disclosure, amino acids that easily interact with 1-palmitoyl-2-oleoyl-sn-glycero-3-phosphatidylcholine (POPC) was examined through literature search. Furthermore, tryptophan (W) having high binding affinity for the hydrophilic head portion and hydrophobic tail portion was introduced into X1, X2 and X3 of the endosomal escape motif, and endosomal escape ability was analyzed. As a result, an improved cytosol-penetrating antibody according to the present disclosure showed a higher pH-dependent endosomal escape ability than the wild-type cytosol-penetrating antibody including tyrosine (Y), tyrosine (Y) and histidine (H) in X1, X2 and X3, respectively.

In another example, in order to examine whether interaction with the head portion or tail portion of 1-palmitoyl-2-oleoyl-sn-glycero-3-phosphatidylcholine (POPC) is important for endosomal escape, mutants were constructed by introducing arginine (R) which easily binds only to the head portion, isoleucine (I) which easily binds only to the tail portion, and glycine (G) which shows significantly low interaction with the lipid, into X1, X2 and X3 of the endosomal escape motif, and endosomal escape ability was analyzed. As a result, two mutants, excluding a cytosol-penetrating antibody introduced with tryptophan (W) according to the present disclosure, all showed significantly reduced endosomal escape ability. This suggests that interactions with the hydrophilic head and hydrophobic tail of the lipid are all involved in endosomal escape.

In still another example, the endosomal escape motif of the light-chain variable region may comprise one or more tryptophans, or one or two tryptophans.

In order to increase the effect of a substance that exhibits its activity in the cytosol, the amount of the substance located in the cytosol should ultimately increase. Hence, studies have been conducted to increase endosomal escape ability. Such studies have been conducted mainly on cell-penetrating peptides (CPPs). In particular, interaction with the lipid membrane is essential for passage through the cell lipid membrane, a strategy for enhancing this interaction has been introduced. As one example, tryptophan was added to the N-terminus of a cytosol-penetrating peptide rich in arginine and to the middle portion of the peptide.

However, this approach has not been attempted on antibodies. Tryptophan (W) is an amino acid showing high interaction with the hydrophilic head portion and hydrophobic tail portion of 1-palmitoyl-2-oleoyl-sn-glycero-3-phosphatidylcholine (POPC) which is the major phospholipid component of the cell membrane. Thus, it can improve interaction with the inner endosomal membrane and induce endosomal escape.

Specifically, in an example of the present disclosure, the endosomal escape motif X1-X2-X3 of the light-chain variable region and/or heavy-chain variable region may comprise a sequence selected from the group consisting of W-W-W, W-W-H, W-Y-W, Y-W-W, W-Y-H, and Y-W-H (where W is tryptophan, Y is tyrosine, H is histidine).

In an example of the present disclosure, it was found that the endosomal escape motif X1-X2-X3 of the light-chain variable region and/or heavy-chain variable region increases the endosomal escape ability through a change in the properties of the antibody by induction of the interaction under endosomal acidic pH conditions.

As used herein, the term "endosomal acidic pH" refers to a pH range of 6.0 to 4.5, which satisfies early endosomal and late endosomal pH conditions and in which the side-chain properties of asparaginic acid (D) and glutamic acid (E) may change.

The CDR1 of the light-chain variable region comprising the endosomal escape motif may comprise one or more sequences selected from the following group consisting of:

QQYWWHMYT; (SEQ ID NO: 8)

QQYWYWMYT; (SEQ ID NO: 9)

QQYYWWMYT; (SEQ ID NO: 10)

QQYWYHMYT; (SEQ ID NO: 11)

QQYYWHMYT; (SEQ ID NO: 12)
and

QQYWWWMYT. (SEQ ID NO: 51)

The light-chain variable region comprising the endosomal escape motif may comprise a sequence having a homolog of at least 80%, for example, 85%, 90%, 95%, 96%, 97%, 98%, 99% or 100%, to a light-chain variable region sequence selected from the group consisting of, for example, SEQ ID NOS: 1 to 5, 13 to 23, 25 to 37, 50, and 60 to 64.

Improved endosomal escape efficiency can also be achieved at the same level even when the endosomal escape motif is included in the heavy-chain variable region.

Specifically, the heavy-chain variable region may include X1-X2-X3-Z1 (wherein each of X1, X2 and X3 is selected from the group consisting of tryptophan (W), tyrosine (Y), histidine (H) and phenylalanine (F)) in its CDR3, and Z1 can interact with the $1^{st}$ amino acid of the heavy-chain variable region under endosomal acidic pH conditions, thus changing the properties of the cytosol-penetrating antibody and enabling the antibody to have the ability to escape from endosomes into the cytosol.

The CDR3 of the heavy-chain variable region comprising the endosomal escape motif may comprise one or more sequences selected from the following group consisting of SEQ ID NOS: 46 to 49, and 53:

GWYWMDL; (SEQ ID NO: 46)

GWYWFDL; (SEQ ID NO: 47)

GWYWGFDL; (SEQ ID NO: 48)

YWYWMDL; (SEQ ID NO: 49)
and

GWWWMDL. (SEQ ID NO: 53)

the light-chain variable region comprise a sequence having a homolog of at least 80% to a light-chain variable region sequence selected from the group consisting of SEQ ID NOS: 1 to 5, 13 to 23, 25 to 37, 50, and 60 to 64.

The heavy-chain variable region comprising the endosomal escape motif may comprise a sequence having a homolog of at least 80%, for example, 85%, 90%, 95%, 96%, 97%, 98%, 99% or 100%, to a heavy-chain variable region sequence selected from the group consisting of, for example, SEQ ID NOS: 39 to 42, 52, and 54 to 59.

In addition, in one embodiment, the sequence may further comprise Z2 linked to X1, and thus may be represented by the following formula:

Z2-X1-X2-X3-Z1, wherein Z2 is selected from the group consisting of glutamine (Q), leucine (L) histidine (H).

As described above, the sequence is represented by Z2-X1-X2-X3-Z1, the $1^{st}$ amino acid of the light-chain variable region and/or heavy-chain variable region interacts with Z1 and/or Z2 to induce pH-dependent endosomal escape under endosomal acidic pH conditions.

The CDR1 of the light-chain variable region comprising the endosomal escape motif may comprise a sequences of SEQ ID NO: 24 as set forth below:

(SEQ ID NO: 24)
QHYWYWMYT.

As used herein, "antibody" is meant to include an intact antibody form that specifically binds to a target as well as an antigen-binding fragment of the antibody.

The complete antibody is a structure having two full-length light chains and two full-length heavy chains, and each light chain is linked by a disulfide bond with a heavy chain. A constant region of the heavy chain has gamma (γ), mu (μ), alpha (α), delta (δ), and epsilon (ε) types. Sub-classes have gamma 1 (γ1), gamma 2 (γ2), gamma 3 (γ3), gamma 4 (γ4), alpha (α1), and alpha 2 (α2) types. A constant region of the light chain has kappa (κ) and lambda (λ) types.

An antigen binding fragment or an antibody fragment of an antibody refers to a fragment having an antigen binding function and includes Fab, F(ab'), F(ab')$_2$, Fv, and the like. Fab of the antibody fragments has a structure including variable regions of a light chain and a heavy chain, a constant region of the light chain, and a first constant region (CH1 domain) of the heavy chain with one antigen-binding site. Fab' differs from Fab in that it has a hinge region containing one or more cysteine residues at the C-terminal of the heavy chain CH1 domain. The F(ab')2 antibody is produced when the cysteine residue of the hinge region of the Fab' forms a disulfide bond. Recombinant techniques for generating Fv fragments with minimal antibody fragments having only a heavy-chain variable region and a light-chain variable region are described in PCT International Publication Nos. WO88/001649, WO88/006630, WO88/07085, WO88/07086, and WO88/09344. A two-chain Fv has a non-covalent bonding between a heavy-chain variable region and a light-chain variable region. A single chain Fv (scFv) is connected to a heavy-chain variable region and a light-chain variable region via a peptide linker by a covalent bond or directly at the C-terminal. Thus, the single chain Fv (scFv) has a structure such as a dimer like the two-chain Fv. Such an antibody fragment can be obtained using a protein hydrolyzing enzyme (for example, when the whole antibody is cleaved with papain, Fab can be obtained, and when whole antibody is cut with pepsin, F(ab')2 fragment can be obtained), and it can also be produced through gene recombinant technology.

In one embodiment, the antibody according to the present disclosure may be an Fv form (e.g., scFv) or a whole antibody form. The cytosol-penetrating antibody according to the present disclosure may be an IgG, IgM, IgA, IgD or IgE type. For example, it may be an IgG1, IgG2, IgG3, IgG4, IgM, IgE, IgA1, IgA5, or IgD type. Most preferably, it may be an intact IgG-format monoclonal antibody.

Further, the heavy chain constant region can be selected from any one isotype of gamma (γ), mu (μ), alpha (α), delta (δ), and epsilon (ε). Sub-classes have gamma 1 (γ1), gamma 2 (γ2), gamma 3 (γ3), gamma 4 (γ4), alpha 1 (α1), and alpha 2 (α2) types. A constant region of the light chain has kappa (κ) and lambda (λ) types.

The term "heavy chain" as used herein refers to a full-length heavy chain and fragments thereof including a variable region domain VH including an amino acid sequence with sufficient variable region sequence to confer specificity to an antigen and three constant region domains CH1, CH2, and CH3. The term "light chain" as used herein refers to a full-length heavy chain and fragments thereof including a variable region domain VL including an amino acid sequence with sufficient variable region sequence to confer specificity to an antigen and a constant region domain CL.

In the present disclosure, the antibody includes monoclonal antibodies, multispecific antibodies, human antibodies, humanized antibodies, chimeric antibodies, single-chain Fvs (scFV), single chain antibodies, Fab fragments, F(ab') fragments, disulfide-linked Fvs (sdFV) and anti-idiotype (anti-Id) antibodies, and epitope-binding fragments of these antibodies, but is not limited thereto.

An "Fv" fragment is an antibody fragment that contains complete antigen recognition and binding sites. Such region includes a heavy chain variable domain and a light chain variable domain, for example, dimers substantially tightly covalently associated with scFv.

"Fab" fragment contains the variable and constant domain of the light-chain and the variable and first constant domain (CH1) of the heavy chain. F(ab')2 antibody fragment generally includes a pair of Fab fragments covalently linked by hinge cysteine near their carboxy-terminus.

"Single chain Fv" or "scFv" antibody fragment comprises VH and VL domains of the antibody. Such domains are within a single polypeptide chain. The Fv polypeptide may further include a polypeptide linker between the VH domain and the VL domain such that the scFv can form the desired structure for antigen binding.

The monoclonal antibody refers to an antibody obtained from a substantially homogeneous population of antibodies, i.e., the same except for possible naturally occurring mutations that may be present in trace amounts of individual antibodies that occupy the population. The monoclonal antibody is highly specific and is derived against a single antigenic site.

The non-human (e.g. murine) antibody of the "humanized" form is a chimeric antibody containing minimal sequence derived from non-human immunoglobulin. In most cases, the humanized antibody is a human immunoglobulin (receptor antibody) that has been replaced by a residue from the hypervariable region of a non-human species (donor antibody), such as a mouse, rat, rabbit, and non-human primate, having specificity, affinity, and ability to retain a residue from the hypervariable region of the receptor.

"Human antibody" is a molecule derived from human immunoglobulin and means that all of the amino acid sequences constituting the antibody including the complementarity determining region and the structural region are composed of human immunoglobulin.

A heavy chain and/or light chain is partly identical or homologous to the corresponding sequence in an antibody derived from a particular species or belonging to a particular antibody class or subclass, while the remaining chain(s) are identical or homologous to corresponding sequences in an antibody derived from another species or belonging to another antibody class or subclass "chimeric" antibodies (immunoglobulins) as well as a fragment of such antibody exhibiting the desired biological activity.

"Antibody variable domain" as used herein refers to the light and heavy chain regions of an antibody molecule including the amino acid sequences of a complementarity determining region (CDR; i.e., CDR1, CDR2, and CDR3) and a framework region (FR). VH refers to a variable domain of the heavy chain. VL refers to a variable domain of the light chain.

"Complementarity determining region" (CDR; i.e., CDR1, CDR2, and CDR3) refers to the amino acid residue of the antibody variable domain, which is necessary for antigen binding. Each variable domain typically has three CDR regions identified as CDR1, CDR2, and CDR3.

"Framework region" (FR) is a variable domain residue other than a CDR residue. Each variable domain typically has four FRs identified as FR1, FR2, FR3, and FR4.

In another aspect, the present disclosure is directed to a composition for delivering an active substance into cytosol, comprising the cytosol-penetrating antibody or antigen binding fragment thereof.

The active substance may be a type fused or bonded to the antibody, and the active substance may be one or more selected from the group consisting of, for example, peptides, proteins, toxins, antibodies, antibody fragments, RNAs, siRNAs, DNAs, small molecule drugs, nanoparticles, and liposomes, but is not limited thereto.

The proteins may be antibodies, antibody fragments, immuoglubulin, peptides, enzymes, growth factors, cytokines, transcription factors, toxins, antigen peptides, hormones, carrier proteins, motor function proteins, receptors, signaling proteins, storage proteins, membrane proteins, transmembrane proteins, internal proteins, external proteins, secretory proteins, viral proteins, glycoproteins, cleaved proteins, protein complexes, chemically modified proteins, or the like.

The RNA or ribonucleic acid is based on ribose, a kind of pentose, is a kind of nucleic acid consisting of a chain of nucleotides, has a single-stranded structure, and is formed by transcription of a portion of DNA. In one embodiment, the RNA may be selected from the group consisting of rRNA, mRNA, tRNA, miRNA, snRNA, snoRNA, and aRNA, but is not limited thereto.

The siRNA (Small interfering RNA) is a small RNA interference molecule composed of dsRNA, and functions to bind to and degrade an mRNA having a target sequence. It is used as a disease treating agent or has an activity of inhibiting expression of a protein translated from a target mRNA by degrading the target mRNA. Due to this activity, it is widely used herein.

The DNA or deoxyribonucleic acid is a kind of nucleic acid, is composed of a backbone chain comprising monosaccharide deoxyribose linked by phosphate, together with two types of nucleobases (purines and pyrimidines), and stores the genetic information of cells.

As used herein, the term "small-molecule drugs" refers to organic compounds, inorganic compounds or organometallic compounds that have a molecular weight of less than about 1000 Da and are active as therapeutic agents against diseases. The term is used in a broad sense herein. The small-molecule drugs herein encompass oligopeptides and other biomolecules having a molecular weight of less than about 1000 Da.

In the present disclosure, a nanoparticle refers to a particle including substances ranging between 1 and 1,000 nm in diameter. The nanoparticle may be a metal nanoparticle, a metal/metal core shell complex consisting of a metal nanoparticle core and a metal shell enclosing the core, a metal/non-metal core shell consisting of a metal nanoparticle core and a non-metal shell enclosing the core, or a non-metal/metal core shell complex consisting of a non-metal nanoparticle core and a metal shell enclosing the core. According to an embodiment, the metal may be selected from gold, silver, copper, aluminum, nickel, palladium, platinum, magnetic iron and oxides thereof, but is not limited thereto, and the non-metal may be selected from silica, polystyrene, latex and acrylate type substances, but is not limited thereto.

In the present disclosure, liposomes include at least one lipid bilayer enclosing the inner aqueous compartment, which is capable of being associated by itself. Liposomes may be characterized by membrane type and size thereof. Small unilamellar vesicles (SUVs) may have a single membrane and may range between 20 and 50 nm in diameter. Large unilamellar vesicles (LUVs) may be at least 50 nm in diameter. Oliglamellar large vesicles and multilamellar large vesicles may have multiple, usually concentric, membrane layers and may be at least 100 nm in diameter. Liposomes with several nonconcentric membranes, i.e., several small vesicles contained within a larger vesicle, are referred to as multivesicular vesicles.

The term "fusion" or "binding" refers to unifying two molecules having the same or different function or structure, and the methods of fusing may include any physical, chemical or biological method capable of binding the tumor tissue-penetrating peptide to the protein, small-molecule drug, nanoparticle or liposome. Preferably, the fusion may be made by a linker peptide, and for example, the linker peptide may mediate the fusion with the bioactive molecules at various locations of an antibody light-chain variable region of the present disclosure, an antibody, or fragments thereof.

In still another aspect, the present disclosure provides a pharmaceutical composition for prevention or treatment of cancer, comprising: the above-described cytosol-penetrating antibody or antigen binding fragment thereof; and an active substance to be delivered into cytosol by the cytosol-penetrating antibody or antigen binding fragment thereof.

The use of the active substance can impart the property of penetrating cells and localizing in the cytosol, without affecting the high specificity and affinity of antibodies for antigens, and thus can localize in the cytosol which is currently classified as a target in disease treatment based on small-molecule drugs, and at the same time, can exhibit high effects on the treatment and diagnosis of tumor and disease-related factors that show structurally complex interactions through a wide and flat surface between protein and protein.

The use of the pharmaceutical composition for prevention or treatment of cancer can impart the property of enabling the antibody to penetrate cells and remain in the cytosol, without affecting the high specificity and affinity of the antibody for antigens, and thus the antibody can localize in the cytosol which is currently classified as a target in disease treatment based on small-molecule drugs, and at the same time, can be expected to exhibit high effects on the treatment and diagnosis of tumor and disease-related factors that show structurally complex interactions through a wide and flat surface between protein and protein.

In one example of the present disclosure, the pharmaceutical composition can selectively inhibit KRas mutants, which are major drug resistance-associated factors in the use of various conventional tumor therapeutic agents, and at the same time, can be used in combination with conventional therapeutic agents to thereby exhibit effective anticancer activity.

The cancer may be selected from the group consisting of squamous cell carcinoma, small cell lung cancer, non-small cell lung cancer, adenocarcinoma of lung, squamous cell carcinoma of lung, peritoneal cancer, skin cancer, skin or ocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatoma, gastrointestinal cancer, pancreatic cancer, glioblastoma, cervical cancer, ovarian cancer, liver cancer, bladder cancer, liver tumor, breast cancer, colon cancer, colorectal cancer, endometrial cancer or uterine cancer, salivary gland cancer, kidney cancer, liver cancer, prostate cancer, vulva cancer, thyroid cancer, liver cancer and head and neck cancer.

When the composition is prepared as a pharmaceutical composition for preventing or treating cancer or angiogenesis-related diseases, the composition may include a pharmaceutically acceptable carrier. The pharmaceutically acceptable carrier contained in the composition is typically used in the formulation. Examples of the pharmaceutically acceptable carrier included in the composition may include, but are not limited to, lactose, dextrose, sucrose, sorbitol, mannitol, starch, acacia rubber, calcium phosphate, alginate, gelatin, calcium silicate, minute crystalline cellulose, polyvinyl pyrrolidone, cellulose, water, syrup, methyl cellulose, methyl hydroxy benzoate, propyl hydroxy benzoate, talc, magnesium stearate and mineral oil, etc., but are not limited thereto. In addition to the above ingredients, the pharmaceutical composition may further include a lubricant, a wetting agent, a sweetener, a flavoring agent, an emulsifier, a suspension, a preservative, etc.

The pharmaceutical composition for preventing or treating cancer or angiogenesis-related diseases may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration is formulated to coat an active substance or to be protected against degradation in stomach. Also, the pharmaceutical composition may be administered by any device which can transport active substances to target cells.

Proper dose of the pharmaceutical composition for preventing or treating cancer or angiogenesis-related diseases may vary according to various factors such as method for formulating, administration method, age, weight, gender, pathological state of patient, food, administration time, administration route, excretion rate and reaction sensitivity, etc. Preferably, a proper dose of the composition is within the range of 0.001 and 100 mg/kg based on an adult. The term "pharmaceutically effective dose" as used herein refers to an amount sufficient to prevent or treat cancer or angiogenesis-related diseases.

The composition may be formulated with pharmaceutically acceptable carriers and/or excipients according to a method that can be easily carried out by those skilled in the art, and may be provided in a unit-dose form or enclosed in a multiple-dose vial. Here, the formulation of the pharmaceutical composition may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents, and may be administered sequentially or simultaneously with conventional therapeutic agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

In yet another aspect, the present disclosure is directed to a pharmaceutical composition for diagnosis of cancer, comprising: the above-described cytosol-penetrating antibody or antigen binding fragment thereof; and an active substance to be delivered into cytosol by the cytosol-penetrating antibody or antigen binding fragment thereof.

The term "diagnosis" as used herein refers to demonstrating the presence or characteristic of a pathophysiological condition. Diagnosing in the present disclosure refers to demonstrating the onset and progress of cancer.

The intact immunoglobulin-format antibody and a fragment thereof may bind to a fluorescent substance for molecular imaging in order to diagnose cancer through images.

The fluorescent substance for molecular imaging refers to all substances generating fluorescence. Preferably, red or near-infrared fluorescence is emitted, and more preferably, a fluorescence with high quantum yield is emitted. However, the fluorescence is not limited thereto.

Preferably, the fluorescent substance for molecular imaging is a fluorescent substance, a fluorescent protein or other substances for imaging, which may bind to the tumor tissue-penetrating peptide that specifically binds to the intact immunoglobulin-format antibody and a fragment thereof, but is not limited thereto.

Preferably, the fluorescent substance is fluorescein, BODYPY, tetramethylrhodamine, Alexa, cyanine, allopicocyanine, or a derivative thereof, but is not limited thereto.

Preferably, the fluorescent protein is Dronpa protein, enhanced green fluorescence protein (EGFP), red fluorescent protein (DsRFP), Cy5.5, which is a cyanine fluorescent substance presenting near-infrared fluorescence, or other fluorescent proteins, but is not limited thereto.

Preferably, other substances for imaging are ferric oxide, radioactive isotope, etc., but are not limited thereto, and they may be applied to imaging equipment such as MR, PET.

In a further another aspect, the present disclosure is directed to a nucleic acid encoding the above-described antibody or antigen-binding fragment thereof.

The nucleic acid is a polynucleotide, and the term "polynucleotide" as used herein refers to a deoxyribonucleotide or ribonucleotide polymer present in a single-stranded or double-stranded form. It includes RNA genome sequence, DNA (gDNA and cDNA), and RNA sequence transcribed therefrom. Unless otherwise described, it also includes an analog of the natural polynucleotide.

The polynucleotide includes not only a nucleotide sequence encoding the above-described light-chain variable region (VL) and heavy-chain variable region (VH) having improved endosomal escape ability, but also a complementary sequence thereto. The complementary sequence includes a sequence fully complementary to the nucleotide sequence and a sequence substantially complementary to the nucleotide sequence. For example, this complementary sequence may include a sequence that may be hybridized with a nucleotide sequence encoding a light-chain variable region (VL) and heavy-chain variable region (VH) having any one sequence selected from the group consisting of SEQ ID NOS: 1 to 5, 13 to 23, 25 to 37, 50, and 60 to 64, and SEQ ID NOS: 39 to 42, 52, and 54 to 59 under stringent conditions known in the pertinent art.

The polynucleotide includes not only a nucleotide sequence encoding the above-described light-chain region (kds), but also a complementary sequence thereto. The complementary sequence includes a sequence fully complementary to the nucleotide sequence and a sequence substantially complementary to the nucleotide sequence. For example, this means a sequence that may be hybridized with a nucleotide sequence encoding an amino acid sequence of any one of SEQ ID NO:1 to SEQ ID NO: 3 under stringent conditions known in the pertinent art.

The nucleic acid may be modified. The modification includes the addition, deletion, or non-conservative substitution or conservative substitution of nucleotides. The nucleic acid encoding the amino acid sequence is interpreted to include a nucleotide sequence that has a substantial identity to the nucleotide sequence. The substantial identity may refer to a sequence having a homology of at least 80%, a homology of at least 90%, or a homology of at least 95% when aligning the nucleotide sequence to correspond to any other sequence as much as possible and analyzing the aligned sequence using an algorithm generally used in the pertinent art.

The DNA encoding the antibody can be easily separated or synthesized using conventional procedures (for example, using an oligonucleotide probe capable of specifically binding to DNA encoding the heavy chain and the light chain of the antibody).

In a still further aspect, the present disclosure is directed to a method for producing the above-described cytosol-penetrating antibody or antigen binding fragment thereof, comprising a step of grafting the endosomal escape motif X1-X2-X3-Z1 (wherein X1-X2-X3 is selected from the group consisting of tryptophan (W), tyrosine (Y), histidine (H), and phenylalanine (F)) into the CDR3 of a light chain and/or heavy-chain variable region.

The present disclosure can provide an antibody or antigen-binding fragment thereof having a cytosol-penetrating ability by substituting the light-chain variable region (VL) of a conventional antibody with a light-chain variable region (VL) having improved endosomal escape ability and substituting the heavy-chain variable region (VH) of the conventional antibody with a heavy-chain variable region (VH) having improved endosomal escape ability.

In one embodiment, a method of producing an intact immunoglobulin-format antibody, which penetrates cells and localizes in the cytosol, by use of a cytosol-penetrating light-chain variable region (VL) having improved endosomal escape ability and a cytosol-penetrating heavy-chain variable region having endosomal escape ability, comprises the steps of: obtaining a nucleic acid, in which a light-chain variable region (VL) in a light chain comprising the light-chain variable region (VL) and a light chain constant region is substituted with a light-chain variable region (VL) having endosomal escape ability or a heavy-chain variable region (VH) and a heavy chain constant region (CH) are substituted with a heavy-chain variable region (VH) having endosomal escape ability, cloning the nucleic acid into a vector, and transforming the vector into a host cell to express the antibody or an antigen binding fragment thereof; and recovering the expressed antibody or an antigen binding fragment thereof.

The above-described method makes it possible to produce an intact immunoglobulin-format antibody having increased endosomal escape ability and cytosol-penetrating ability. Furthermore, transformation with a vector expressing a heavy chain comprising a heavy-chain variable region capable of recognizing a specific protein in cells makes it possible to express an antibody which is able to penetrate cells and localize in the cytosol to bind to the specific protein. The vector may be either a vector system that co-expresses the heavy chain and the light chain in a single vector or a vector system that expresses the heavy chain and the light chain in separate vectors. In the latter case, the two vectors may be introduced into a host cell by co-transformation and targeted transformation.

In the present disclosure, the vector may be either a vector system that co-expresses the heavy chain and the light chain in a single vector or a vector system that expresses the heavy chain and the light chain in separate vectors. In the latter case, the two vectors may be introduced into a host cell by co-transformation and targeted transformation.

The term "vector" as used herein refers to a means for expressing a target gene in a host cell. For example, the vector may include plasmid vector, cosmid vector, bacteriophage vector, and virus vectors such as adenovirus vector, retrovirus vector, and adeno-associated virus vector. The vector that may be used as the recombinant vector may be produced by operating plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4λB, λ-Charon, λΔz1 and M13, etc.), or virus (for example, CMV, SV40, etc.) commonly used in the pertinent art.

The light-chain variable region, the light-chain constant region (CL), the heavy-chain variable region (VH), and the heavy-chain constant region (CH1-hinge-CH2-CH3) of the present disclosure in the recombinant vector may be operatively linked to a promoter. The term "operatively linked" as used herein means a functional linkage between a nucleotide expression control sequence (such as a promoter sequence) and a second nucleotide sequence. Accordingly, the control sequence may control the transcription and/or translation of the second nucleotide sequence.

The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art.

The recombinant vector may be constructed to be a vector that employs a prokaryotic cell or an eukaryotic cell as a host. For example, when the vector used is an expression vector and employs a prokaryotic cell as a host, the vector generally includes a strong promoter which may promote transcription (for example, pLA promoter, trp promoter, lac promoter, tac promoter, T7 promoter, etc.), a ribosome binding site for initiation of translation, and termination sequences for transcription/translation. When the vector employs an eukaryotic cell as a host, a replication origin operating in the eukaryotic cell included in the vector may include an f1 replication origin, an SV40 replication origin, a pMB1 replication origin, an adeno replication origin, an AAV replication origin, a CMV replication origin and a BBV replication origin, etc., but is not limited thereto. In addition, a promoter derived from a genome of a mammal cell (for example, a metalthionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence.

Another aspect of the present disclosure provides a host cell transformed with the recombinant vector.

Any kind of host cell known in the pertinent art may be used as a host cell. Examples of a prokaryotic cell include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus* and *Bascillus thuringiensis, Salmonella typhimurium*, intestinal flora and strains such as *Serratia marcescens* and various *Pseudomonas* Spp., etc. In addition, when the vector is transformed in an eukaryotic cell, a host cell such as yeast (*Saccharomyce cerevisiae*), an insect cell, a plant cell, and an animal cell, for example, SP2/0, CHO (Chinese hamster ovary) K1, CHO DG44, PER.C6, W138, BHK, COS-7, 293, HepG2, Huh7, 3T3, RN, and MDCK cell line, etc., may be used.

Another aspect of the present disclosure may provide a method for producing an intact immunoglobulin-format antibody that penetrates cells and localizes in the cytosol, the method comprising a step of culturing the above-described host cell.

A recombinant vector may be inserted into a host cell using an insertion method well known in the pertinent art. For example, when a host cell is a prokaryotic cell, the transfer may be carried out according to $CaCl_2$ method or an electroporation method, etc., and when a host cell is an eukaryotic cell, the vector may be transferred into a host cell according to a microscope injection method, calcium phosphate precipitation method, an electroporation method, a liposome-mediated transformation method, and a gene bombardment method, etc., but the transferring method is not limited thereto. When using microorganisms such as *E. coli*, etc. the productivity is higher than using animal cells. However, although it is not suitable for production of intact Ig form of antibodies due to glycosylation, it may be used for production of antigen binding fragments such as Fab and Fv.

The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

EXAMPLES

Hereinafter, the present disclosure will be described in further detail with reference to examples. It will be obvious to a person having ordinary skill in the art that these examples are illustrative purposes only and are not to be construed to limit or change the scope of the present disclosure.

Example 1: Expression and Purification of Cytosol-Penetrating Antibody (Cytotransmab)

In order to elucidate the endosomal escape mechanism of a cytosol-penetrating antibody and to improve the endosomal escape mechanism, the cytosol-penetrating antibody was purified.

Specifically, in order to construct a heavy-chain expression vector for producing an intact IgG-format monoclonal antibody, a DNA encoding a heavy chain comprising an antibody heavy-chain variable region (humanized hT0 VH; SEQ ID NO: 38) and a heavy-chain constant region (CH1-hinge-CH2-CH3), which has a secretion signal peptide-encoding DNA fused to the 5' end, was cloned into a pcDNA3.4 vector (Invitrogen) by NotI/HindIII.

Furthermore, in order to construct a vector that expresses a light chain, a DNA encoding a light chain comprising a cytosol-penetrating light-chain variable region (hT4 VL; SEQ ID NO: 65) and light-chain constant region (CL), which has a secretion signal peptide-encoding DNA fused to the 5' end, was cloned into a pcDNA3.4 vector (Invitrogen) by use of NotI/HindIII.

The light-chain and heavy-chain expression vectors were transiently transfected, and the proteins were expressed and purified. In a shaking flask, HEK293-F cells suspension-growing in serum-free FreeStyle 293 expression medium (Invitrogen) were transfected with a mixture of plasmid and polyethylenimine (PEI) (Polyscience). After 200 mL transfection in a shaking flask (Corning), HEK293-F cells were seeded into 100 ml of medium at a density of $2.0 \times 10^6$ cells/ml, and cultured at 150 rpm and in 8% $CO_2$. To produce each monoclonal antibody, a suitable heavy-chain and light-chain plasmid were diluted in 10 ml of FreeStyle 293 expression medium (Invitrogen) (125 μg heavy chain, 125 μg light chain, a total of 250 μg (2.5 μg/ml)), and the dilution was mixed with 10 ml of medium containing 750 μg (7.5 μg/ml) of PEI, and the mixture was incubated at room temperature for 10 minutes. The incubated medium mixture was added to 100 ml of the seeded cell culture which was then cultured at 150 rpm in 8% $CO_2$ for 4 hours, after which 100 ml of FreeStyle 293 expression was added to the cell culture, followed by culture for 6 days.

In accordance with the standard protocol, the protein was purified from the collected cell culture supernatant. The antibody was applied to a Protein A Sepharose column (GE Healthcare), and washed with PBS (pH 7.4). The antibody was eluted using 0.1 M glycine buffer (pH 3.0), and then immediately neutralized with 1M Tris buffer. The eluted antibody fraction was concentrated while the buffer was replaced with PBS (pH 7.4) by dialysis. The purified protein was quantified by measuring the absorbance at 280 nm and the absorption coefficient.

Example 2: Observation of Trafficking after Endocytosis of Cytosol-Penetrating Antibody Trafficking from endocytosis of the developed cytosol-penetrating antibody to localization into the cytosol was observed. This may be an important clue to the mechanism of endosomal escape into the cytosol.

FIG. 1 shows of a pulse-chase experiment and confocal microscopy observation performed to observe the transport process and stability of the cytosol-penetrating antibody (cytotransmab) TMab4 or cell-penetrating peptide TAT introduced into cells.

Specifically, a cover slip was added to 24-well plates, and $2.5 \times 10^4$ HeLa cells per well were added to 0.5 ml of 10% FBS-containing medium and cultured for 12 hours under the conditions of 5% $CO_2$ and 37° C. When the cells were stabilized, the cells were transiently transfected with pcDNA3.4-flag-rab11. To maximize the efficiency of transient transfection, Opti-MEM media (Gibco) was used. 500 ng of pcDNA3.4-flag-rab11 to be transiently transfected was incubated with μl of Opti-MEM media and 2 μl of Lipofectamine 2000 (Invitrogen, USA) in a tube at room temperature for 20 minutes, and then added to each well. Additionally, 450 µl of antibiotic-free DMEM medium was added to each well which was then incubated at 37° C. in 5% $CO_2$ for 6 hours, after which the medium was replaced with 500 µl of 10% FBS-containing DMEM medium, followed by incubation for 24 hours. Next, each well was treated with 3 µM of TMab4 in 0.5 ml of fresh medium for 30 minutes, and then washed rapidly three times with PBS and incubated in medium at 37° C. for 0, 2 and 6 hours. Thereafter, the medium was removed, and each well was washed with PBS, and then proteins attached to the surface were removed with weakly acidic solution (200 mM glycine, 150 mM NaCl pH 2.5). After washing with PBS, the cells were fixed in 4% paraformaldehyde at 25° C. for 10 minutes.

After washing with PBS, each well was incubated with PBS buffer containing 0.1% saponin, 0.1% sodium azide and 1% BSA at 25° C. for 10 minutes to form pores in the cell membranes. After washing with PBS, each well was incubated with PBS buffer containing 2% BSA at 25° C. for 1 hour to eliminate nonspecific binding. Then, the cells were stained with an FITC (green fluorescence) or TRITC (red fluorescence)-labeled antibody (Sigma) that specifically recognizes human Fc. Rab5 was incubated with anti-rab5 against the early endosome marker rab5. Each well was incubated with anti-flag antibodies against a flag-tag of rab11, a recycling endosome marker, at 25° C. for 1 hour, and was then incubated with TRITC (red fluorescence) or FITC (green fluorescence)-labeled secondary antibody at 25° C. for 1 hour. To observe late endosomes and lysosomes, the cells being incubated were treated with 1 mM LysoTracker Red DND-99 at 30 minutes before cell fixation. The nucleus was blue-stained with Hoechst33342 and observed with a confocal microscope. As a result, it was shown that, unlike TAT, TMab4 was located in early endosomes up to 2 hours, and then was not transported to lysosomes or recycling endosomes.

Example 3: Evaluation of the Effect of Acidification in Early Endosomes on Endosomal Escape To obtain more clear evidence that the cytosol-penetrating antibody of the present disclosure escapes from early endosomes, an experiment was performed using inhibitors.

Specifically, the inhibitors used were wortmannin that inhibits maturation from early endosomes to late endosomes, bafilomycin that prevents endosomal oxidation by inhibiting ATPase hydrogen pump, and brefeldin A that inhibits transport from endosomes to endoplasmic reticulum and Golgi.

FIG. 2a shows the results of confocal microscopy observation of the cytosol-penetrating ability of the cytosol-penetrating antibody TMab4 or the cell-penetrating peptide TAT according to the present disclosure in the presence or absence of an inhibitor thereof.

Specifically, HeLa cells were prepared in the same manner as described in Example 2. When the cells were stabilized, the cells were incubated with each of 100 nM wortmannin, 200 nM bafilomycin and 7 µM brefeldin A for 30 minutes. Next, the cells were incubated with each of PBS, 2 µM TMab4 and 2 µM TAT at 37° C. for 6 hours. The cells were washed with PBS and weakly acidic solution in the same manner as described in Example 2, and then subjected to cell fixation, cell perforation and blocking processes. The TMab4-treated cells were stained with an FITC (green fluorescence)-labeled antibody that specifically recognizes human Fc. The nucleus was blue-stained with Hoechst 33342 and observed with a confocal microscope. In the case of TMab4, green fluorescence localized in the cytosol was not observed only in the bafilomycin-treated cells, and spot-shaped fluorescence appeared.

FIG. 2b is a bar graph showing the results of quantifying the FITC (green fluorescence) fluorescence of the confocal micrographs shown in FIG. 2a.

Specifically, using Image J software (National Institutes of Health, USA), 20 cells were selected in each condition, and then the obtained mean values of fluorescence are graphically shown.

FIG. 2c shows the results of observing the cytosolic localization of the cytosol-penetrating antibody TMab4 or the cell-penetrating peptide TAT according to the present disclosure by confocal microscopy using calcein in the presence or absence of an inhibitor thereof.

Specifically, HeLa cells were prepared in the same as described in Example 2, and were incubated in serum-free medium with each of 200 nM wortmannin, 200 nM bafilomycin and 7 µM brefeldin A for 30 minutes. Next, the cells were incubated with each of PBS, 2 µM TMab4 and 20 µM TAT at 37° C. for 6 hours. After 4 hours, each well containing PBS or the antibody was treated with 150 µM calcein and incubated at 37° C. for 2 hours. In the same manner as described in Example 2, the cells were washed with PBS and weakly acidic solution, and then fixed.

The nucleus was blue-stained with Hoechst 33342 and observed with a confocal microscope. As a result, green calcein fluorescence appeared, indicating that calcein did escape from endosomes into the cytosol by the cytosol-penetrating antibody TMab4 of the present disclosure and TAT. However, in the case of TMab4, green calcein fluorescence localized in the cytosol could not be observed only in the bafilomycin-treated cells, unlike the cells treated with other inhibitors.

FIG. 2d is a bar graph showing the results of quantifying the calcein fluorescence of the confocal micrographs shown in FIG. 2c.

Specifically, as shown in FIG. 2d, using Image J software (National Institutes of Health, USA), 20 cells were selected in each condition, and then the obtained mean values of fluorescence are graphically shown.

Example 4: Evaluation of the Effect of HSPG Degradation in Early Endosomes on Endosomal Escape The cytosol-penetrating antibody is endocytosed by binding to HSPG on the cell surface. At this time, it is endocytosed with pro-heparanase. Pro-heparanase is activated with endosomal acidification (Gingis-Velitski et al., 2004). Activated heparanase degrades HSPG, and thus the cytosol-penetrating antibody can be freely localized in the cytosol.

FIG. 3a shows the results of Western blot analysis performed to confirm siRNA (short interfering RNA)-induced inhibition of heparanase expression.

Specifically, $1\times10^4$ HeLa cells were added to each well of 6-well plates and cultured in 1 ml of 10% FBS-containing medium at 37° C. in 5% $CO_2$ for 12 hours. After 24 hours of culture, each well was transiently transfected with siRNA. For transient transfection, 500 ng of each of a control siRNA having no targeting ability and an siRNA targeting inhibition of heparanase expression was incubated with 500 µl of Opti-MEM media (Gibco) and 3.5 µl of Lipofectamine 2000 (Invitrogen, USA) in a tube at room temperature for 20 minutes, and then added to each well. 500 µl of antibiotic-free DMEM medium was added to each well which was then incubated at 37° C. in 5% $CO_2$ for 6 hours. Next, the medium was preplaced with 1 ml of 10% FBS-containing DMEM medium, followed by incubation for 72 hours.

After incubation, lysis buffer (10 mM Tris-HCl pH 7.4, 100 mM NaCl, 1% SDS, 1 mM EDTA, Inhibitor cocktail (sigma)) was added to each well to a cell lysate. The cell lysate was quantified using a BCA protein assay kit (Pierce). The gel subjected to SDS-PAGE was transferred to a PVDF membrane, incubated with the antibody (SantaCruz) (which recognize heparanase and β-actin, respectively) at 25° C. for 2 hours, and then incubated with HRP-conjugated secondary antibody (SantaCruz) at 25° C. for 1 hour, followed by detection. Analysis was performed using ImageQuant LAS4000 mini (GE Healthcare).

FIG. 3b shows the results of confocal microscopy observation of cytosol penetrating antibody/lysosome merging caused by inhibition of heparanase expression.

Specifically, HeLa cells with inhibited inhibition of heparanase expression and control HeLa cells were prepared in the same manner as described in Example 2. The cells were treated with each of 3 μM TMab4 and 20 μM FITC-TAT at 37° C. for 30 minutes, washed rapidly three times with PBS, and then incubated in medium at 37° C. for 2 hours. In the same manner as described in Example 2, the cells were washed with PBS and weakly acidic solution, and then subjected to cell fixation, cell perforation and blocking processes.

The TMab4-treated cells were stained with an FITC (green fluoescence)-labeled antibody that specifically recognizes human Fc. The cells were incubated with anti-LAMP-1 (santa cruz) against the lysosome marker LAMP-1 at 25° C. for 1 hour, and incubated with TRITC (red fluorescence)-labeled secondary antibody at 25° C. for 1 hour. The nucleus was blue-stained with Hoechst 33342 and observed with a confocal microscope. In the case of TMab4, merging with LAMP-1 was observed when heparanase expression was inhibited.

FIG. 3c shows the results of confocal microscopy observation performed to confirm the cytosolic localization of a cytosol-penetrating antibody, which is caused by inhibition of heparanase expression.

Specifically, HeLa cells with inhibited inhibition of heparanase expression and control HeLa cells were prepared in the same manner as described in Example 2. The cells were treated with each of 2 μM TMab4 and 20 μM FITC-TAT at 37° C. for 6 hours. After 4 hours, each well containing PBS or the antibody was treated with 150 μM calcein and incubated at 37° C. for 2 hours. In the same manner as described in Example 2, the cells were washed with PBS and weakly acidic solution, and then fixed. The nucleus was blue-stained with Hoechst 33342 and observed with a confocal microscope. In the cells with inhibited expression of heparanase, calcein fluorescence that localized to the cytosol by TMab4 could not be observed.

FIG. 4 is a schematic view showing an overall trafficking process ranging from cellular internalization of a cytosol-penetrating antibody according to the present disclosure to localization of the antibody in the cytosol.

Example 5: Observation of Introduction of Cytosol-Penetrating Intact IgG-Format Monoclonal Antibody Through Cell Membrane at Varying pHs In order for the cytosol-penetrating antibody of the present disclosure to localize in the cytosol after endocytosis, an endosomal escape process is essential. Until now, there has been no report on endosomal escape of antibodies. To elucidate the endosomal escape mechanism, an experiment was performed at simulated endosomal pH.

The components of the inner phospholipid layer of early endosomes are similar to those of the outer phospholipid layer of the cell membrane (Bissig and Gruenberg, 2013), and the major component of the phospholipid layer is 1-palmitoyl-2-oleoyl-sn-glycero-3-phosphatidylcholine (POPC). Thus, assuming that the outer phospholipid layer of the membrane of Ramos cells expressing no HSPG is the same as the inner phospholipid layer of early endosomes, an experiment was performed.

FIG. 5 shows the results of observing a fluorescence-labeled cytosol-penetrating antibody in Ramos cells by confocal microscopy in order to examine whether the antibody can be introduced through the cell membrane depending on pH or whether the antibody can induce cell membrane permeation of other substances.

Specifically, a cover slip was added to 24-well plates, and 200 μl of 0.01% poly-L-lysine solution was added to attach suspending Ramos cells to the plate, followed by incubation at 25° C. for 20 minutes. After washing with PBS, $5 \times 10^4$ Ramos cells were added to each well and incubated in 0.5 ml of 10% FBS-containing medium at 37° C. for 30 minutes. After confirming cell adhesion, the cells were incubated in 200 μl of pH 7.4 buffer (HBSS (Welgene), 50 mM HEPES pH 7.4) or pH 5.5 buffer (HBSS (Welgene), 50 mM MES pH 5.5) with each of 10 μM PBS and TMab4 labeled directly with the fluorescent reagent DyLight-488, 10 μM non-labeled TMab4 and 2 μM control antibody adalimumab labeled directly with DyLight-488, at 37° C. for 2 hours. Adalimumab used as the control antibody is a therapeutic antibody that targets extracellular cytokines.

In the same manner as described in Example 2, the cells were washed with PBS, and then fiaxed. The nucleus was blue-stained with Hoechst 33342 and observed with a confocal microscope. At pH 5.5, the fluorescence of TMab4 labeled directly with DyLight-488 was observed. At pH 5.5, green FITC fluorescence was observed in the cells treated with TMab4 and adalimumab labeled directly with DyLight-488. It was confirmed that the cytosol-penetrating antibody was introduced through the cell membrane at acidic pH and could introduce other substance as well as itself.

In addition, it was confirmed that the morphology of the cell membrane was maintained, even though the substance was introduced externally.

Example 6: Examination of Whether Cytosol-Penetrating Antibody Forms Pores by Trypan Blue Uptake Depending on pH Among known endosomal escape mechanisms, endosomal perforation was expected to be the most promising endosomal escape mechanism by which an intact IgG-format substance can escape from endosomes while maintaining the morphology of endosomes as shown in the experimental results.

Similar to Example 5, an experiment was performed in order to observe the morphology of the cell membrane when the cytosol-penetrating antibody passed through the cell membrane.

FIG. 6a shows the results of observing Ramos cells by an optical microscope in order to examine whether a cytosol-penetrating antibody can form pores and take up trypan blue having no membrane-permeating ability, depending on pH. pH 7.4 buffer (HBSS (Welgene), 50 mM HEPES pH 7.4) or pH 5.5 buffer (HBSS (Welgene), 50 mM MES pH 5.5)

Specifically, 5×10⁴ Ramos cells were attached to each well of 24-well plates in the same manner as described in Example 5. After confirming cell adhesion, the cells were incubated with each of TMab4 and 1 µM and 10 µM of adalimumab in 200 µl of pH 7.4 buffer (HBSS (Welgene), 50 mM HEPES pH 7.4 (cytosol pH)) and pH 5.5 buffer (HBSS (Welgene), 50 mM MES pH 5.5) (early endosomal pH)) at 37° C. for 2 hours. After careful washing with PBS, 200 µl of a mixture of 190 µl of PBS and 10 µl of trypan blue was added to each well, and the cells were observed with a microscope.

FIG. 6b is a graph quantitatively comparing the number of cells that have taken up trypan blue.

Specifically, the number of cells showing trypan blue uptake was counted and expressed as percentage relative to the total number of cells. A total of 400 or more cells were counted, and the mean values are graphically shown.

As shown in FIG. 6b, only at pH 5.5, the cells treated with the cytosol-penetrating antibody TMab4 of the present disclosure showed trypan blue uptake in a concentration-dependent manner. In addition, it was shown that the morphology of the cell membrane during the passage of the cytosol-penetrating antibody was maintained.

Example 7: Observation of Temporary Ad Reversible Pore Formation by Cytosol-Penetrating Antibody In the case of conventional peptides known to show a pore formation mechanism by the endosomal escape mechanism, it is known that the alpha-helical structure of the peptides forms pores through the cell membrane.

However, since antibodies have no alpha-helical structure, they were generally considered almost impossible to form pores through the cell membrane. Thus, it was assumed that the antibody would escape from endosomes after temporary pore formation, and then the cell membrane would be reversibly restored. To demonstrate this assumption, an experiment was performed.

FIG. 7a shows the results of optical microscopic observation performed to confirm whether cell membrane pores produced by a cytosol-penetrating antibody at pH 5.5 is temporary and reversible.

Specifically, 5×10⁴ Ramos cells were attached to each well of 24-well plates in the same manner as described in Example 5. After conforming cell adhesion, the cells were incubated with 10 µM of TMab4 in 200 µl of pH 5.5 buffer (HBSS (Welgene), 50 mM MES pH 5.5) at 37° C. for 2 hours in order to maintain an early endosomal pH of 5.5. The buffer was replaced with fresh buffer, and the cells were incubated for 2 hours so that the cells could be recovered. After careful washing with PBS, 200 µl of a mixture of 190 µl of PBS and 10 µl of trypan blue was added to each well, and the cells were observed with a microscope.

FIG. 7b is a graph quantitatively comparing the number of cells that have taken up trypan blue uptake. Specifically, a total of 400 or more cells were counted, and the mean values are graphically shown. As shown in FIG. 7b, at pH 5.5, the cells treated with TMab4 having endosomal escape ability according to the present disclosure did take up trypan blue immediately after addition of TMab4, but the cells subjected to recovery in the medium did not take up blue uptake. Namely, it was confirmed that pore formation by the cytosol-penetrating antibody was a temporary and reversible phenomenon.

Example 8: Observation of Membrane Binding and Lipid Membrane Flip-Flop of Cytosol-Penetrating Intact IgG-Format Monoclonal Antibody at Varying pHs The pore formation mechanism is a mechanism by which pores are formed while maintaining the overall morphology of the cell membrane and a substance escapes from endosomes into the cytosol through the pores. For pore formation, it is known that a substance interacts with the inner phospholipid layer of endosomes, and then membrane pores are formed by a flip-flop mechanism (H. D. Herce et al., 2009).

Thus, in order for endosomal escape occurs by pore formation in early endosomes, an antibody should first bind to the cell membrane by endosomal acidification. To confirm this, an experiment was performed.

FIG. 8 shows the results of analyzing the cell membrane binding of a cytosol-penetrating antibody and control antibody adalimumab by flow cytometry (FACS) at varying pHs.

Specifically, 1×10⁵ Ramos were prepared for each sample. The cells were washed with PBS, and then incubated with each of 5 µM TMab4 and 5 µM adalimumab in each of pH 7.4 buffer (TBS, 2% BSA, 50 mM HEPES pH 7.4) (for maintaining a cytosolic pH of 7.4) and pH 5.5 buffer (TBS, 2% BSA, 50 mM MES pH 5.5) (for maintaining an early endosomal pH) at 4° C. for 1 hour. The cells were washed with each pH buffer, and then the cells treated with each of TMab4 or adalimumab were incubated with FITC (green fluorescence)-labeled antibody (which specifically recognizes human Fc) at 4° C. for 30 minutes. The cells were washed with PBS, and then analyzed by flow cytometry. As a result, it was shown that, at pH 5.5, only TMab4 did bind to the cell membrane.

FIG. 9 shows the results of analyzing the cell membrane flip-flop inducing abilities of a cytosol-penetrating antibody and control antibody adalimumab by flow cytometry (FACS) at varying pHs.

Specifically, 1×10⁵ Ramos cells were prepared for each sample. The cells were washed with PBS, and then incubated with each of 5 µM TMab4 and 5 µM adalimumab in each of pH 7.4 buffer (TBS, 2% BSA, 50 mM HEPES pH 7.4) (for maintaining a cytosolic pH of 7.4) and pH 5.5 buffer (TBS, 2% BSA, 50 mM MES pH 5.5) (for maintaining an early endosomal pH of 5.5) at 4° C. for 1 hour.

The cells were washed with each pH buffer, and then incubated with FITC (green fluorescence)-labeled Annexin-V at 25° C. for 15 minutes. Annexin-V is a substance that targets phosphatidylserine, a lipid present only in the cell membrane, and only when cell membrane lipid flip-flop occurs, the lipid can be exposed to the outside and Annexin-V can bind thereto. After washing with PBS, the cells were analyzed by flow cytometry. As a result, it was confirmed that, at pH 5.5, Annexin-V did bind only to TMab4.

FIG. 10 is a schematic view showing a pore formation model of a cytosol-penetrating antibody, expected based on the above-described experiments.

Example 9: Logic of Prediction of pH-Dependent Change in Properties

The reason why the cytosol-penetrating antibody according to the present disclosure showed different cytosol penetration properties depending on pH was assumed to be because a pH-dependent change in interaction between antibody residues led to a change in the properties.

To demonstrate this assumption, literature search was performed. As a result, it was confirmed that as pH decreases from 7.4 (neutral pH) to 5.0, asparaginic acid (D) and glutamic acid (E) among amino acids lose negative charge by protonation and becomes hydrophobic (Korte et al., 1992).

Specifically, asparaginic acid (D) and glutamic acid (E), which have become hydrophobic, hydrophobically interact with methionine (M), leucine (L) and isoleucine (I), which are originally hydrophobic amino acids. The phenomenon that the surrounding amino acids induce structural modification through this newly formed interaction is defined as the Tanford transition (Qin et al., 1998). To confirm this pH-dependent change in the properties, an experiment was performed (Di Russo et al., 2012).

In a hT4 VL structure which is a cytosol-penetrating light-chain variable region, hydrophobic amino acids, methionine (M), isoleucine (I) and leucine (L), which surround histidine (H), asparaginic acid (D) and glutamic acid (E), which can show a difference between pH 7.4 and pH 5.0, were examined.

Among these amino acids, candidate amino acids where the distance between the side chains of two amino acids was less than 6-7 Å were identified, and a pair of the $1^{st}$ and 95th amino acids from the N-terminus were selected as candidate amino acids capable of showing the Tanford transition effect.

Among the pair of the $1^{st}$ and $95^{th}$ amino acids, the 95th amino acid is an amino acid present in the sequence VL-CDR3 of the cytosol-penetrating light-chain variable region hT4 VL. It was confirmed that the $95^{th}$ amino acid could induce a change in the VL-CDR3 loop structure through a phenomenon, such as the Tanford transition, by interaction with the $1^{st}$ amino acid.

It was confirmed that, in the cytosol-penetrating light-chain variable region hT4 VL, the amino acids of the VL-CDR3 loop which was structurally changed by the $1^{st}$ and $95^{th}$ amino acids include a very high proportion of tyrosine (Y) which easily interacts with 1-palmitoyl-2-oleoyl-sn-glycero-3-phosphatidylcholine (POPC) which is the major component of the inner phospholipid layer of early endosomes (Morita et al., 2011).

FIG. 11 shows the results of predicting the pH-dependent structural change of a cytosol-penetrating antibody on the basis of the WAM modeling structure of the light-chain variable region of the cytosol-penetrating antibody, and shows amino acids, which are involved in the structural change, and amino acids which are exposed by the structural change.

In order to confirm the pH-dependent change in properties induced by the $1^{st}$ and $95^{th}$ amino acids and the endosomal escape resulting from the change, mutants were constructed by substituting the $1^{st}$ and $95^{th}$ amino acids with alanine (A).

In addition, in order to confirm the pH-dependent change in properties induced by the $1^{st}$ and $95^{th}$ amino acids and the endosomal escape resulting from the change, mutants were constructed by substituting the $1^{st}$ and $95^{th}$ amino acids with glutamic acid (E) and leucine having properties similar thereto.

Table 1 shows the names and sequences of mutants constructed using an overlap PCR technique.

TABLE 1

| Name of Variable Region | Sequence | SEQ ID NO |
|---|---|---|
| hT4 VL | 1        10        20    abcdef 30        40        50<br>DLVMTQSPSSLSASVGDRVTITCKSSQSLFNSRTRKNYLAWYQQKPGKAPKLLIYW<br>         60        70        80        90        100<br>ASTRESGVPSRFSGSGSGTDFTLTISSLQPEDFATYYCQQYYYHMYTFGQGTKVEIKR | SEQ ID NO: 65 |
| hT4-D1A VL | 1        10        20    abcdef 30        40        50<br>ALVMTQSPSSLSASVGDRVTITCKSSQSLFNSRTRKNYLAWYQQKPGKAPKLLIYW<br>         60        70        80        90        100<br>ASTRESGVPSRFSGSGSGTDFTLTISSLQPEDFATYYCQQYYYHMYTFGQGTKVEIKR | SEQ ID NO: 66 |
| hT4-M95A VL | 1        10        20    abcdef 30        40        50<br>DLVMTQSPSSLSASVGDRVTITCKSSQSLFNSRTRKNYLAWYQQKPGKAPKLLIYW<br>         60        70        80        90        100<br>ASTRESGVPSRFSGSGSGTDFTLTISSLQPEDFATYYCQQYYYHAYTFGQGTKVEIKR | SEQ ID NO: 67 |
| hT4-D1E VL | 1        10        20    abcdef 30        40        50<br>ELVMTQSPSSLSASVGDRVTITCKSSQSLFNSRTRKNYLAWYQQKPGKAPKLLIYW<br>         60        70        80        90        100<br>ASTRESGVPSRFSGSGSGTDFTLTISSLQPEDFATYYCQQYYYHMYTFGQGTKVEIKR | SEQ ID NO: 68 |
| hT4-M95L VL | 1        10        20    abcdef 30        40        50<br>DLVMTQSPSSLSASVGDRVTITCKSSQSLFNSRTRKNYLAWYQQKPGKAPKLLIYW<br>         60        70        80        90        100<br>ASTRESGVPSRFSGSGSGTDFTLTISSLQPEDFATYYCQQYYYHLYTFGQGTKVEIKR | SEQ ID NO: 69 |

In the same manner as described in Example 1, cloning, expression in HEK293F cell lines, and purification were performed.

Example 10: Observation of pH-Dependent Change in Properties of Cytosol-Penetrating Antibody FIG. 12 is a graph quantitatively comparing the number of cells that have taken up trypan blue at varying pHs by mutants (TMab4-D1A), (TMab4-M95A), (TMab4-D1E), and (TMab4-M95L) constructed by substituting the $1^{st}$ amino acid asparaginic acid (D), the $95^{th}$ amino acid methionine (M), the $1^{st}$ amino acid asparaginic acid (A), and the $95^{th}$ amino acid methionine (M) of a light-chain variable region (VL), which are involved in induction of a structural change of a cytosol-penetrating antibody at acidic pH, with alanine (A), alanine (A), glutamic acid (E), and leucine (L), respectively.

Specifically, Ramos cells were attached to plates in the same manner as described in Example 5. Then, the cells were incubated with 10 μM of each of TMab4, Adalimumab, TMab4-D1A, TMab4-M95A, TMab4-D1E and TMab4-M95L in 200 μl of each of pH 7.4 buffer (HBSS (Welgene), 50 mM HEPES pH 7.4) (for maintaining a cytosolic pH of 7.4) and pH 5.5 buffer (HBSS (Welgene), 50 mM MES pH 5.5) (for maintaining an early endosomal pH of 5.5) at 37° C. for 2 hours.

After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown.

It was confirmed that the mutants, TMab4-D1A and TMab4-M95A, showed little or no trypan blue uptake, unlike TMab4. TMab4-D1E and TMab4-M95L showed trypan blue uptake similar to that of TMab4. This suggests that the $1^{st}$ amino acid and the $95^{th}$ amino acid play an important role in endosomal escape.

Example 11: Investigation of Amino Acids and Motifs Contributing to Endosomal Escape Ability of Cytosol-Penetrating Antibody Through the experimental examples obtained in the above Examples, it was found that the pH-dependent change in the properties of the antibody occurred by interaction with the $1^{st}$ and $95^{th}$ antibodies of the cytosol-penetrating antibody and that endosomal escape was induced by the change in the properties.

In order to confirm endosomal escape induced by the pH-dependent change in the properties, mutants were constructed by substituting amino acids of VL-CDR3, which were expected to interact with phospholipid, with alanine (A).

Specifically, based on the results of structural modeling analysis, mutants were constructed by simultaneously substituting the $92^{nd}$, $93^{rd}$ and $94^{th}$ amino acids, which were most likely to be exposed to the surface, with alanine (A).

Table 2 below shows the names and sequences of mutants constructed using an overlap PCR technique.

TABLE 2

| Name of Variable Region | Sequence | SEQ ID NO: |
|---|---|---|
| hT4-Y91A VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQAYYHMYTFGQGTKVEIKR | SEQ ID NO: 70 |
| hT4-Y92A VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQYAHMYTFGQGTKVEIKR | SEQ ID NO: 71 |
| hT4-Y93A VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQYYAHMYTFGQGTKVEIKR | SEQ ID NO: 72 |
| hT4-H94A VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQYYYAMYTFGQGTKVEIKR | SEQ ID NO: 73 |
| hT4-AAA VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQYAAAMYTFGQGTKVEIKR | SEQ ID NO: 74 |
| hT4-Y96A VL | 1         10        20    abcdef 30        40        50<br>DLVMTQSPSSLSASVGDRVTITCKSSQSLFNSRTRKNYLAWYQQKPGKAPKLLIYW<br>        60        70        80        90        100<br>ASTRESGVPSRFSGSGSGTDFTLTISSLQPEDFATYYCQQYYYHMATFGQGTKVEIKR | SEQ ID NO: 75 |

In the same manner as described in Example 1, cloning, expression in HEK293F cell lines, and purification were performed.

FIG. 13 is a graph quantitatively comparing the number of cells that have taken up trypan blue depending on pH by mutants constructed by substituting the 92$^{nd}$, 93$^{rd}$, and 94$^{th}$ amino acids of the CDR3 of the light-chain variable region (VL) of a cytosol-penetrating antibody, which can possibly be involved in endosomal escape, with alanine.

Specifically, Ramos cells were attached to plates in the same manner as described in Example 5. Then, the cells were incubated with each of buffer and 10 μM of TMab4, TMab4-Y91A, TMab4-Y92A, TMab4-Y93A, TMab4-H94A, TMab4-AAA and TMab4-Y96A in 200 μl of each of pH 7.4 buffer (HBSS (Welgene), 50 mM HEPES pH 7.4) (for maintaining a cytosolic pH of 7.4) and pH 5.5 buffer (HBSS (Welgene), 50 mM MES pH 5.5) (for maintaining an early endosomal pH of 5.5) at 37° C. for 2 hours.

After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown. It was shown that TMab4-Y92A, TMab4-Y93A and TMab4-H94A showed significantly reduced trypan blue uptake compared to TMab4. In particular, TMab4-AAA showed little or no trypan blue uptake. However, TMab4-Y91A and TMab4-Y96A showed trypan blue uptake similar to that of TMab4. This suggests that the 92$^{nd}$, 93$^{rd}$ and 94$^{th}$ amino acids greatly contribute to endosomal escape.

Example 12: Confirmation of Contribution of CDR1 and CDR2 of Cytosol-Penetrating Antibody Light-Chain Variable Region (VL) to Endosomal Escape The above-described experimental results demonstrated that the CDR3 of the light-chain variable region (VL) is involved in endosomal escape. Then, in order to elucidate the effect of the CDR1 and CDR2 of the light-chain variable region (VL), which are involved in endocytosis, on endosomal escape, an experiment was performed.

The CDR1 and CDR2 of the light-chain variable region (VL) were substituted with CDR sequences which have the same amino acid number or do not include the cationic patch sequence of CDR1 involved in endocytosis, among human germline sequences. At this time, amino acids known to be important for the stability of the existing light-chain variable region were conserved.

Table 3 below shows the names and sequences of mutants constructed using genetic synthesis.

TABLE 3

| Name of Variable Region | Sequence | SEQ ID NO: |
|---|---|---|
| hT4-01 VL | 1         10         20     abcd     40         50<br>DLVMTQSPSSLSASVGDRVTITCKASQGLSSYLAWYQQKPGKAPKLLIYW<br>60         70         80         90        100<br>ASTLESGVPSRFSGSGSGTDFTLTISSLQPEDFATYYCQQYYYHMYTFGQGTKVEIKR | SEQ ID NO: 76 |
| hT4-02 VL | 1         10         20     abcd     40         50<br>DLMVTQSPSSLSASVGDRVTITCKSSQSLLYSSNNKNYLAWYQQKPGKAPKLLIYW<br>60         70         80         90        100<br>ASTRESGVPSRFSGSGSGTDFTLTISSLQPEDFATYYCQQYYYHMYTFGQGTKVEIKR | SEQ ID NO: 77 |
| hT4-03 VL | 1         10         20     abcd     40         50<br>DLVMTQSPSSLSASBGDRVTITCKSSQSLLDSDDGNTYLAWYQQKPGKAPKLLIYW<br>60         70         80         90        100<br>LSYRASGVPSRFSGSGSGTDFTLTISSLQPEDFATYYCQQYYYHMYTFGQGTKVEIKR | SEQ ID NO: 78 |

In the same manner as described in Example 1, cloning, expression in HEK293F cell lines, and purification were performed.

FIG. 14a shows the results of confocal microscopy performed to analyze the cytosol-penetrating ability of mutants constructed by substituting the CDR1 and CDR2 of the light-chain variable region (VL) of a cytosol-penetrating antibody, which bind to HSPG receptor and are involved in cytosol-penetrating ability, with human germline sequences.

Specifically, HeLa cells were prepared in the same manner as described in Example 2. When the cells were stabilized, the cells were incubated with each of PBS and 2 μM TMab4, TMab4-01, TMab4-02 and TMab4-03 at 37° C. for 6 hours. The cells were washed with PBS and weakly acidic solution in the same manner as described in Example 2, and then subjected to cell fixation, cell perforation and blocking processes.

TMab4 was stained with an Alexa-488 (green fluorescence)-labeled antibody that specifically recognizes human Fc. The nucleus was blue-stained with Hoechst33342 and observed with a confocal microscope. All the three mutants showed reduced intracellular fluorescence compared to wild-type TMab4. In particular, in the case of TMab4-03, little or no intracellular fluorescence was observed.

FIG. 14b shows a graph quantitatively comparing the number of cells that have taken up trypan blue depending on pH by mutants constructed by substituting the CDR1 and CDR2 of the light-chain variable region (VL) of a cytosol-penetrating antibody, which bind to HSPG receptor and are involved in cytosol-penetrating ability, with human germline sequences.

Specifically, Ramos cells were attached to plates in the same manner as described in Example 5. Then, the cells were incubated with each of buffer and 10 μM of TMab4, TMab4-01, TMab4-02 and TMab4-03 in 200 μl of each of pH 7.4 buffer (HBSS (Welgene), 50 mM HEPES pH 7.4) (for maintaining a cytosolic pH of 7.4) and pH 5.5 buffer (HBSS (Welgene), 50 mM MES pH 5.5) (for maintaining an early endosomal pH of 5.5) at 37° C. for 2 hours. After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown. As a result, the mutants, TMab4-01 and TMab4-03, showed trypan blue uptake similar to that of TMab4. Namely, it was demonstrated that, in the light-chain variable region, the region involved in endocytosis (VL-CDR1 and VL-CDR2) is distinguished from the region involved in endosomal escape (VL-CDR3).

Example 13: Logic of Improvement in Endosomal Escape Ability of Cytosol-Penetrating Antibody The $92^{nd}$, $93^{rd}$ and $94^{th}$ amino acids are expected to increase solvent accessibility for binding to the inner phospholipid membrane of early endosomes, which is the early mechanism of endosomal escape, through the change in properties of VL-CDR3 by interaction with the $1^{st}$ and 95th amino acids of the cytosol-penetrating light-chain variable region. These amino acids are tyrosine (Y), tyrosine (Y) and histidine (H), respectively.

These amino acids easily interact with 1-palmitoyl-2-oleoyl-sn-glycero-3-phosphatidylcholine (POPC) which is the major component of the inner phospholipid layer of early endosomes.

In order to confirm that the three amino acids expected to be exposed due to a change in pH conditions interact with the inner phospholipid layer of early endosomes and are involved in endosomal escape and to increase the proportion of cytosol-penetrating antibody that escapes from endosomes, mutants for the $92^{nd}$, $93^{rd}$ and $94^{th}$ amino acids were constructed.

For mutant construction, literature search was performed, and as a result, amino acids that easily interact with 1-palmitoyl-2-oleoyl-sn-glycero-3-phosphatidylcholine (POPC) were selected (Morita et al., 2011). The mutant design was made such that the selected amino acids are introduced into the $92^{nd}$, $93^{rd}$ and $94^{th}$ amino acids.

Specifically, the average binding activity of 20 different amino acids for 1-palmitoyl-2-oleoyl-sn-glycero-3-phosphatidylcholine (POPC) is higher in the order of tryptophan (W), phenylalanine (F), tyrosine (Y), leucine (L), isoleucine (I), cysteine (C), and methionine (M).

Specifically, the binding activity of 20 different amino acids for the hydrophilic head portion of 1-palmitoyl-2-oleoyl-sn-glycero-3-phosphatidylcholine (POPC) is higher in the order of arginine (R), tryptophan (W), tyrosine (Y), histidine (H), asparagine (N), glutamine (Q), lysine (K), and phenylalanine (F). In addition, the binding activity of 20 different amino acids for the hydrophobic head portion of 1-palmitoyl-2-oleoyl-sn-glycero-3-phosphatidylcholine (POPC) is higher in the order of tryptophan (W), phenylalanine (F), leucine (L), methionine (M), isoleucine (I), valine V), and tyrosine (Y).

Based on such results, it was confirmed that tryptophan (W) is an amino acid that most easily interacts with POPC which is the major component of the inner phospholipid layer of early endosomes (Morita et al., 2011). Thus, in the present disclosure, a strategy of substituting one or two amino acids with tryptophan (W) was adopted.

Tables 4, 5 and 6 below show the sequences of the designed mutant light-chain variable regions expected to improve the endosomal escape ability of the human antibody having cytosol-penetrating ability. Table 4 below shows the full-length sequences of the light-chain variable regions of the human antibody according to the Kabat numbering system, and Tables 5 and 6 below show the CDR1 and CDR2 sequences or CDR3 sequences of the antibody sequences shown in Table 4.

TABLE 4

| Name of Variable Region | Sequence | SEQ ID NO: |
|---|---|---|
| hT4-WWH VL1 | ```
          10         20    abcdef 30         40         50
DLVMTQSPSSLSASVGDRVTITCKSSQSLFNSRTRKNYLAWYQQKPGKAPKLLIYW
          60         70         80         90        100
ASTRESGVPSRFSGSGSGTDFTLTISSLQPEDFATYYCQQYWWHMYTFGQGTKVEIKR
``` | SEQ ID NO: 1 |
| hT4-WYW VL1 | ```
          10         20    abcdef 30         40         50
DLVMTQSPSSLSASVGDRVTITCKSSQSLFNSRTRKNYLAWYQQKPGKAPKLLIYW
          60         70         80         90        100
ASTRESGVPSRFSGSGSGTDFTLTISSLQPEDFATYYCQQYWYWMYTFGQGTKVEIKR
``` | SEQ ID NO: 2 |
| hT4-YWW VL1 | ```
          10         20    abcdef 30         40         50
DLVMTQSPSSLSASVGDRVTITCKSSQSLFNSRTRKNYLAWYQQKPGKAPKLLIYW
          60         70         80         90        100
ASTRESGVPSRFSGSGSGTDFTLTISSLQPEDFATYYCQQYYWWMYTFGQGTKVEIKR
``` | SEQ ID NO: 3 |
| hT4-WYH VL1 | ```
          10         20    abcdef 30         40         50
DLVMTQSPSSLSASVGDRVTITCKSSQSLFNSRTRKNYLAWYQQKPGKAPKLLIYW
          60         70         80         90        100
ASTRESGVPSRFSGSGSGTDFTLTISSLQPEDFATYYCQQYWYHMYTFGQGTKVEIKR
``` | SEQ ID NO: 4 |
| hT4-YWH VL1 | ```
          10         20    abcdef 30         40         50
DLVMTQSPSSLSASVGDRVTITCKSSQSLFNSRTRKNYLAWYQQKPGKAPKLLIYW
          60         70         80         90        100
ASTRESGVPSRFSGSGSGTDFTLTISSLQPEDFATYYCQQYYWHMYTFGQGTKVEIKR
``` | SEQ ID NO: 5 |

TABLE 5

| | CDR1 Sequence | | | | | | | | | | | | | | | | CDR2 Sequence | | | | | | |
|---|---|---|---|---|---|---|---|---|---|---|---|---|---|---|---|---|---|---|---|---|---|---|---|
| Kabat No. | 24 | 25 | 26 | 27 | 27 a | 27 b | 27 c | 27 d | 27 e | 27 f | 28 | 29 | 30 | 31 | 32 | 33 | 34 | 50 | 51 | 52 | 53 | 54 | 55 | 56 |
| Light Chain Variable Region | K | S | S | Q | S | L | F | N | S | R | T | R | K | N | Y | L | A | W | A | S | T | R | E | S |
| SEQ ID NO: | SEQ ID NO: 6 | | | | | | | | | | | | | | | | | SEQ ID NO: 7 | | | | | | |

TABLE 6

| Name of Light Chain Variable Region | CDR3 Sequence | | | | | | | | SEQ ID |
|---|---|---|---|---|---|---|---|---|---|
| Kabat No. | 89 | 90 | 91 | 92 | 93 | 94 | 95 | 96 | 97 NO: |
| hT4-WWH VL | Q | Q | Y | W | W | H | M | Y | T SEQ ID NO: 8 |
| hT4-WYW VL | Q | Q | Y | W | Y | W | M | Y | T SEQ ID NO: 9 |
| hT4-YWW VL | Q | Q | Y | Y | W | W | M | Y | T SEQ ID NO: 10 |
| hT4-WYH VL | Q | Q | Y | W | Y | H | M | Y | T SEQ ID NO: 11 |
| hT4-YWH VL | Q | Q | Y | Y | W | H | M | Y | T SEQ ID NO: 12 |

Example 14: Expression and Purification of Cytosol-Penetrating Antibody Mutants Expected to have Increased Endosomal Escape Ability and Confirmation of Maintenance of Cytosol-Penetrating Ability For animal cell expression of cytosol-penetrating antibody mutants expected to have increased endosomal escape ability, vectors expressing the light chain were constructed as described in Example 1 above. To this end, DNA encoding a light chain comprising the cytosol-penetrating light-chain variable region (hT4 VL) or the mutant antibody's light-chain variable region (hT4-WWH VL, hT4-WYW VL, hT4-YWW VL, hT4-WYH VL, hT4-YWH VL) and light chain constant region (CL), which has a secretion signal peptide-encoding DNA fused to the 5' end, was cloned into a pcDNA3.4 vector (Invitrogen) by use of NotI/HindIII.

Next, a humanized hT0 VH-encoding animal expression vector and the constructed animal expression vector encoding the light chain comprising the light-chain variable region expected to have increased endosomal escape ability were transiently transfected into HEK293F protein-expressing cells. Next, purification of the cytosol-penetrating antibody mutant expected to have increased endosomal escape ability was performed in the same manner as described in Example 1.

FIG. 15*a* shows the results of 12% SDS-PAGE analysis under reducing or non-reducing conditions after purification of cytosol-penetrating antibody mutants expected to have improved endosomal escape ability.

Specifically, under non-reducing conditions, a molecular weight of about 150 kDa was observed, and under reducing conditions, the heavy chain showed a molecular weight of 50 kDa, and the light chain showed a molecular weight of 25 kDa. This suggests that the expression and purified cytosol-penetrating antibody mutants expected to have increased endosomal escape ability are present as monomers in a solution state and do not form dimers or oligomers through non-natural disulfide bonds.

FIG. 15*b* shows the results of confocal microscopy performed to examine whether the cytosol-penetrating ability of cytosol-penetrating antibody mutants expected to have improved endosomal escape ability is maintained.

Specifically, HeLa cells were prepared in the same manner as described in Example 2 above. When the cells were stabilized, the cells were incubated with each of PBS and 2 μM TMab4, TMab4-WWH, TMab4-WYW, TMab4-YWW, TMab4-WYH and TMab4-YWH at 37° C. for 6 hours.

The cells were washed with PBS and weakly acidic solution in the same manner as described in Example 2, and then subjected to cell fixation, cell perforation and blocking processes. Each antibody was stained with an FITC (green fluorescence)-labeled antibody that specifically recognizes human Fc. It was found that in all the five mutants, the cytosol-penetrating ability was maintained.

Example 15: Confirmation of pH Dependence of Cytosol-Penetrating Antibody Mutants Expected to have Increased Endosomal Escape Ability FIG. 16 is a graph quantitatively comparing the number of cells that have taken up trypan blue depending on pH by a cytosol-penetrating antibody wild-type and cytosol-penetrating antibody mutants expected to have improved endosomal escape ability.

Specifically, Ramos cells were attached to plates in the same manner as described in Example 5. Then, the cells were incubated with each of 1 μM TMab4, Adalimumab, TMab4-WWH, TMab4-WYW, TMab4-YWW, TMab4-WYH and TMab4-YWH in 200 j of each of pH 7.4 buffer (HBSS (Welgene), 50 mM HEPES pH 7.4 (cytosol pH)) and pH 5.5 buffer (HBSS (Welgene), 50 mM MES pH 5.5 (early endosomal pH)) (early endosomal pH) at 37° C. for 2 hours. After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown. Among the five mutants, TMab4-WYW, TMab4-YWW, TMab4-WYH and TMab4-YWH showed increased trypan blue uptake, and among them, TMab4-WYW showed pH-dependent trypan blue uptake.

TMab4-WYW, which showed increased pH-dependent trypan blue uptake while retaining the cytosol-penetrating ability of the wild-type antibody, was selected as a final clone.

Example 16: Confirmation of Improvement in Cytosol Localization of Cytosol-Penetrating Antibody Mutant Having Increased Endosomal Escape Ability FIG. 17a shows the results of observing the cytosolic localization of a cytosol-penetrating antibody wild-type and cytosol-penetrating antibody mutants expected to have improved endosomal escape ability, by confocal microscopy using calcein.

Specifically, HeLa cells were prepared in the same manner as described in Example 2. The cells were incubated with PBS or 0.1 µM, 0.5 µM and 1 µM of each of TMab4 and TMab4-WYW in serum-free medium at 37° C. for 6 hours. After 4 hours, each well containing PBS or the antibody was treated with 150 µM calcein and incubated at 37° C. for 2 hours. The cells were washed with PBS and weakly acidic solution in the same manner as described in Example 2, and then fixed. The nucleus was blue-stained with Hoechst33342 and observed with a confocal microscope. It was confirmed that TMab4-WYW showed green calcein fluorescence with higher intensity even at lower concentration than TMab4.

FIG. 17b is a bar graph showing the results of quantifying the calcein fluorescence of the confocal micrographs shown in FIG. 17a.

Specifically, using Image J software (National Institutes of Health, USA), 20 cells were selected in each condition, and then the obtained mean values of fluorescence are graphically shown.

Example 17: Confirmation of Cytosol Localization of Cytosol-Penetrating Monoclonal Antibody by Enhanced Split-GFP Complementation Assay FIG. 18 is a schematic view showing a process in which GFP fluorescence by enhanced split-GFP complementation is observed when a cytosol-penetrating antibody wild-type and a mutant having improved endosomal escape ability localizes in the cytosol.

Specifically, an enhanced split-GFP complementation system was used to confirm that the cytosol-penetrating antibody would localize to the cytosol. When the green fluorescence protein GFP is split into a fragment 1-10 and a fragment 11, the fluorescent property is removed, and when the two fragments become closer to each other and are combined with each other, the fluorescent property can be restored (Cabantous et al., 2005).

Based on this property, the GFP fragment 1-10 was expressed in the cytosol, and the GFP fragment 11 was fused to the C-terminus of the cytosol-penetrating antibody. In addition, for complementation between the GFP fragments, streptavidin and streptavidin-binding peptide 2 (SBP2) having high affinity were fused to the GFP fragments. Thus, the fact that GFP fluorescence indicates that the cytosol-penetrating antibody localizes in the cytosol.

Example 18: Expression and Purification of Cytosol-Penetrating Antibody Fused with GFP11-SBP2

For expression of a GFP11-SBP2-fused cytosol-penetrating antibody in animal cells, GFP11-SBP2 was genetically fused to the C-terminus of the heavy chain by three GGGGS linkers. Next, the animal expression vector encoding the cytosol-penetrating light chain or the cytosol-penetrating light chain having increased endosomal escape ability, and the animal expression vector encoding the GFP11-SBP2-fused heavy chain, were transiently co-transfected. Next, purification of the GFP11-SBP2-fused cytosol-penetrating antibody was performed in the same manner as described in Example 1.

FIG. 19 shows the results of 12% SDS-PAGE analysis under reducing or non-reducing conditions after purification of a GFP11-SBP2-fused cytosol-penetrating antibody wild-type and a GFP11-SBP2-fused mutant having improved endosomal escape ability.

Specifically, under non-reducing conditions, a molecular weight of about 150 kDa was observed, and under reducing conditions, the heavy chain showed a molecular weight of 50 kDa, and the light chain showed a molecular weight of 25 kDa. This suggests that the expressed purified GFP11-SBP2-fused cytosol-penetrating antibody is present as a monomer in a solution state and does not form a dimer or an oligomer by a non-natural disulfide bond.

Example 19: Examination of GFP Fluorescence with Cytosol Localization of GFP11-SBP2-Fused Cytosol-Penetrating Antibody FIG. 20a shows the results of confocal microscopy performed to examine the GFP fluorescence of a GFP11-SBP2-fused cytosol-penetrating antibody wild-type and a GFP11-SBP2-fused mutant having improved endosomal escape ability by enhanced split-GFP complementation.

Specifically, transformed HeLa cells stably expressing SA-GFP1-10 were prepared in the same manner as described in Example 2. When the cells were stabilized, the cells were incubated with PBS or 0.2, 0.4, 0.6, 0.8, 1.6 or 3.2 µM of each of TMab4-GFP11-SBP2 and TMab4-WYW-GFP11-SBP2 at 37° C. for 6 hours.

In the same manner as described in Example 2, the cells were washed with PBS and weakly acidic solution, and then fixed. The nucleus was blue-stained with Hoechst 33342 and observed with a confocal microscope. It was observed that TMab4-WYW showed green GFP fluorescence with higher intensity at lower concentration than TMab4.

FIG. 20b is a graph showing the results of quantifying the GFP fluorescence of the confocal micrographs shown in FIG. 20a.

Specifically, using Image J software (National Institutes of Health, USA), 20 cells were selected in each condition, and then the obtained mean values of fluorescence are graphically shown.

In order to quantitatively express and compare the intracytosolic concentrations and endosomal escape efficiencies of the GFP11-SBP2-fused intact IgG-format antibody and the cytosol-penetrating antibody having increased endosomal escape ability, an experiment was performed.

Table 7 below shows the intracytosolic concentrations and endosomal escape efficiencies of the GFP11-SBP2-fused intact IgG-format antibody and the cytosol-penetrating antibody having increased endosomal escape ability.

TABLE 7

| Parameters | cytotransmabs | Treated concentrations (μM) | | |
|---|---|---|---|---|
| | | 0.1 | 0.5 | 1 |
| Cytosolic concentration (nM)$^c$ | TMab4 | 12 ± 5 | 68 ± 4 | 170 ± 9 |
| | TMab4-WYW | 34 ± 7 | 232 ± 9 | 527 ± 35 |
| Endosomal escaping efficiency (%)$^d$ | TMab4 | 1.1 ± 0.4 | 2.6 ± 0.1 | 4.3 ± 0.1 |
| | TMab4-WYW | 3.2 ± 0.4 | 8.7 ± 0.1 | 13.2 ± 0.5 |

Example 20: In-Depth Analysis of Interaction Between Cytosol-Penetrating Antibody Having Increased Endosomal Escape Ability and Lipid It was found that when the 92$^{nd}$ and 94$^{th}$ amino acids of the light-chain variable region CDR3 of the wild-type cytosol-penetrating antibody were substituted with tryptophan, the endosomal escape ability was increased.

In order to determine whether this increase in the endosomal escape ability is due to improved interaction with any part of the lipid, an experiment was performed. Tryptophan (W) is an amino acid that easily interacts with both the hydrophilic head and hydrophobic tail of the lipid. When tryptophan is substituted with arginine (R) (which easily interacts with the hydrophilic head), isoleucine (I) (which easily interacts with the hydrophilic tail) or glycine (G) (which very weakly interacts with the lipid) and the activities are compared, it can be seen that the interaction with any part of the lipid plays an important role.

In order to analyze in depth the interaction between the cytosol-penetrating antibody having increased endosomal escape ability and the lipid, mutants were constructed by substituting tryptophan with each of arginine (R), isoleucine (I) and glycine (G).

Table 8 below shows the names and sequences of the mutants constructed using an overlap PCR technique.

mutants obtained by substitution with arginine, isoleucine and glycine, which are amino acids having properties opposite to those of tryptophan.

Specifically, 1×10$^5$ Ramos cells were prepared for each well. The cells were washed with PBS, and then incubated with each of 3 μM TMab4, TMab4-WYW, TMab4-RYR, TMab4-IYI and TMab4-GYG in each of pH 7.4 buffer (TBS, 2% BSA, 50 mM HEPES pH 7.4 (cytosolic pH)), and pH 5.5 buffer (TBS, 2% BSA, 50 mM MES pH 5.5 (early endosomal pH)) at 4° C. for 1 hour. After washing with each pH buffer, TMab4, TMab4-WYW, TMab4-RYR, TMab4-IYI and TMab4-GYG were incubated with an FITC (green fluorescence)-labeled antibody (which specifically recognizes human Fc) at 4° C. for 30 minutes. After washing with PBS, the cells were analyzed by flow cytometry, and as a result, it was found that, at pH 5.5, only TMab4 did bind to the cell membrane.

FIG. 21b is a graph quantitatively comparing the number of cells that have taken up trypan blue depending on pH by mutants obtained by substitution with arginine, isoleucine and glycine, which are amino acids having properties opposite to those of tryptophan.

Specifically, Ramos cells were attached to plates in the same manner as described in Example 5. Then, the cells were incubated with each of 1 μM TMab4, TMab4-WYW, TMab4-RYR, TMab4-IYI and TMab4-GYG in 200 μl of

TABLE 8

```
Name of                                                              SEQ
Variable                                                             ID
 Region   Sequence                                                   NO:

hT4-RYR VL1       10        20      abcdef  30        40        50  SEQ
          DLVMTQSPSSLSASVGDRVTITCKSSQSLFNSRTRKNYLAWYQQKPGKAPKLLIYW    ID
                  60        70          80        90        100     NO:
          ASTRESGVPSRFSGSGSGTDFTLTISSLQPEDFATYYCQQYRYRMYTFGQGTKVEIKR  13 hT4-IYI VL1       10        20      abcdef  30        40        50  SEQ
          DLVMTQSPSSLSASVGDRVTITCKSSQSLFNSRTRKNYLAWYQQKPGKAPKLLIYW    ID
                  60        70          80        90        100     NO:
          ASTRESGVPSRFSGSGSGTDFTLTISSLQPEDFATYYCQQYIYIMYTFGQGTKVEIKR  14 hT4-GYG VL1       10        20      abcdef  30        40        50  SEQ
          DLVMTQSPSSLSASVGDRVTITCKSSQSLFNSRTRKNYLAWYQQKPGKAPKLLIYW    ID
                  60        70          80        90        100     NO:
          ASTRESGVPSRFSGSGSGTDFTLTISSLQPEDFATYYCQQYGYGMYTFGQGTKVEIKR  15
```

In the same manner as described in Example 1, cloning, expression in HEK293F cell lines, and purification were performed.

Example 21: In-Depth Analysis of Interaction Between Cytosol-Penetrating Antibody and Lipid FIG. 21a is a graph showing the results of flow cytometry (FACS) performed to analyze the cell membrane binding of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 4° C. for 2 hours. After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown. As a result, TMab4-RYR, TMab4-IYI and TMab4-GYG showed reduced trypan blue uptake compared to TMab4-WYW.

FIG. 21c is a bar graph showing the results of observing the cytosolic localization of mutants obtained by substitution with arginine, isoleucine and glycine, which are amino acids having properties opposite to those of tryptophan by confocal microscopy using calcein and quantifying the calcein fluorescence of the confocal micrographs.

Specifically, HeLa cells were prepared in the same manner as described in Example 2. The cells were incubated with each of 0.5 µM TMab4, TMab4-WYW, TMab4-RYR, TMab4-IYI and TMab4-GYG 0.5 µM at 37° C. for 6 hours. After 4 hours, each well containing PBS or the antibody was treated with 150 µM calcein 150 µM and incubated at 37° C. for 2 hours. In the same manner as described in Example 2, the cells were washed with PBS and weakly acidic solution, and then fixed. The nucleus was blue-stained with Hoechst33342 and observed with a confocal microscope. In the cells treated with TMab4-RYR, TMab4-IYI or TMab4-GYG, the green calcein fluorescence localized in the cytosol was weaker than that in the cells treated with TMab4-WYW.

Therefore, it was confirmed that interactions with all the hydrophilic head and hydrophobic tail of the lipid were involved in endosomal escape, and for this reason, substitution with tryptophan increased the endosomal escape ability.

Example 22: Expression and Purification of Intact IgG-Format Anti-Tubulin Cytosol-Penetrating Antibody The mutant having increased endosomal escape ability can more effectively target a protein located in the cytosol, because the amount of antibody located in the cytosol will increase.

FIG. 22a is a schematic view showing a process of constructing an intact IgG-format anti-tubulin cytosol-penetrating antibody to be used to examine the activity of cytosol-penetrating antibody mutants having improved endosomal escape ability.

For the purpose of expression of an intact IgG-format anti-tubulin cytosol-penetrating antibody in animal cells, DNA encoding a heavy chain comprising the heavy-chain variable region and heavy chain constant region (CH1-hinge-CH2-CH3) binding specifically to cytoskeletal tubulin, which has a secretion signal peptide-encoding DNA fused to the 5' end, was cloned into a pcDNA3.4 vector (Invitrogen) by use of NotI/HindIII (Laurence et al., 2011).

Next, the animal expression vector encoding the cytosol-penetrating light chain or the cytosol-penetrating light chain having increased endosomal escape ability, and the constructed animal expression vector encoding the heavy chain comprising the heavy-chain variable region that specifically to tubulin, were transiently co-transfected into HEK293F protein-expressing cells. Next, purification of the intact IgG-format anti-tubulin cytosol-penetrating antibody was performed in the same manner as described in Example 1. FIG. 22b shows the results of 12% SDS-PAGE analysis under reducing or non-reducing conditions after purification of an intact IgG-format anti-tubulin cytosol-penetrating antibody.

Specifically, under non-reducing conditions, a molecular weight of about 150 kDa was observed, and under reducing conditions, the heavy chain showed a molecular weight of 50 kDa, and the light chain showed a molecular weight of 25 kDa. This suggests that the expressed purified intact IgG-format anti-tubulin cytosol-penetrating antibody is present as a monomer in a solution state and does not form a dimer or an oligomer by a non-natural disulfide bond.

Example 23: Confirmation of Cytoskeletal Tubulin-Specific Binding of Intact IgG-Format Anti-Tubulin Cytosol-Penetrating Antibody FIG. 22c shows the results of confocal microscopy performed to examine whether an intact IgG-format anti-tubulin cytosol-penetrating antibody would merge with cytoskeletal tubulin localized in the cytosol.

Specifically, HeLa cells were prepared in the same manner as described in Example 2. The cells were incubated with PBS or each of 3 µM TuT4 and TuT4-WYW in 500 µl of 10% FBS-containing medium at 37° C. for 6 hours. The cells were washed with PBS and weakly acidic solution in the same manner as described in Example 2, and then subjected to cell fixation, cell perforation and blocking processes.

Cytoskeletal tubulin was incubated with anti-tubulin antibody (Santa Cruz) at 25° C. for 1 hour, and incubated with TRITC (red fluorescence)-labeled secondary antibody at 25° C. for 1 hour. Each antibody was stained with an FITC (green fluorescence)-labeled antibody that specifically recognizes human Fc. The nucleus was blue-stained with Hoechst33342 and observed with a confocal microscope.

As shown in FIG. 22c, with the cytosol portion in which red fluorescent tubulin was localized, green fluorescent TuT4-WYW was merged in a fibrillar shape, but TuT4 was not merged.

Example 24: Expression and Purification of Intact IgG-Format RAS-Targeting Cell-Penetrating Antibody and Analysis of Affinities of K-RAS Mutants In order to confirm whether the cytosol-penetrating antibody can effectively target other intracytosolic proteins in addition to cytoskeletal tubulin, an experiment was performed.

FIG. 23a is a schematic view showing a process of constructing an intact IgG-format RAS-targeting cytosol-penetrating antibody to be used to examine the activity of mutants having improved endosomal escape ability.

For the purpose of expression of an intact IgG-format Ras-targeting cytosol-penetrating antibody in animal cells, DNA encoding a heavy chain the heavy-chain variable region (RT11 VH) and heavy chain constant region (CH1-hinge-CH2-CH3) binding specifically to GTP-bound K-RAS, which has a secretion signal-encoding DNA fused to the 5' end, was cloned into a pcDNA3.4 vector (Invitrogen) by use of NotI/HindIII as described in Example 5.

Next, the animal expression vector encoding the cytosol-penetrating light chain or the cytosol-penetrating light chain having increased endosomal escape ability, and the constructed animal expression vector encoding the heavy chain comprising the heavy-chain variable region that binds specifically to GTP-bound K-RAS, were transiently co-transfected into HEK293F protein-expressing cells. Next, purification of the intact IgG-format Ras-targeting cytosol-penetrating antibody was performed in the same manner as described above.

FIG. 23b shows the results of 12% SDS-PAGE analysis under reducing or non-reducing conditions after purification of intact IgG-format RAS-targeting cytosol-penetrating antibodies.

Specifically, under non-reducing conditions, a molecular weight of about 150 kDa was observed, and under reducing conditions, the heavy chain showed a molecular weight of 50 kDa, and the light chain showed a molecular weight of 25 kDa. This suggests that the expressed purified intact IgG-format Ras-targeting cytosol-penetrating antibody is present as a monomer in a solution state and does not form a dimer or an oligomer by a non-natural disulfide bond.

FIG. 23c shows the results of enzyme linked immunosorbent assay performed to measure the affinities of antibodies for GppNHp-bound K-RAS G12D and GDP-bound K-RAS G12D, which are K-RAS mutants.

Specifically, GTP is very easily hydrolyzed, and hence it is difficult to maintain the morphology of GTP-bound K-RAS G12D. Thus, in order to enable K-RAS to have an activated structure, like GTP, a GTP-bound K-RAS G12D antigen was constructed using GppNHp which is a non-hydrolyzable GTP analogue. Each of a GppNHp-bound K-RAS G12D and a GDP-bound K-RAS G12D, which are target molecules, was incubated in 96-well EIA/RIA plates (COSTAR Corning) at 37° C. for 1 hour, followed by washing three times with 0.1% PBST (0.1% Tween20, pH 7.4, 137 mM NaCl, 12 mM phosphate, 2.7 mM KCl) (SIGMA) for 10 minutes each time. Each well was incubated with 5% PBSS (5% Skim milk, pH7.4, 137 mM NaCl, 12 mM phosphate, 2.7 mM KCl) (SIGMA) for 1 hour, and then washed three times with 0.1% PBST for 10 minutes. Next, each well was incubated with each of the IgG-format cytosol-penetrating antibodies (TMab4, RT11, and RT11-WYW), and then washed three times with 0.1% PBST for 10 minutes. As a marker antibody, goat alkaline phosphatase-conjugated anti-human mAb (SIGMA) was used. Each well was treated with pNPP (p-nitrophenyl palmitate) (Sigma), and the absorbance at 405 nm was measured.

Affinities for the K-RAS mutants were analyzed, and as a result, it was shown that there was little or no difference in affinity between wild-type RT11 and mutant RT11-WYW. TMab4 used as a negative control did not bind, and all the clones did not bind to the GDP-bound K-RASs.

Example 25: Confirmation of Specific Binding Between Intact IgG-Format Anti-RAS Cytotransmab and GTP-Bound K-RAS in Cells FIG. 24 shows the results of confocal microscopy observation performed to examine whether intact IgG-format RAS-targeting cytosol-penetrating antibodies would merge with intracellular H-RAS G12V mutants.

Specifically, fibronectin (Sigma) was coated on a 24-well plate, and then 0.5 ml of a dilution of $2 \times 10^4$ NIH3T3 cells expressing mCherry (red fluorescence) H-RAS G12V was added to each well and incubated at 37° C. in 5% $CO_2$ for 12 hours. Next, the cells were treated with each of 2 μM TMab4, RT11 and RT11-WYW and incubated at 37° C. for 12 hours. Next, the cells were stained in the same manner as described in Example and were observed with a confocal microscope.

As shown in FIG. 24, with the inner cell membranes in which red fluorescent activated RAS was located, green fluorescent RT11 or RT11-WYW was merged, but TMab4 was not merged.

From the above results, it was found that the intact IgG-format Ras-targeting cytosol-penetrating antibody did bind specifically to activated RAS in cells. The degree of merging was higher in the order of RT11-WYW and RT11.

Example 26: Analysis of Properties of D1-M95 Inducing Structural Change Depending on pH For more detailed analysis of the properties of the $1^{st}$ amino acid asparaginic acid (D) and $95^{th}$ amino acid methionine (M) of the light-chain variable region (VL), which induce a change in the properties of the cytosol-penetrating antibody depending on pH, mutants were constructed by substituting the $1^{st}$ amino acid in the antibody backbone with each of glutamic acid (E), alanine (A) and asparagine (N) present in the germline sequences, and substituting the $95^{th}$ amino acid in the CDR3 with each of all the 20 amino acids.

When the mutants were constructed, the $87^{th}$ amino acid tyrosine was substituted with phenylalanine in order to increase the protein expression yield that decreased by the improved endosomal escape motif. Phenylalanine is an amino acid that can easily interact with the aromatic ring amino acids and hydrophobic amino acids located in the backbone of the heavy-chain variable region, thus enhancing the interface between the light-chain variable region and the heavy-chain variable region. The light-chain variable region, in which the $87^{th}$ amino acid is substituted with phenylalanine and which has the improved endosomal escape motif WYW at the $92^{nd}$, $93^{rd}$ and $94^{th}$ amino acid, was named 'hT4-3'. Thus, the cytosol-penetrating intact IgG-format antibody comprising the light-chain variable region was named 'TMab4-3'.

In the same manner as described in Example 1, each of the mutants was cloned, expressed in HEK293F cell lines, and purified.

FIG. 25b is a graph showing the results of quantitatively comparing the number of cells that have taken up trypan blue depending on pH by mutants constructed by substituting $95^{th}$ amino acid methionine of the light-chain variable region (VL) of a cytosol-penetrating antibody, which induce a structural change of the cytosol-penetrating antibody at acidic pH 5.5, with various amino acids.

Specifically, $1 \times 10^4$ adherent cells (pgsD-677) expressing no HSPG receptor were incubated. On the next day, in the same manner as described in Example 5, the cells were incubated with each of 1 μM TMab4-3, TMab4-3 D1A, TMab4-3 DiE and TMab4-3 DIN in 200 μl of each of pH 7.4 buffer (HBSS (Welgene), 50 mM HEPES pH 7.4) (for maintaining cytosolic pH) and pH 5.5 buffer (HBSS (Welgene), 50 mM MES pH 5.5) (for maintaining early endosomal pH) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured.

As a result, TMab4-3 ME showed trypan blue uptake similar to that of the wild-type, and the TMab4-3 DIA and TMab4-3 DIN mutants showed reduced trypan blue uptake.

FIG. 25b is a graph showing the results of quantitatively comparing the number of cells that have taken up trypan blue depending on pH by mutants constructed by substituting $95^{th}$ amino acid methionine of the light-chain variable region (VL) of a cytosol-penetrating antibody, which induce a structural change of the cytosol-penetrating antibody at acidic pH 5.5, with various amino acids.

Specifically, pgsD-677 cells were prepared in the same manner as described in Example 26. Then, in the same manner as in described Example 5, the cells were incubated with 1 μM of each of TMab4-3 and nineteen TMab4-3 mutants in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 µl of 1% SDS (sodium dodecyl sulfate) to each well.

The cells were transferred to a 96-well plate, and the absorbance at 590 nm was measured. As a result, TMab4-3 M95L, M95I and M95H showed trypan blue uptake similar to that of TMab4-3, and TMab4-3 M95A, M95S, M95V, M95G and M95P mutants showed reduced trypan blue uptake. In addition, TMab4-3 M59D and M59E showed increased pH-dependent trypan blue uptake, but TMab4-3 M95K and M95R mutants showed increased trypan blue uptake at neutral pH.

Therefore, it was found that interaction between hydrophobic amino acids having long side chains, negatively charged amino acids, and histidine (H), is most effective for inducing structural changes at acidic pH.

When the $95^{th}$ amino acid of the light-chain variable region is composed of the hydrophobic amino acid methionine (M), isoleucine (I) or leucine (L), or the negatively charged amino acid asparaginic acid (D) or glutamic acid (E), it is expected that the carboxylic acid in the side chain of the negatively charged amino acid will become hydrophobic by partial protonation, and thus the $95^{th}$ amino acid will hydrophobically interacts with asparaginic acid (D) or glutamic acid (E), which is the $1^{st}$ amino acid of the light-chain variable region or heavy-chain variable region (Du Z et al., 2011; Di Russo et al., 2012).

In addition, when the $95^{th}$ amino acid of the light-chain variable region is composed of histidine (H), it is expected that as pH change from 7.4 to 5.5, the net charge of the amino acid side chains will become positive, and the 95th amino acid will induce endosomal escape by electrostatic interaction with asparaginic acid (D) or glutamic acid (E), which is the $1^{st}$ amino acid of the light-chain variable region or heavy-chain variable region.

Example 27: Design of Mutants Introduced with Amino Acids that 'Induce Change in Properties in Response to pH'

In addition to D1-M95, the present inventors have attempted to introduce amino acids capable of inducing endosomal escape by changing their interaction depending on pH.

Based on the results of structural modeling analysis, the $90^{th}$ and $91^{st}$ amino acids capable of interacting with the $1^{st}$ amino acid asparaginic acid (D) were selected as possible candidates. To enable interaction under acidic pH conditions, the $90^{th}$ amino acid was replaced with histidine (TMab4-3 Q90H), and the $91^{st}$ amino acid was substituted with histidine (TMab4-3 Y91H).

In addition, the $91^{st}$ amino acid capable of additionally interacting with the $2^{nd}$ hydrophobic amino acid was substituted with asparaginic acid (TMab4-3 Y91D).

In addition, the $2^{nd}$ amino acid was also substituted with negatively charged glutamic acid (E) so that it could interact with the $1^{st}$ negatively charged amino acid, and the $90^{th}$ amino acid was substituted with leucine (L) (TMab4-3 L2E Q90L) so that it could interact with the $95^{th}$ hydrophobic amino acid. Furthermore, the $2^{nd}$ amino acid was also substituted with glutamic acid (E) so that it could interact with the $1^{st}$ negatively charged amino acid, and the $97^{th}$ amino acid was substituted with isoleucine (I) (TMab4-3 L2E T97I) so that it could interact with the $95^{th}$ hydrophobic amino acid.

Table 9 below shows the names and sequences of the mutants constructed using an overlap PCR technique.

TABLE 9

| Name of Variable Region | Sequence | SEQ ID NO: |
|---|---|---|
| hT4-3 VL | DLVMTQSPSSLSASVGDRVTITCKSSQSLFNSRTRKNYLAWYQQKPGKAPKLLIYW ASTRESGVPSRFSGSGSGTDFTLTISSLQPEDFATYFCQQYWYMMYTFGQGTKVEIKR | SEQ ID NO: 16 |
| hT4-3 D1E-M95L VL | ELVMTQSPSSLSASVGDRVTITCKSSQSLRNSRTRKNYLAWYQQKPGKAPKLLIYW ASTRESGVPSRFSGSGSGTDFTLTISSLQPEDFATYYCQQYWYWLYTFGQGTKVEIKR | SEQ ID NO: 17 |
| hT4-3 Y91H VL | DLVMTQSPSSLSASVGDRVTITCKSSQSLFNSRTRKNYLAWYQQKPGKAPKLLIYW ASTRESGVPSRFSGSGSGTDFTLTISSLQPEDFATYYCQQHWYWMYTFGQGTKVEIKR | SEQ ID NO: 18 |
| hT4-3 Y91D VL | DLVMTQSPSSLSASVGDRVTITCKSSQSLFNSRTRKNYLAWYQQKPGKAPKLLIYW ASTRESGVPSRFSGSGSGTDFTLTISSLQPEDFATYYCQQHWYWMYTFGQGTKVEIKR | SEQ ID NO: 19 |
| hT4-3 L2E Q90L VL | DEVMTQSPSSLSASVGDRVTITCKSSQSLFNSRTRKNYLAWYQQKPGKAPKLLIYW ASTRESGVPSRFSGSGSGTDFTLTISSLQPEDFATYYCQLYWYWMYTFGQGTKVEIKR | SEQ ID NO: 20 |

TABLE 9-continued

| Name of Variable Region | Sequence | SEQ ID NO: |
|---|---|---|
| hT4-3 L2E T97I VL | 1        10        20    abcdef 30        40        50<br>DEVMTQSPSSLSASVGDRVTITCKSSQSLFNSRTRKNYLAWYQQKPGKAPKLLIYW<br>       60        70        80        90        100<br>ASTRESGVPSRFSGSGSGTDFTLTISSLQPEDFATYYCQQYWYWMYIFGQGTKVEIKR | SEQ ID NO: 21 |
| hT4-3 Q90H M95A VL | 1        10        20    abcdef 30        40        50<br>DLVMTQSPSSLSASVGDRVTITCKSSQSLFNSRTRKNYLAWYQQKPGKAPKLLIYW<br>       60        70        80        90        100<br>ASTRESGVPSRFSGSGSGTDFTLTISSLQPEDFATYYCQHYWYWAYTFGQGTKVEIKR | SEQ ID NO: 22 |
| hT4-3 Q90H VL | 1        10        20    abcdef 30        40        50<br>DLVMTQSPSSLSASVGDRVTITCKSSQSLFNSRTRKNYLAWYQQKPGKAPKLLIYW<br>       60        70        80        90        100<br>ASTRESGVPSRFSGSGSGTDFTLTISSLQPEDFATYYCQHYWYWMYTFGQGTKVEIKR | SEQ ID NO: 23 |

In the same manner as described in Example 1, each of the mutants was cloned, expressed in HEK293F cell lines, and purified.

Example 28: Confirmation of Improvement in Endosomal Escape Ability of Mutants Introduced with Amino Acids that 'Induce Change in Properties in Response to pH'

FIG. 26a shows a graph showing quantitatively comparing the number of cells that have taken up trypan blue depending on pH by mutants designed for the purpose of 'inducing an additional change in properties in response to pH'.

Specifically, cells were prepared in the same manner as described in Example 26. Then, in the same manner as described in Example 5, the cells were incubated with 0.5 or μM of each of seven mutants (including TMab4-3, TMab4-3 D1E-M95L, etc.) in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured.

As a result, the TMab4-3 Q90H mutant showed higher trypan blue uptake than TMab4-3 at 0.5 μM. Additionally, using the TMab4-3 Q90H mutant showing a significant difference from the wild-type, an experiment was performed.

FIG. 26b shows a bar graph showing the results of observing the cytosolic localization of mutants designed for the purpose of inducing an additional change in properties in response to pH by confocal microscopy using calcein and quantifying the calcein fluorescence of the confocal micrographs.

Specifically, HeLa cells were prepared in the same manner as described in Example 2, and the cells were incubated with 0.5 μM and 1 μM of each of TMab4-3 and TMab4-3 Q90H at 37° C. for 6 hours. After 4 hours, each well containing PBS or the antibody was treated with 150 μM calcein and incubated at 37° C. for 2 hours. The cells were washed with PBS and weakly acidic solution in the same manner as described in Example 2, and then fixed. The nucleus was blue-stained with Hoechst33342 and observed with a confocal microscope.

As a result, in the cells treated with TMab4-3 Q90H, green calcein fluorescence localized in the cytosol increased compared to that in the cells treated with TMab4-3. Therefore, it was confirmed that, in addition to the 95$^{th}$ amino acid of the light-chain variable region of the cytosol-penetrating antibody, the 90$^{th}$ amino acid interacted with the 1$^{st}$ amino acid and induced endosomal escape by a pH-dependent change in the interaction.

Table 10 below the CDR3 sequence of the light-chain variable region of the mutant having an increased ability to escape from endosomes by inducing an additional change in the properties depending on pH.

TABLE 10

| Name of Light Chain Variable Region | CDR3 Sequence | | | | | | | | | SEQ ID NO: |
|---|---|---|---|---|---|---|---|---|---|---|
| Kabat No. | 89 | 90 | 91 | 92 | 93 | 94 | 95 | 96 | 97 | |
| hT43 Q90H VL | Q | H | Y | W | Y | W | M | Y | T | SEQ ID NO: 24 |

Example 29: Investigation of Endosomal Escape Ability at Varying Lengths of CDR3 of Light-Chain Variable Region 85% or more of the CDR3 of the light-chain variable region consists of 9 amino acids. Depending on the number and composition of amino acids, the CDR3 loop structure varies. In the present disclosure, to analyze how the endosomal escape ability changes depending on the number and composition of amino acids, mutants comprising a CDR3 consisting of 8, 10 or 11 amino acids were constructed.

Table 11 below shows the names and sequences of the mutants constructed using an overlap PCR technique.

TABLE 11

| Name of Variable Region | Sequence | SEQ ID NO: |
|---|---|---|
| hT4-3 L8-1 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYFCQQYWYWMTFGQGTKVEIKR | SEQ ID NO: 25 |
| hT4-3 L8-2 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYFCQQWYWMPTFGQGTKVEIKR | SEQ ID NO: 26 |
| hT4-3 L10-1 VL | 1         10        20     abcdef  30        40        50<br>DLVMTQSPSSLSASVGDRVTITCKSSQSLRNSRTRKNYLAWYQQKPGKAPKLLIYW<br>          60        70        80        90        100<br>ASTRESGVPSRFSGSGSGTDFTLTISSLQPEDFATYFCQQYWYWPMYTFGQGTKVEIKR | SEQ ID NO: 27 |
| hT4-3 L10-2 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYYCQQYWYWLMYTFGQGTKVEIKR | SEQ ID NO: 28 |
| hT4-3 L10-3 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYYCQQYWYWYMYTFGQGTKVEIKR | SEQ ID NO: 29 |
| hT4-3 L11-1 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYYCQQYWYWLYMYTFGQGTKVEIKR | SEQ ID NO: 30 |
| hT4-3 L11-2 VL | 1         10        20     abcdef  30        40        50<br>DLVMTQSPSSLSASVGDRVTITCKSSQSLFNSRTRKNYLAWYQQKPGKAPKLLIYW<br>          60        70        80        90        100<br>ASTRESGVPSRFSGSGSGTDFTLTISSLQPEDFATYYCQQYPWYWPMYTFGQGTKVEIKR | SEQ ID NO: 31 |

In the same manner as described in Example 1, each of the mutants was cloned, expressed in HEK293F cell lines, and purified.

FIG. 27 is a graph quantitatively comparing the number of cells that taken up trypan blue depending on pH by mutants obtained by changing the amino acid number of the CDR3 of the light-chain variable region of a cytosol-penetrating antibody.

Specifically, cells were prepared in the same manner as described in Example 26. Then, in the same manner as described in Example 5, the cells were incubated with 1 μM of each of seven mutants (including TMab4-3, TMab4-3 L8-1, etc.) in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured.

As a result, in comparison with TMab4-3, the mutants showed increased trypan blue uptake at neutral pH as the number of amino acids increased. The reason is believed to be as follows. As the number of amino acids increases, the overall CDR3 loop structure is stretched, and the endosomal escape motif WYW which binds to the cell membrane in order to escape from endosomes is exposed to the outside, and thus trypan blue uptake increases even at neutral pH.

In addition, in the experimental results, it was confirmed that even when the distance between the $95^{th}$ amino acid, which induces endosomal escape by a pH-dependent change in interaction, and the $92^{nd}$, $93^{rd}$ or $94^{th}$ amino acid, which influences endosomal escape by binding to the phospholipid, increases, the properties of the endosomal escape motif are maintained.

Example 30: Logic of Possibility of Imparting Improved Endosomal Escape Motif to Light-Chain Variable Region of Conventional Therapeutic Antibody Currently commercially available therapeutic antibodies include many kinds of monoclonal antibodies that target cell surface receptors, particularly cell surface receptors that undergo endocytosis. However, these conventional antibodies have disadvantages in that their binding to antigen is not broken after endocytosis, and these antibodies do not localize in the cytosol and are released out of the cells because they have no endosomal escape ability. Thus, if endosomal escape ability can be imparted to these receptor-targeting antibodies that undergo endocytosis, there is an advantage in that these antibodies can be used in a wider range of applications.

In addition, the use of the stable backbone of commercially available therapeutic antibodies can increase the overall expression yield, and when the affinity of these antibodies for HSPG, a non-tumor-specific receptor, is eliminated, tumor tissue specificity can be imparted to these antibodies.

To impart an improved endosomal escape motif, the sequences of the light-chain variable regions of receptor-targeting antibodies that undergo endocytosis were compared with the sequence of the light-chain variable region of the cytosol-penetrating antibody. As a result, candidate light-chain variable regions were selected, which have a negatively charged amino acid as the 1st amino acid and in which backbone amino acids that can influence the CDR3 loop structure are the same as those of the cytosol-penetrating antibody.

Mutants were constructed by the CDR3 sequences of the candidate light-chain variable regions with the CDR3 sequence of the cytosol-penetrating antibody.

Table 12 shows the names and sequences of the mutants constructed using a genesis synthesis technique.

ing affinity and cytosol-penetrating ability of an intact IgG-format RAS-targeting cytosol-penetrating antibody in which an improved endosomal escape motif is introduced into the light-chain variable region of a conventional therapeutic antibody would be reduced or eliminated.

Specifically, HeLa cells were prepared in the same manner as described in Example 2. When the cells were stabilized, the cells were incubated with PBS or each of 1 μM RT11-3, RT11-Neci-WYW, RT11-Nimo-WYW, RT11-Pani-WYW, RT11-Pert-WYW, RT11-Lumr-WYW and RT11-Emib-WYW at 37° C. for 6 hours.

The cells were washed with PBS and weakly acidic solution in the same manner as described in Example 2, and

TABLE 12

| Name of Variable Region | Sequence | SEQ ID NO: |
|---|---|---|
| Necitumumab-WYW VL | 1          10         20        abcd        40         50<br>EIVMTQSPATLSLSPGERATLSCRASQSVSSYLAWYQQKPGQAPRLLIYD<br>          60         70         80         90         100<br>ASNRATGIPARFSGSGSGTDFTLTISSLEPEDFAVYFCQQYWYWMYTFGQGTKAEIKR | SEQ ID NO: 32 |
| Panitumumab-WYW VL | 1          10         20        abcd        40         50<br>DIQMTQSPSSLSASVGDRVTITCQASQDISNYLNWYQQKPGKAPKLLIYD<br>          60         70         80         90         100<br>ASNLETGVPSRFSGSGSGTDFTFTISSLQPEDIATYFCQQYWYWMYTFGGGTKVEIKR | SEQ ID NO: 33 |
| Lumretuzumab-WYW VL | 1          10         20        abcdef  30         40         50<br>DIVMTQSPDSLAVSLGERATINCKSSQSVLNSGNQKNYLTWYQQKPGQAPKLLIYW<br>          60         70         80         90         100<br>ASTRESGVPDRFSGSGSGTDFTLTISSLQAEDVAVYFCQQYWYWMYTFGQGTKLEIKR | SEQ ID NO: 34 |
| Nimotuzumab-WYW VL | 1          10         20        abcdef  30         40         50<br>DIQMTQSPSSLSASVGDRVTITCRSSQNIVHSNGNTYLDWYQQTPGKAPKLLIYK<br>          60         70         80         90         100<br>VSNRFSGVPSRFSGSGSGTDFTFTISSLQPEDIATYFCQQYWYWMYTFGQGTKLQITR | SEQ ID NO: 35 |
| Emibetuzumab-WYW VL | 1          10         20        abcd        40         50<br>DIQMTQSPSSLSASVGDRVTITCSVSSSVSSIYLHWYQQKPGKAPKLLIYS<br>          60         70         80         90         100<br>TSNLASGVPSRFSGSGSGTDFTLTISSLQPEDFATYFCQQYWYWMYTFGGGTKVEIKR | SEQ ID NO: 36 |
| Pertuzumab-WYW VL | 1          10         20        abcd        40         50<br>DIQMTQSPSSLSASVGDRVTITCKASQDVSIGVAWYQQKPGKAPKLLIYS<br>          60         70         80         90         100<br>ASYRYTGVPSRFSGSGSGTDFTLTISSLQPEDFATYFCQQYWYWMYTFGQGTKVEIKR | SEQ ID NO: 37 |

FIG. 28a shows a process of constructing an intact IgG-format RAS-targeting cytosol-penetrating antibody in which an improved endosomal escape motif is introduced into the light-chain variable region of a conventional therapeutic antibody.

As shown in FIG. 28a, in the same manner as described in Example 1, cloning of the light-chain variable region was performed, and the resulting animal expression vector and he animal expression vector encoding the heavy chain comprising the heavy-chain variable region that binds specifically to GTP-bound K-RAS were transiently co-transfected into HEK293F protein-expressing cells. Next, purification of the resulting intact IgG-format anti-RAS cytotransmab was performed in the same manner as described in Example 1.

Example 31: Confirmation of Possibility of Imparting Improved Endosomal Escape Motif to Light-Chain Variable Region of Conventional Therapeutic Antibody FIG. 28b shows the results of fluorescence microscopic observation performed to examine whether the HSPG bind-then subjected to cell fixation, cell perforation and blocking processes. Each of the antibodies was stained with an FITC (green fluorescence)-labeled antibody that specifically recognizes human Fc. The nucleus was blue-stained with Hoechst33342 and observed with a confocal microscope. As a result, in all the six intact IgG-format RAS-targeting cytosol-penetrating antibodies comprising the monoclonal antibody backbone imparted with the improved endosomal escape motif, no fluorescence was observed.

FIG. 28c shows a graph quantitatively comparing the number of cells that taken up trypan blue at acidic pH by an intact IgG-format RAS-targeting cytosol-penetrating antibody in which an improved endosomal escape motif is introduced into the light-chain variable region of a conventional therapeutic antibody.

Specifically, Ramos cells were attached to plates in the same manner as described in Example 5. Then, the cells were incubated with each of 1 μM RT11-3, RT11-Neci-WYW, RT11-Nimo-WYW, RT11-Pani-WYW, RT11-Pert-WYW, RT11-Lumr-WYW, and RT11-Emib-WYW in 200 μl of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope.

The number of cells showing trypan blue uptake was counted and expressed as percentage relative to the total number of cells. A total of 400 or more cells were counted, and the mean values are graphically shown. As a result, except for RT11-Pert, the five intact IgG-format RAS-targeting cytosol-penetrating antibodies comprising the therapeutic antibody backbone imparted with the improved endosomal escape motif showed trypan blue uptake similar to that of RT11-3.

Example 32: Confirmation of Maintenance of Specific Binding Between Intact IgG-Format RAS-Targeting Cytosol-Penetrating Antibody Comprising Therapeutic Antibody Backbone Imparted with Improved Endosomal Escape Motif and GTP-Bound K-RAS FIG. 29a shows the results of ELISA performed to measure the affinities of an intact IgG-format RAS-targeting cytosol-penetrating antibody, in which an improved endosomal escape motif is introduced into the light-chain variable region of a conventional therapeutic antibody, for GppNHp-bound K-RAS G12D and GDP-bound K-RAS G12D, which are K-RAS mutants.

Specifically, each of a GppNHp-bound K-RAS G12D and a GDP-bound K-RAS G12D, which are target molecules, was incubated in 96-well EIA/RIA plates (COSTAR Corning) at 37° C. for 1 hour, followed by washing three times with 0.1% PBST (0.1% Tween20, pH 7.4, 137 mM NaCl, 12 mM phosphate, 2.7 mM KCl) (SIGMA) for 10 minutes. Each well was incubated with 5% PBSS (5% Skim milk, pH7.4, 137 mM NaCl, 12 mM phosphate, 2.7 mM KCl) (SIGMA) for 1 hour, and then washed three times with 0.1% PBST for 10 minutes. Next, each well was incubated with each of the IgG-format RAS-targeting cytosol-penetrating antibodies (RT11-3, RT11-Neci-WYW, RT11-Nimo-WYW, RT11-Pani-WYW, RT11-Pert-WYW, RT11-Lumr-WYW, RT11-Emib-WYW), and then washed three times with 0.1% PBST for 10 minutes. As a marker antibody, goat alkaline phosphatase-conjugated anti-human mAb (SIGMA) was used. Each well was treated with pNPP (p-nitrophenyl palmitate) (Sigma), and the absorbance at 405 nm was measured.

Affinities for the K-RAS mutants were analyzed. As a result, except for RT11-Nimo, the five intact IgG-format RAS-targeting cytosol-penetrating antibodies comprising the therapeutic antibody backbone imparted with the endosomal escape motif showed no difference in affinity from RT11-3, and all the clones did not bind to the GDP-bound K-RASs used as negative controls.

FIG. 29b shows a schematic view showing a process of constructing an intact IgG-format RAS-targeting cytosol-penetrating antibody in which an improved endosomal escape motif is introduced into the RGD10 peptide-fused light-chain variable region of a conventional therapeutic antibody.

Because the intact IgG-format RAS-targeting cytosol-penetrating antibody imparted with the improved endosomal escape motif showed no cell-penetrating ability, an RGD10 peptide specific for integrin αvβ3 which is overexpressed in neovascular cells and various tumors was genetically fused to the N-terminus of the light chain by two GGGGS linkers. The RGD10 peptide has an affinity similar to that of a RGD4C peptide, but has characteristics in that it has a single disulfide bond formed by two cysteine residues and can be genetically fused.

In addition, based on the results of analysis of expression yield, endosomal escape ability, and affinity for Ras, the RGD10 peptide was fused to the N-terminus of the light-chain variable region of each of RT11-Pani-WYW and RT11-Neci-WYW which are excellent candidate antibodies.

FIG. 29c shows the results of confocal microscopy performed to examine whether an intact IgG-format RAS-targeting cytosol-penetrating antibody in which an improved endosomal escape motif is introduced into the RGD10 peptide-fused light-chain variable region of a conventional therapeutic antibody would merge with intracellular activated H-RAS G12V mutants.

Specifically, 0.5 ml of a dilution of $2\times10^4$ human colorectal cancer SW480 cells having a K-RAS G12V mutation were added to each of a 24-well plate and incubated with each of 1 μM RT11-i3, RT11-i-Neci-WYW and RT11-i-Pani-WYW at 37° C. in 5% $CO_2$ for 12 hours. Next, in the same manner as described in Example 2, antibody labeling and nucleus staining were performed, and the cells were treated with a Ras-labeled antibody at 37° C. for 1 hour. Then, the cells were secondary antibody and observed with a confocal microscope.

With the inner cell membrane in which the red fluorescent activated RAS was located, green fluorescent RT11-i3, RT11-i-Neci-WYW and RT11-i-Pani-WYW were merged.

The above experimental results indicate that the intact IgG-format RAS-targeting cytosol-penetrating antibody introduced with the improved endosomal escape motif binds specifically to activated RAS in cells.

Example 33: Logic of Possibility of Imparting Improved Endosomal Escape Motif to CDR of Heavy-Chain Variable Region The heavy-chain variable region and the light-chain variable region are structurally common in that they have a beta-sheet structure as a backbone and are composed of three CDR having a loop structure. Thus, it was considered that the endosomal escape motif of the light-variable variable region, which induces endosomal escape by a pH-dependent change in interaction, can also be applied to the heavy-chain variable region.

Whether this phenomenon is reproducible in the heavy-chain variable region was analyzed through the sequence and three-dimensional structure of the heavy-chain variable region. As a result, the endosomal escape motif could be grafted into the CDR3 at a distance that can interact with the $1^{st}$ amino acid glutamic acid (E) of the heavy-chain variable region.

The number of amino acids in the CDR3 of the wild-type heavy-chain variable region is 11, and the center of the loop structure of the CDR3 is significantly exposed to the surface. For this reason, it is considered that the pH-dependent phenomenon occurring in the light-chain variable region hardly occurs. For this reason, the amino acid number of the CDR3 was reduced to 7 or 8 while maintaining a portion of the sequence.

In addition, it was considered that an amino acid capable of interacting with the $1^{st}$ amino acid of the heavy-chain variable region at early endosomal pH is the $102^{nd}$ amino acid of the heavy-chain variable region and this amino acid is located at a suitable distance. Thus, this amino acid was substituted with leucine (L).

Mutants were constructed by introducing the improved endosomal escape motif into the CDR3 of the heavy-chain variable region.

Tables 13, 14 and 15 show the heavy-chain variable region sequences obtained by grafting the designed endosomal escape motif into the heavy-chain variable region.

Table 13 below shows the full-length sequences of the human antibody light-chain variable regions according to the Kabat numbering system, and Tables 14 and 15 below show the CDR1 and CDR2 sequences or CDR3 sequences of the antibody sequences shown in Table 13.

TABLE 13

| Name of Variable Region | Sequence | SEQ ID NO: |
|---|---|---|
| HT0 VH | EVQLVESGGGLVQPGGSLRLSCAASGYTFTSYVMHWVRQAPGKGLEWVSAINPYNDGNYYADSVKGRFTISRDNSRKTLYLQMNSLRAEDTAVYYCARGAYKRGYAMDYWGQGTTVTVSS | SEQ ID NO: 38 |
| HT0-01 VH | EVQLVESGGGLVQPGGSLRLSCAASGYTFTSYVMHWVRQAPGKGLEWVSAINPYNDGNYYADSVKGRFTISRDNSRKTLYLQMNSLRAEDTAVYYCARGWYWMDLWGQGTTVTVSS | SEQ ID NO: 39 |
| HT0-02 VH | EVQLVESGGGLVQPGGSLRLSCAASGYTFTSYVMHWVRQAPGKGLEWVSAINPYNDGNYYADSVKGRFTISRDNSRKTLYLQMNSLRAEDTAVYYCARGWYWFDLWGQGTTVTVSS | SEQ ID NO: 40 |
| HT0-03 VH | EVQLVESGGGLVQPGGSLRLSCAASGYTFTSYVMHWVRQAPGKGLEWVSAINPYNDGNYYADSVKGRFTISRDNSRKTLYLQMNSLRAEDTAVYYCARGWYWGFDLWGQGTTVTVSS | SEQ ID NO: 41 |
| HT0-04 VH | EVQLVESGGGLVQPGGSLRLSCAASGYTFTSYVMHWVRQAPGKGLEWVSAINPYNDGNYYADSVKGRFTISRDNSRKTLYLQMNSLRAEDTAVYYCARYWYWMDLWGQGTTVTVSS | SEQ ID NO: 42 |

TABLE 14

| Kabat No. | CDR1 Sequence | | | | |
|---|---|---|---|---|---|
| | 31 | 32 | 33 | 34 | 35 |
| Heavy Chain Variable Region | S | Y | V | M | H |
| SEQ ID NO: | SEQ ID NO: 43 | | | | |

| Kabat No. | CDR2 Sequence | | | | | | | | | | | | | | | |
|---|---|---|---|---|---|---|---|---|---|---|---|---|---|---|---|---|
| | 50 | 51 | 52 | 52a | 53 | 54 | 55 | 56 | 57 | 58 | 59 | 60 | 61 | 62 | 63 | 64 | 65 |
| Heavy Chain Variable Region | A | I | N | P | Y | N | D | G | N | Y | Y | A | D | S | V | K | G |
| SEQ ID NO: | SEQ ID NO: 44 | | | | | | | | | | | | | | | |

TABLE 15

| Name of Heavy Chain Variable Region | CDR3 Sequence | | | | | | | | | | SEQ ID NO: |
|---|---|---|---|---|---|---|---|---|---|---|---|
| Kabat No. | 95 | 96 | 97 | 98 | 99 | 100 | 100a | 100b | 100c | 101 | 102 |
| HT0 VH | G | A | R | K | R | G | Y | A | M | D | Y | SEQ ID NO: 45 |
| HT0-01 VH | G | W | Y | W | M | - | - | - | - | D | L | SEQ ID NO: 46 |

TABLE 15-continued

| Name of Heavy Chain Variable Region | CDR3 Sequence | | | | | | | | | | | SEQ ID |
|---|---|---|---|---|---|---|---|---|---|---|---|---|
| Kabat No. | 95 | 96 | 97 | 98 | 99 | 100 | 100a | 100b | 100c | 101 | 102 | NO: |
| HT0-02 VH | G | W | Y | W | M | - | - | - | - | D | L | SEQ ID NO: 47 |
| HT0-03 VH | G | W | Y | W | G | F | - | - | - | D | L | SEQ ID NO: 48 |
| HT0-04 VH | Y | W | Y | W | M | - | - | - | - | D | L | SEQ ID NO: 49 |

FIG. 30a shows a process of constructing a cytosol-penetrating antibody having a light-chain variable region from which endosomal escape ability is removed and a heavy-chain variable region into which an improved endosomal escape motif is introduced.

In order to evaluate the endosomal escape ability of the heavy-chain variable region introduced with the improved endosomal escape motif, the $92^{nd}$ to $94^{th}$ amino acids (WYW) of the light-chain variable region, which are involved in endosomal escape, AAA (three consecutive alanines), thereby removing the function thereof. In the same manner as described in Example 1, cloning of the heavy-chain variable region was performed, and the resulting heavy chain together with the light chain comprising the light-chain variable region from which the endosomal escape motif has been removed was expressed in HEK293F cell lines and purified.

In order to more clearly name the cytosol-penetrating antibody comprising the heavy-chain variable region introduced with the improved endosomal escape motif, TMab4 is abbreviated as CT. In other words, TMab4-AAA is CT-AAA.

Example 34: Confirmation of Possibility of Imparting Improved Endosomal Escape Motif to CDR of Heavy-Chain Variable Region FIG. 30b shows a graph quantitatively comparing the number of cells that have taken up trypan blue depending on pH by a cytosol-penetrating antibody having a light-chain variable region from which endosomal escape ability is removed and a heavy-chain variable region into which an improved endosomal escape motif is introduced.

Specifically, as shown in FIG. 30b, Ramos cells were attached to plates in the same manner as described in Example 5. Then, the cells were incubated with each of 1 μM TMab4-WYW, TMab4-AAA, CT01-AAA, CT02-AAA, CT03-AAA and CT04-AAA in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. The number of cells showing trypan blue uptake was counted and expressed as percentage relative to the total number of cells. A total of 400 or more cells were counted, and the mean values are graphically shown. It was observed that the CT01-AAA, CT02-AAA, CT03-AAA and CT04-AAA all showed trypan blue uptake equal to about half of TMab4-3. However, it was shown that the CT04-AAA mutant showed trypan blue uptake even at neutral pH.

FIG. 30c shows the results of confocal microscopy performed to observe the GFP fluorescence by enhanced split-GFP complementation of a GFP11-SBP2-fused cytosol-penetrating antibody having a light-chain variable region from which endosomal escape ability has been removed, and a heavy-chain variable region into which an improved endosomal escape motif has been introduced.

Specifically, transformed HeLa cells stably expressing SA-GFP1-10 were prepared in the same manner as described in Example 2. When the cells were stabilized, the cells were incubated with PBS or each of 1.6 μM CT01-AAA-GFP11-SBP2, CT02-AAA-GFP11-SBP2, CT03-AAA-GFP11-SBP2 and CT04-AAA-GFP11-SBP2 at 37° C. for 6 hours. The cells were washed with PBS and weakly acidic solution in the same manner as described in Example 2, and then fixed. The nucleus was blue-stained with Hoechst33342 and observed with a confocal microscope. As a result, green fluorescence was observed in the cells with CT01-AAA-GFP11-SBP2, CT02-AAA-GFP11-SBP2, CT03-AAA-GFP11-SBP2 or CT04-AAA-GFP11-SBP2.

FIG. 30d shows the results of confocal microscopy performed using calcein in order to observe the cytosolic localization of a cytosol-penetrating antibody having a light-chain variable region from which endosomal escape ability has been removed and a heavy-chain variable region into which an improved endosomal escape motif has been introduced.

Specifically, HeLa cells were prepared in the same manner as described in Example 2. The cells were incubated with each of 0.2 μM and 1 μM CT01-AAA, CT02-AAA and CT03-AAA at 37° C. for 6 hours. After 4 hours, each well containing PBS or the antibody was treated with 150 μM calcein and incubated at 37° C. for 2 hours. In the same manner as descried in Example 2, the cells were washed with PBS and weakly acidic solution, and then fixed. The nucleus was blue-stained with Hoechst33342 and observed with a confocal microscope. In the cells treated with CT01-AAA or CT02-AAA, green calcein fluorescence localized in the cytosol was similar to that in the cells treated with TMab4. However, in the cells treated with CT03-AAA, green calcein fluorescence localized in the cytosol was weaker than that in the cells treated with CT.

Therefore, it was confirmed that even when the improved endosomal escape motif is imparted to the heavy-chain variable region, the antibody can escape from endosomes and finally localize in the cytosol.

Example 35: Analysis of Properties of E1-L102 of Heavy-Chain Variable Region that Induces Structural Change Depending on pH For more detailed analysis of the $1^{st}$ amino acid glutamic acid and $102^{nd}$ amino acid leucine of the heavy-chain variable region, which induce a structural change depending on pH, mutants were constructed by substituting the $1^{st}$ amino acid in the antibody backbone with each of asparaginic acid, alanine and glutamine present in germline sequences, and substituting the $102^{nd}$ amino acid in the CDR3 with each of 12 amino acids of the light-chain variable region, which showed trypan blue uptake at neutral or acidic pH. In the same manner as described in Example, each of the mutants was cloned, expressed in HEK293F cell lines, and purified.

FIG. 31a is a graph quantitatively comparing the number of cells that taken up trypan blue depending on pH by mutants constructed by substituting the $1^{st}$ amino acid glutamic acid of the heavy-chain variable region (VH) of a cytosol-penetrating antibody, which is involved in induction of a structural change in properties of the antibody at acidic pH 5.5, with various amino acids.

Specifically, $1 \times 10^4$ pgsD-677 cells were incubated in 24-well plates in the same manner as described in Example 26. On the next day, in the same manner as described in Example 5, the cells were incubated with each of 1 μM CT01-AAA, CT01-AAA E1A, CT01-AAA E1D and CT01-AAA E1Q in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured. As a result, CT01-AAA E1D showed trypan blue uptake similar to that of the wild type, and the CT01-AAA E1A and CT01-AAA E1Q mutants showed reduced trypan blue uptake compared to that of the wild type.

FIG. 31a is a graph quantitatively comparing the number of cells that taken up trypan blue depending on pH by mutants constructed by substituting $102^{nd}$ amino acid leucine of the heavy-chain variable region (VH) of a cytosol-penetrating antibody, which is involved in induction of a structural change of the antibody at acidic pH 5.5, with various amino acids.

Specifically, pgsD-677 cells were prepared in the same manner as described in Example 26. Then, in the same manner as in described Example 5, the cells were incubated with 1 μM of each of CT01-AAA and nineteen CT01-AAA L102X mutants in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured. As a result, compared to CT01-AAA, CT01-AAA L102I, L102M, and L102H showed trypan blue uptake similar to that of the wild type, and the CT01-AAA L102K and L102R mutants showed increased trypan blue uptake at neutral pH.

This suggests that interaction between hydrophobic amino acids having long side chains, negatively charged amino acids, and histidine (H), is most effective so that the $102^{nd}$ amino acid of the heavy-chain variable region induces endosomal can escape through a change in interaction at early endosomal pH 5.5, like the $95^{th}$ amino acid of the light-chain variable region.

Example 36: Construction of Endosomal Escape Motif Mutants Having Three Tryptophan Residues In order to improve the endosomal escape ability of the endosomal escape motif having two tryptophan residues, an endosomal escape motif having a total of three tryptophan residues was constructed by substituting the $92^{nd}$ to $94^{th}$ amino acids with tryptophan.

Tables 16 and 17 show light-chain variable region mutant sequences obtained by introducing the endosomal escape motif having three tryptophan residues. Specifically, Table 16 below shows the full-length sequence of the human antibody light-chain variable region according to the Kabat numbering system, and Table 17 below the CDR3 sequence of the antibody sequence shown in Table 16.

TABLE 16

| Name of Variable Region | Sequence | SEQ ID NO: |
|---|---|---|
| hT4-3 VL | 1      10      20   abcdef   30      40      50<br>DLVMTQSPSSLSASVGDRVTITCKSSQSLFNSRTRKNYLAWYQQKPGKAPKLLIYW<br>      60      70      80      90     100<br>ASTRESGVPSRFSGSGSGTDFTLTISSLQPEDFATYFCQQYWYMMYTFGQGTKVEIKR | SEQ ID NO: 16 |
| hT4-3 WWW VL | 1      10      20   abcdef   30      40      50<br>DLVMTQSPSSLSASVGDRVTITCKSSQSLFNSRTRKNYLAWYQQKPGKAPKLLIYW<br>      60      70      80      90     100<br>ASTRESGVPSRFSGSGSGTDFTLTISSLQPEDFATYFCQQYWWWMYTFGQGTKVEIKR | SEQ ID NO: 50 |

TABLE 17

| Name of Light Chain Variable Region | CDR3 Sequence | | | | | | | | | SEQ ID NO: |
|---|---|---|---|---|---|---|---|---|---|---|
| Kabat No. | 89 | 90 | 91 | 92 | 93 | 94 | 95 | 96 | 97 | |
| HT4 3 WWW VL | Q | Q | Y | W | W | W | M | Y | T | SEQ ID NO: 51 |

Tables 18 and 19 show heavy-chain variable region mutant sequences obtained by introducing the endosomal escape motif having three tryptophan residues. Specifically, Table 18 below shows the full-length sequence of the human antibody light-chain variable region according to the Kabat numbering system, and Table 19 below the CDR3 sequence of the antibody sequence shown in Table 18.

TABLE 18

| Name of Variable Region | Sequence | SEQ ID NO: |
|---|---|---|
| HT0-01 VH | 1        10        20        30        40        50<br>EVQLVESGGGLVQPGGSLRLSCAASGYTFTSYVMHWVRQAPGKGLEWVSAINPYNDGNYY<br>60        70        80        90                 110<br>ADSVKGRFTISRDNSRKTLYLQMNSLRAEDTAVYYCARGAYKRGYAMDYWGQGTTVTSS | SEQ ID NO: 38 |
| hT4-3 WWW VL | 1        10        20        30        40        50<br>EVQLVESGGGLVQPGGSLRLSCAASGYTFTSYVMHWVRQAPGKGLEWVSAINPYNDGNYY<br>60        70        80        90                 110<br>ADSVKGRFTISRDNSRKTLYLQMNSLRAEDTAVYYCARGWWWMDLWGQGTTVTSS | SEQ ID NO: 52 |

TABLE 19

| Name of Heavy Chain Variable Region | CDR3 Sequence | | | | | | | | | | | SEQ ID NO: |
|---|---|---|---|---|---|---|---|---|---|---|---|---|
| Kabat No. | 95 | 96 | 97 | 98 | 99 | 100 | 100a | 100b | 100c | 101 | 102 | |
| HT0-01 WWW VH | G | W | W | W | M | - | - | - | - | D | L | SEQ ID NO: 53 |

In order to evaluate the endosomal escape ability of the heavy-chain variable region or heavy-chain variable region comprising the endosomal escape motif having three tryptophan residues, this heavy-chain variable region or heavy-chain variable region and the heavy-chain variable region or light variable region that does not comprise the endosomal escape motif were expressed together in HEK293F cell lines in the same manner as described in Example 1, and purified.

Example 37: Confirmation of Improvement in Endosomal Escape Ability of Intact IgG-Format Cytosol-Penetrating Antibody Comprising the Heavy-Chain Variable Region or Light-Chain Variable Region Introduced with Endosomal Escape Motif Having Two or Three Tryptophan Residues As one strategy for improving the endosomal escape ability, the endosomal escape motif was imparted to both the heavy-chain variable region and the light-chain variable region. Thus, a single intact IgG-format cytosol-penetrating antibody includes a total of four endosomal escape motifs. The heavy-chain variable region and the light-chain variable region, which comprise the endosomal escape motif having two or three tryptophan motifs, were expressed together in HEK293F cell lines in the same manner as described 1 above, and purified.

FIG. 32a shows a graph quantitatively comparing the number of cells that have taken up trypan blue depending on pH by intact IgG-format cytosol-penetrating antibodies having a light-chain variable region and/or a heavy-chain variable region introduced with an endosomal escape motif having three tryptophan residues.

Specifically, pgsD-677 cells were prepared in the same manner as described in Example 26. Then, in the same manner as in described Example 5, the cells were incubated with 0.5 or 1 μM of each of CT-3, CT-3_WWW, CT01-AAA, CT01_WWW-AAA, and CT01-3, and CT01_WWW-3_WWW in 200 μl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 μl of a mixture of 190 μl of PBS and 10 μl of trypan blue was added to each well, and the cells were observed with a microscope. Next, after careful washing with PBS, the cells were lysed by adding 50 μl of 1% SDS (sodium dodecyl sulfate) to each well. The cells were transferred to a 96-well plate, and the absorbance at 590 nm was measured.

As a result, CT-3_WWW, CT01_WWW-AAA and CT01_WWW-3_WWW showed significantly increased trypan blue uptake, compared to the CT-3, CT01-AAA and CT01-3 comprising the existing endosomal escape motif. In addition, compared to CT-3 and CT01-AAA, the CT01-3 and CT01_WWW-3_WWW comprising the endosomal escape motif in both the heavy-chain and light-chain variable regions showed higher trypan blue uptake.

FIG. 32b shows a bar graph showing the results of observing the cytosolic localization of intact IgG-format cytosol-penetrating antibodies having a light-chain variable region and/or a heavy-chain variable region introduced with an endosomal escape motif having three tryptophan residues by confocal microscopy using calcein and quantifying the calcein fluorescence of the confocal micrographs.

Specifically, HeLa cells were prepared in the same manner as described in Example 2. The cells were incubated with 0.25, 0.5 and 1 µM of each of CT-3, CT-3_WWW, CT01-AAA, CT01_WWW-AAA, CT01-3, and CT01_WWW-3_WWW at 37° C. for 6 hours. After 4 hours, each well containing PBS or the antibody was treated with 150 µM calcein and incubated at 37° C. for 2 hours. In the same manner as described in Example 2 The cells were washed with PBS and weakly acidic solution and fixed. The nucleus was blue-stained with Hoechst33342 and observed with a confocal microscope.

As a result, compared to the cells treated with the CT-3, CT01-AAA or CT01-3 comprising the existing endosomal escape motif, the cells treated with CT-3_WWW, CT01_WWW-AAA or CT01_WWW-3_WWW showed stronger green calcein fluorescence that localized in the cytosol. In addition, compared to the cells treated with CT-3 or CT01-AAA, the cells treated with the CT01-3 or CT01_WWW-3_WWW comprising the endosomal escape motif in both the heavy-chain and light-chain variable regions showed stronger green calcein fluorescence that localized in the cytosol.

It was confirmed that the endosomal escape motif having three tryptophan motifs has improved endosomal escape motif compared to the existing endosomal escape motif, and even when the endosomal escape motif was imparted to the heavy-chain variable region and the light-chain variable region, the endosomal escape ability was improved.

Example 38: Confirmation of Improvement in Endosomal Escape Ability of Intact IgG-Format Cytosol-Penetrating Antibody Comprising Heavy-Chain Variable Region Introduced with Improved Endosomal Escape Motif and Light-Chain Variable Region Having Therapeutic Antibody Backbone Imparted with Improved Endosomal Escape Ability In order to confirm that the endosomal escape ability is improved when the endosomal escape motif is imparted to both the heavy-chain variable region and the light-chain variable region, the heavy-chain variable region introduced with the improved endosomal escape motif and the light-chain variable region having the therapeutic antibody backbone imparted with endosomal escape ability were expressed together in HEK293F cell lines and purified.

Specifically, the intact IgG-format cytosol-penetrating antibody comprising the heavy-chain variable region introduced with the improved endosomal escape motif and the light-chain variable region imparted with improved endosomal ability showed no cell penetrating ability. For this reason, an EpCAM-targeting cyclic peptide specific for EpCAM which is overexpressed on the cell membrane surface in various tumors including colorectal cancer was genetically fused to the N-terminus of the antibody by two GGGGS linkers so that the antibody could penetrate cells (US 2015/0246945 A1).

FIG. 33a shows a schematic view showing a process of constructing an intact IgG-format cytosol-penetrating antibody in which an improved endosomal escape motif has been introduced into a heavy-chain variable region thereof and an improved endosomal escape motif has been introduced into a light-chain variable region of a conventional therapeutic antibody fused with an EpCAM-targeting peptide.

Specifically, animal expression vectors encoding a heavy chain comprising the heavy-chain variable region introduced with the improved endosomal escape motif and a light chain comprising the monoclonal antibody light-chain variable region imparted with improved endosomal ability were transiently co-transfected into HEK293F protein-expressing cells in the same manner as described in Example 1. Next, purification of the intact IgG-format cytosol-penetrating antibody was performed in the same manner as described in Example 1.

FIG. 33b shows a bar graph showing the results of observing the cytosolic localization of an intact IgG-format cytosol-penetrating antibody, in which an improved endosomal escape motif has been introduced into a heavy-chain variable region thereof and an improved endosomal escape motif has been introduced into a light-chain variable region of a conventional therapeutic antibody fused with an EpCAM-targeting peptide, by confocal microscopy using calcein and quantifying the calcein fluorescence of the confocal micrographs.

Specifically, human colorectal cancer HCT116 cells having a K-RAS G13D mutation were prepared in the same manner as described in Example 2. The cells were incubated with 0.1, 0.25 and 0.5 µM of each of CT-ep41 and CT01-ep41 at 37° C. for hours. After 4 hours, each well containing PBS or the antibody was treated with 150 µM calcein and incubated at 37° C. for 2 hours. In the same manner as described in Example 2, the cells were washed with PBS and weakly acidic solution, and then fixed. The nucleus was blue-stained with Hoechst33342 and observed with a confocal microscope. In the cells treated with varying concentrations of CT01-ep41, the intensity of green calcein fluorescence localized in the cytosol was stronger than that in the cells treated with CT-ep41.

FIG. 33c shows a graph quantitatively comparing the number of cells that have taken up trypan blue depending on pH by an intact IgG-format cytosol-penetrating antibody in which an improved endosomal escape motif has been introduced into a heavy-chain variable region thereof and an improved endosomal escape motif has been introduced into a light-chain variable region of a conventional therapeutic antibody fused with an EpCAM-targeting peptide.

Specifically, Ramos cells were attached to plates in the same manner as described in Example 5. Then, the cells were incubated with each of 1 µM CT-ep41 and CT01-ep41 0.5 in 200 µl of each of pH 7.4 buffer (HBSS (Welgene), 50 mM HEPES pH 7.4) (for maintaining a cytosolic pH of 7.4) and pH 5.5 buffer (HBSS (Welgene), 50 mM MES pH 5.5) (for maintaining an early endosomal pH of 5.5) at 37° C. for 2 hours. After careful washing with PBS, 200 µl of a mixture of 190 µl of PBS and 10 µl of trypan blue was added to each well, and the cells were observed with a microscope. The number of cells showing trypan blue uptake was counted and expressed as percentage relative to the total number of cells. A total of 400 or more cells were counted, and the mean values are graphically shown. As a result, CT01-ep41 showed a concentration-dependent increase in trypan blue uptake compared to CT-ep41.

Thus, it was confirmed that when the endosomal escape motif was introduced into each of the heavy-chain variable region and the light-chain variable region, the endosomal escape ability was improved compared to when the endosomal escape motif was present only in the light-chain variable region.

Example 39: Logic of Possibility of Imparting Improved Endosomal Escape Motif to Heavy-Chain Variable Region of Conventional Therapeutic Antibody Similar to the logic that the endosomal escape motif was imparted to the light-chain variable region of conventional therapeutic antibodies, the use of the stable backbones of commercially available therapeutic antibody can be expected to increase the overall expression yield. In order to examine whether the endosomal escape motif can operate as a single motif, the endosomal escape motif was also imparted to the heavy-chain variable region of conventional therapeutic antibodies.

Mutants were constructed by substituting the CDR3 of candidate heavy-chain variable regions with the CDR3 of the cytosol-penetrating antibody.

Table 20 below shows the names and sequences of the mutants constructed using a gene synthesis technique.

TABLE 20

| Name of Variable Region | Sequence | SEQ ID NO: |
|---|---|---|
| Humira-01 VH | EVQLVESGGGLVQPGRSLRLSCAASGFTFDDYAMHWVRQAPGKGLEWVSAITWNSGHIDYADSVEGRFTISRDNAKNSLYLQMNSLRAEDTAVYYCAKGWYWMDLWGQGTLVTVSS | SEQ ID NO: 54 |
| Herceptin-01 VH | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRGWYWMDLWGQGTLVTVSS | SEQ ID NO: 55 |
| Avastin-01 VH | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKGWYWMDLWGQGTLVTVSS | SEQ ID NO: 56 |

FIG. 34a is a schematic view showing a process of constructing an intact IgG-format cytosol-penetrating antibody in which an improved endosomal escape motif has been introduced into the heavy-chain variable region of a conventional therapeutic antibody.

In the same manner as described in Example 1, cloning of the heavy-chain variable region was performed, and the resulting heavy chain and the light chain comprising the monoclonal antibody light-chain variable region introduced with the improved endosomal escape motif were expressed together in HEK293F cell lines and purified.

Example 40: Confirmation of Possibility of Imparting Improved Endosomal Escape Motif to Heavy-Chain Variable Region of Monoclonal Antibody FIG. 34b is a graph quantitatively comparing the number of cells that have taken up trypan blue depending on pH by an intact IgG-format cytosol-penetrating antibody in which an improved endosomal escape motif has been introduced into the heavy-chain variable region of a conventional therapeutic antibody.

Specifically, pgsD-677 cells were prepared in the same manner as described in Example 26. Then, in the same manner as in described Example 5, the cells were incubated with 0.5 or 1 µM of each of CT-3, CT-3_WWW, CT01-AAA, CT01_WWW-AAA, and CT01-3, and CT01_WWW-3_WWW in 200 µl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 µl of a mixture of 190 µl of PBS and 10 µl of trypan blue was added to each well, and the cells were observed with a microscope. Next, after careful washing with PBS, the cells were lysed by adding 50 µl of 1% SDS (sodium dodecyl sulfate) to each well. The cells were transferred to a 96-well plate, and the absorbance at 590 nm was measured. All the mutants showed trypan blue uptake similar to that of CT01-ep41.

Example 41: Construction of the Heavy-Chain Variable Region and Light-Chain Variable Region Introduced with Asparaginic Acid for Improving Properties of Cytosol-Penetrating Antibody In order to improve the endosomal escape ability of the cytosol-penetrating antibody, the endosomal escape motif was introduced into the CRD3 of each of the heavy-chain variable region and the light-chain variable region. Due to the hydrophobic amino acids (tryptophan (W) and tyrosine (Y) of the endosomal escape motif, the cytosol-penetrating antibody becomes hydrophobic. To offset this hydrophobicity, mutants were constructed by substituting an amino acid adjacent to the endosomal escape motif with negatively charged asparaginic acid. The mutants were constructed with reference to studies where asparaginic acid was introduced into the backbone and CDR regions of antibody variable regions to increase the overall stability of the antibody and reduce protein aggregation caused by the high hydrophobicity of the antibody (Perchiacca et al., 2011; Dudgeon et al., 2012).

Since the $32^{nd}$, $33^{rd}$ and $58^{th}$ amino acids of the heavy-chain variable region are adjacent to the endosomal escape motif of each of the heavy-chain variable region and the heavy-chain variable region, these amino acids were substituted with asparaginic acid. The resulting amino acids were named CT11 VH (F32D, S33D) or CT12 VH (F32D, S33D, Y58D).

Since the $27b^{th}$, $50^{th}$ and $51^{st}$ amino acids of the light-chain variable region are adjacent to the endosomal escape motif of each of the heavy-chain variable region and the heavy-chain variable region, these amino acids were substituted with asparaginic acid. The resulting amino acids were named hT4-60 VL (L27bD), hT4-61 VL (W50D), hT4-62 VL (W50D, A51D) or hT4-63 VL (L27Bd, W50D, A51D).

Here, the heavy-chain variable region and light-chain variable regions used as templates for the mutants are antibody variable regions introduced with the endosomal escape motif while showing high yields in animal cell expression systems, and these regions were named CT01 VH and hT4-59 VL, respectively.

Tables 21 and 22 below the heavy-chain variable region and light-chain variable mutant sequences obtained by introducing asparaginic acid into the backbone and CDR regions of the antibody variable region.

TABLE 21

| Name of Variable Region | Sequence | SEQ ID NO: |
|---|---|---|
| CT10 VH |         10        20        30        40        50 52a<br>EVQLVESGGGLVQPGGSLRLSCAASGFTFSDFSMSWVRQAPGKGLEWVSYISRTSHTTY<br>     60        70      80 82a     90      100a      110<br>YADSVKGRFTISRDNSKNTLYLQMNSLRAEDTAVYYCARGWYWMDLWGQGTLVTVSS | SEQ ID NO: 57 |
| CT11 VH |         10        20        30        40        50 52a<br>EVQLVESGGGLVQPGGSLRLSCAASGFTDDDFSMSWVRQAPGKGLEWVSYISRTSHTTY<br>     60        70      80 82a     90      100a      110<br>YADSVKGRFTISRDNSKNTLYLQMNSLRAEDTAVYYCARGWYWMDLWGQGTLVTVSS | SEQ ID NO: 58 |
| CT12 VH |         10        20        30        40        50 52a<br>EVQLVESGGGLVQPGGSLRLSCAASGFTDDDFSMSWVRQAPGKGLEWVSYISRTSHTTD<br>     60        70      80 82a     90      100a      110<br>YADSVKGRFTISRDNSKNTLYLQMNSLRAEDTAVYYCARGWYWMDLWGQGTLVTVSS | SEQ ID NO: 59 |

TABLE 22

| Name of Variable Region | Sequence | SEQ ID NO: |
|---|---|---|
| hT4-59 VL | 1        10        20     abcdef   30        40        50<br>DIQMTQSPSSLSASVGDRVTITCKSSQSLLNSRDGKNYLAWYQQKPGKAPKLLIYW<br>     60        70        80        90       100<br>ASTRESGVPSRFSGSGSGTDFTLTISSLQPEDFATYFCQQYWYWMYTFGQGTKVEIKR | SEQ ID NO: 60 |
| hT4-60 VL | 1        10        20     abcdef   30        40        50<br>DIQMTQSPSSLSASVGDRVTITCKSSQSDLNSRDGKNYLAWYQQKPGKAPKLLIYW<br>     60        70        80        90       100<br>ASTRESGVPSRFSGSGSGTDFTLTISSLQPEDFATYFCQQYWYWMYTFGQGTKVEIKR | SEQ ID NO: 61 |
| hT4-61 VL | 1        10        20     abcdef   30        40        50<br>DIQMTQSPSSLSASVGDRVTITCKSSQSLLNSRDGKNYLAWYQQKPGKAPKLLIYD<br>     60        70        80        90       100<br>ASTRESGVPSRFSGSGSGTDFTLTISSLQPEDFATYFCQQYWYWMYTFGQGTKVEIKR | SEQ ID NO: 62 |
| hT4-62 VL | 1        10        20     abcdef   30        40        50<br>DIQMTQSPSSLSASVGDRVTITCKSSQSLLNSRDGKNYLAWYQQKPGKAPKLLIYD<br>     60        70        80        90       100<br>DSTRESGVPSRFSGSGSGTDFTLTISSLQPEDFATYFCQQYWYWMYTFGQGTKVEIKR | SEQ ID NO: 63 |
| hT4-63 VL | 1        10        20     abcdef   30        40        50<br>DIQMTQSPSSLSASVGDRVTITCKSSQSDLNSRDGKNYLAWYQQKPGKAPKLLIYD<br>     60        70        80        90       100<br>DSTRESGVPSRFSGSGSGTDFTLTISSLQPEDFATYFCQQYWYWMYTFGQGTKVEIKR | SEQ ID NO: 64 |

In the same manner as described in Example 1, cloning of each heavy-chain variable region was performed, and the resulting heavy chain and the light chain comprising the monoclonal antibody light-chain variable region introduced with the improved endosomal escape motif were expressed together in HEK293F cell lines and purified.

Example 42: Confirmation of Improvement in Endosomal Escape Ability of Intact IgG-Format Cytosol-Penetrating Antibody Comprising the Heavy-Chain Variable Region and/or Light-Chain Variable Region Introduced with Asparaginic Acid FIG. 35 is a graph quantitatively comparing the number of cells that have taken up trypan blue depending on pH by an intact IgG-format cytosol-penetrating antibody comprising a light-chain variable region and/or a heavy-chain variable region introduced with asparaginic acid.

Specifically, pgsD-677 cells were prepared in the same manner as described in Example 26. Then, in the same manner as in described Example 5, the cells were incubated with 1 μM of each of CT10-ep59, CT11-ep59, CT12-ep59, CT10-ep60, CT10-ep61, CT10-ep62, CT10-ep63, and CT12-ep63 in 200 µl of each of pH 7.4 buffer (HBSS (Welgene), 50 mM HEPES pH 7.4 (cytosolic pH)) and pH 5.5 buffer (HBSS (Welgene), 50 mM MES pH 5.5 (early endosomal pH)) at 37° C. for 2 hours. After careful washing with PBS, 200 µl of a mixture of 190 µl of PBS and 10 µl of trypan blue was added to each well, and the cells were observed with a microscope. Next, after careful washing with PBS, the cells were lysed by adding 50 µl of 1% SDS (sodium dodecyl sulfate) to each well. The cells were transferred to a 96-well plate, and the absorbance at 590 nm was measured. All the mutants showed trypan blue uptake similar to that of CT01-ep41 tested in the above Example. This suggests that even when asparaginic acid is introduced, the endosomal escape ability is not reduced. Antibody stability experiments for these antibodies will be carried out later.

Example 43: Analysis of Structure of Cytosol-Penetrating Antibody

In order to identify the structures of the IgG-format cytosol-penetrating antibodies, the CT-59 antibody showing a very high production yield was used among the cytosol-penetrating antibodies having endosomal escape ability at endosomal acidic pH conditions. This antibody is an IgG-format cytosol-penetrating antibody comprising hT0 VH and hT4-59 VL as the heavy-chain variable region and the light-chain variable region, respectively.

To identify the three-dimensional structure, IgG-format CT-59 produced using HEK293 cells was treated with papain, and then high-purity Fab was purified by protein A column and size exclusion chromatography. Next, a crystal for structural identification was formed using an Mosquito-LCP system under screening buffer index G1 conditions (0.2 M NaCl, 0.1 M Tris, pH 8.5, 25% (w/v) PEG3350). When the cytosol-penetrating antibody was mixed with the screening buffer, the final pH was 8.1.

FIG. 36a shows the results of observing a crystal of CT-Fab, formed under Index G1 conditions, by RI1000 (Rock Imager1000; automatic protein crystal image analysis system).

X-ray diffraction data were collected at the 5C beamline (Pohang Accelerator Laboratory(PAL)), and indexing and scaling were performed using the HKL2000 package (HKL Research Inc., USA), and then the Initial electron density map of CT-59 Fab was obtained by a molecular replacement (MR) method. The three-dimensional structure data of a protein having a similar structure to that of CT-59 is required to use the MR method, and a structure model obtained through the FFAS site (ffas.sanfordburnham.org/ffas-cgi/cgi/ffas.pl) was used as a model. Initial phase information of CT-59 Fab was obtained using CCP4. Based on the obtained initial phase information, a model building operation was performed using COOT (Crystallographic Object-Oriented Toolkit, www.biop.ox.ac.uk/coot/)), and refinement and validation operations were performed using Refmac5 (www.ccp4.ac.uk/html/refmac5.html) and PHENIX (Python-based Hierarchical ENvironment for Integrated Xtallography, www.phenix-online.org/) software (see FIG. 36b).

As a result, at a final pH of pH 8.1, a three-dimensional structure with a high resolution of 1.8 Å was observed. It was found that the distance between the $1^{st}$ asparaginic acid (D) of the light-chain variable region of CT-59 and the side chain of the $95^{th}$ methionine (M) of the light-chain variable region was 6.87 Å.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

---

SEQUENCE LISTING

<160> NUMBER OF SEQ ID NOS: 122

<210> SEQ ID NO 1
<211> LENGTH: 114
<212> TYPE: PRT
<213> ORGANISM: Artificial Sequence
<220> FEATURE:
<223> OTHER INFORMATION: hT4-WWH VL

<400> SEQUENCE: 1

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Trp His Met Tyr Thr Phe Gly Gln Gly Thr Lys Val Glu Ile
            100                 105                 110
```

Lys Arg

<210> SEQ ID NO 2
<211> LENGTH: 114
<212> TYPE: PRT
<213> ORGANISM: Artificial Sequence
<220> FEATURE:
<223> OTHER INFORMATION: hT4-WYW VL

<400> SEQUENCE: 2

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr Trp Met Tyr Thr Phe Gly Gln Gly Thr Lys Val Glu Ile
            100                 105                 110

Lys Arg

<210> SEQ ID NO 3
<211> LENGTH: 114
<212> TYPE: PRT
<213> ORGANISM: Artificial Sequence
<220> FEATURE:
<223> OTHER INFORMATION: hT4-YWW VL

<400> SEQUENCE: 3

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Trp Trp Met Tyr Thr Phe Gly Gln Gly Thr Lys Val Glu Ile
            100                 105                 110

Lys Arg

<210> SEQ ID NO 4
<211> LENGTH: 114
<212> TYPE: PRT
<213> ORGANISM: Artificial Sequence
<220> FEATURE:
<223> OTHER INFORMATION: hT4-WYH VL

<400> SEQUENCE: 4

-continued

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr His Met Tyr Thr Phe Gly Gln Gly Thr Lys Val Glu Ile
            100                 105                 110

Lys Arg

<210> SEQ ID NO 5
<211> LENGTH: 114
<212> TYPE: PRT
<213> ORGANISM: Artificial Sequence
<220> FEATURE:
<223> OTHER INFORMATION: hT4-YWH VL

<400> SEQUENCE: 5

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Trp His Met Tyr Thr Phe Gly Gln Gly Thr Lys Val Glu Ile
            100                 105                 110

Lys Arg

<210> SEQ ID NO 6
<211> LENGTH: 17
<212> TYPE: PRT
<213> ORGANISM: Artificial Sequence
<220> FEATURE:
<223> OTHER INFORMATION: CDR1

<400> SEQUENCE: 6

Lys Ser Ser Gln Ser Leu Phe Asn Ser Arg Thr Arg Lys Asn Tyr Leu
1               5                   10                  15

Ala

<210> SEQ ID NO 7
<211> LENGTH: 7
<212> TYPE: PRT
<213> ORGANISM: Artificial Sequence
<220> FEATURE:
<223> OTHER INFORMATION: CDR2

```
<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: hT4-WWH VL

<400> SEQUENCE: 8

Gln Gln Tyr Trp Trp His Met Tyr Thr
1               5

<210> SEQ ID NO 9
<211> LENGTH: 9
<212> TYPE: PRT
<213> ORGANISM: Artificial Sequence
<220> FEATURE:
<223> OTHER INFORMATION: hT4-WYW VL

<400> SEQUENCE: 9

Gln Gln Tyr Trp Tyr Trp Met Tyr Thr
1               5

<210> SEQ ID NO 10
<211> LENGTH: 9
<212> TYPE: PRT
<213> ORGANISM: Artificial Sequence
<220> FEATURE:
<223> OTHER INFORMATION: hT4-YWW VL

<400> SEQUENCE: 10

Gln Gln Tyr Tyr Trp Trp Met Tyr Thr
1               5

<210> SEQ ID NO 11
<211> LENGTH: 9
<212> TYPE: PRT
<213> ORGANISM: Artificial Sequence
<220> FEATURE:
<223> OTHER INFORMATION: hT4-WYH VL

<400> SEQUENCE: 11

Gln Gln Tyr Trp Tyr His Met Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: hT4-YWH VL

<400> SEQUENCE: 12

Gln Gln Tyr Tyr Trp His Met Tyr Thr
1               5

<210> SEQ ID NO 13
<211> LENGTH: 114
<212> TYPE: PRT
<213> ORGANISM: Artificial Sequence
<220> FEATURE:
<223> OTHER INFORMATION: hT4-RYR VL

<400> SEQUENCE: 13
```

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Arg Tyr Arg Met Tyr Thr Phe Gly Gln Gly Thr Lys Val Glu Ile
                100                 105                 110

Lys Arg

<210> SEQ ID NO 14
<211> LENGTH: 114
<212> TYPE: PRT
<213> ORGANISM: Artificial Sequence
<220> FEATURE:
<223> OTHER INFORMATION: hT4-IYI VL

<400> SEQUENCE: 14

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Ile Tyr Ile Met Tyr Thr Phe Gly Gln Gly Thr Lys Val Glu Ile
                100                 105                 110

Lys Arg

<210> SEQ ID NO 15
<211> LENGTH: 114
<212> TYPE: PRT
<213> ORGANISM: Artificial Sequence
<220> FEATURE:
<223> OTHER INFORMATION: hT4-GYG VL

<400> SEQUENCE: 15

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Gly Tyr Gly Met Tyr Thr Phe Gly Gln Gly Thr Lys Val Glu Ile
            100                 105                 110

Lys Arg

<210> SEQ ID NO 16
<211> LENGTH: 114
<212> TYPE: PRT
<213> ORGANISM: Artificial Sequence
<220> FEATURE:
<223> OTHER INFORMATION: hT4-3 VL

<400> SEQUENCE: 16

Asp Leu Val Met Thr Gln Ser Pro Ser Ser Leu Ser Ala Ser Val Gly
 1               5                  10                  15

Asp Arg Val Thr Ile Thr Cys Lys Ser Ser Gln Ser Leu Phe Asn Ser
                 20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Phe Cys Gln Gln
                 85                  90                  95

Tyr Trp Tyr Trp Met Tyr Thr Phe Gly Gln Gly Thr Lys Val Glu Ile
            100                 105                 110

Lys Arg

<210> SEQ ID NO 17
<211> LENGTH: 114
<212> TYPE: PRT
<213> ORGANISM: Artificial Sequence
<220> FEATURE:
<223> OTHER INFORMATION: hT4-3 D1E-M95L VL

<400> SEQUENCE: 17

Glu Leu Val Met Thr Gln Ser Pro Ser Ser Leu Ser Ala Ser Val Gly
 1               5                  10                  15

Asp Arg Val Thr Ile Thr Cys Lys Ser Ser Gln Ser Leu Phe Asn Ser
                 20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Trp Tyr Trp Leu Tyr Thr Phe Gly Gln Gly Thr Lys Val Glu Ile
            100                 105                 110

Lys Arg

<210> SEQ ID NO 18
```

<211> LENGTH: 114
<212> TYPE: PRT
<213> ORGANISM: Artificial Sequence
<220> FEATURE:
<223> OTHER INFORMATION: hT4-3 Y91H VL

<400> SEQUENCE: 18

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Trp Tyr Trp Met Tyr Thr Phe Gly Gln Gly Thr Lys Val Glu Ile
            100                 105                 110

Lys Arg
```

<210> SEQ ID NO 19
<211> LENGTH: 114
<212> TYPE: PRT
<213> ORGANISM: Artificial Sequence
<220> FEATURE:
<223> OTHER INFORMATION: hT4-3 Y91D VL

<400> SEQUENCE: 19

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Asp Trp Tyr Trp Met Tyr Thr Phe Gly Gln Gly Thr Lys Val Glu Ile
            100                 105                 110

Lys Arg
```

<210> SEQ ID NO 20
<211> LENGTH: 114
<212> TYPE: PRT
<213> ORGANISM: Artificial Sequence
<220> FEATURE:
<223> OTHER INFORMATION: hT4-3 L2E Q90L VL

<400> SEQUENCE: 20

```
Asp Glu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30
```

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Leu
                 85                  90                  95

Tyr Trp Tyr Trp Met Tyr Thr Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: hT4-3 L2E T97I VL

<400> SEQUENCE: 21

Asp Glu Val Met Thr Gln Ser Pro Ser Ser Leu Ser Ala Ser Val Gly
 1               5                  10                  15

Asp Arg Val Thr Ile Thr Cys Lys Ser Gln Ser Leu Phe Asn Ser
             20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Trp Tyr Trp Met Tyr Ile Phe Gly Gln Gly Thr Lys Val Glu Ile
            100                 105                 110

Lys Arg

<210> SEQ ID NO 22
<211> LENGTH: 114
<212> TYPE: PRT
<213> ORGANISM: Artificial Sequence
<220> FEATURE:
<223> OTHER INFORMATION: hT4-3 Q90H M95A VL

<400> SEQUENCE: 22

Asp Leu Val Met Thr Gln Ser Pro Ser Ser Leu Ser Ala Ser Val Gly
 1               5                  10                  15

Asp Arg Val Thr Ile Thr Cys Lys Ser Gln Ser Leu Phe Asn Ser
             20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln His
                 85                  90                  95

Tyr Trp Tyr Trp Ala Tyr Thr Phe Gly Gln Gly Thr Lys Val Glu Ile
            100                 105                 110

Lys Arg

<210> SEQ ID NO 23
<211> LENGTH: 114
<212> TYPE: PRT
<213> ORGANISM: Artificial Sequence
<220> FEATURE:
<223> OTHER INFORMATION: hT4-3 Q90H VL

<400> SEQUENCE: 23

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln His
                85                  90                  95

Tyr Trp Tyr Trp Met Tyr Thr Phe Gly Gln Gly Thr Lys Val Glu Ile
            100                 105                 110

Lys Arg

<210> SEQ ID NO 24
<211> LENGTH: 9
<212> TYPE: PRT
<213> ORGANISM: Artificial Sequence
<220> FEATURE:
<223> OTHER INFORMATION: hT4 3 Q90H VL

<400> SEQUENCE: 24

Gln His Tyr Trp Tyr Trp Met Tyr Thr
1               5

<210> SEQ ID NO 25
<211> LENGTH: 113
<212> TYPE: PRT
<213> ORGANISM: Artificial Sequence
<220> FEATURE:
<223> OTHER INFORMATION: hT4-3 L8-1 VL

<400> SEQUENCE: 25

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

```
Tyr Trp Tyr Trp Met Thr Phe Gly Gln Gly Thr Lys Val Glu Ile Lys
                100                 105                 110

Arg
```

\<210\> SEQ ID NO 26
\<211\> LENGTH: 113
\<212\> TYPE: PRT
\<213\> ORGANISM: Artificial Sequence
\<220\> FEATURE:
\<223\> OTHER INFORMATION: hT4-3 L8-2 VL

\<400\> SEQUENCE: 26

```
Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Trp Tyr Trp Met Pro Thr Phe Gly Gln Gly Thr Lys Val Glu Ile Lys
                100                 105                 110

Arg
```

\<210\> SEQ ID NO 27
\<211\> LENGTH: 115
\<212\> TYPE: PRT
\<213\> ORGANISM: Artificial Sequence
\<220\> FEATURE:
\<223\> OTHER INFORMATION: hT4-3 L10-1 VL

\<400\> SEQUENCE: 27

```
Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Pro Met Tyr Thr Phe Gly Gln Gly Thr Lys Val Glu
                100                 105                 110

Ile Lys Arg
        115
```

\<210\> SEQ ID NO 28
\<211\> LENGTH: 115
\<212\> TYPE: PRT
\<213\> ORGANISM: Artificial Sequence
\<220\> FEATURE:
\<223\> OTHER INFORMATION: hT4-3 L10-2 VL

<400> SEQUENCE: 28

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr Trp Leu Met Tyr Thr Phe Gly Gln Gly Thr Lys Val Glu
                100                 105                 110

Ile Lys Arg
        115

<210> SEQ ID NO 29
<211> LENGTH: 115
<212> TYPE: PRT
<213> ORGANISM: Artificial Sequence
<220> FEATURE:
<223> OTHER INFORMATION: hT4-3 L10-3 VL

<400> SEQUENCE: 29

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr Trp Tyr Met Tyr Thr Phe Gly Gln Gly Thr Lys Val Glu
                100                 105                 110

Ile Lys Arg
        115

<210> SEQ ID NO 30
<211> LENGTH: 116
<212> TYPE: PRT
<213> ORGANISM: Artificial Sequence
<220> FEATURE:
<223> OTHER INFORMATION: hT4-3 L11-1 VL

<400> SEQUENCE: 30

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr Trp Leu Tyr Met Tyr Thr Phe Gly Gln Gly Thr Lys Val
            100                 105                 110

Glu Ile Lys Arg
        115

<210> SEQ ID NO 31
<211> LENGTH: 116
<212> TYPE: PRT
<213> ORGANISM: Artificial Sequence
<220> FEATURE:
<223> OTHER INFORMATION: hT4-3 L11-2 VL

<400> SEQUENCE: 31

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Pro Trp Tyr Trp Pro Met Tyr Thr Phe Gly Gln Gly Thr Lys Val
            100                 105                 110

Glu Ile Lys Arg
        115

<210> SEQ ID NO 32
<211> LENGTH: 108
<212> TYPE: PRT
<213> ORGANISM: Artificial Sequence
<220> FEATURE:
<223> OTHER INFORMATION: Necitumumab-WYW VL

<400> SEQUENCE: 32

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Tyr Trp Tyr Trp Met Tyr
                85                  90                  95

Thr Phe Gly Gln Gly Thr Lys Ala Glu Ile Lys Arg

<210> SEQ ID NO 33
<211> LENGTH: 108
<212> TYPE: PRT
<213> ORGANISM: Artificial Sequence
<220> FEATURE:
<223> OTHER INFORMATION: Panitumumab-WYW VL

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Trp Tyr Trp Met Tyr
                85                  90                  95

Thr Phe Gly Gly Gly Thr Lys Val Glu Ile Lys Arg
            100                 105

<210> SEQ ID NO 34
<211> LENGTH: 114
<212> TYPE: PRT
<213> ORGANISM: Artificial Sequence
<220> FEATURE:
<223> OTHER INFORMATION: Lumretuzumab-WYW VL

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Trp Tyr Trp Met Tyr Thr Phe Gly Gln Gly Thr Lys Leu Glu Ile
            100                 105                 110

Lys Arg

<210> SEQ ID NO 35
<211> LENGTH: 113
<212> TYPE: PRT
<213> ORGANISM: Artificial Sequence
<220> FEATURE:
<223> OTHER INFORMATION: Nimotuzumab-WYW VL

<400> SEQUENCE: 35

Asp Ile Gln Met Thr Gln Ser Pro Ser Ser Leu Ser Ala Ser Val Gly
1               5                   10                  15

```
Asp Arg Val Thr Ile Thr Cys Arg Ser Ser Gln Asn Ile Val His Ser
                20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Phe Cys Gln Gln Tyr
                85                  90                  95

Trp Tyr Trp Met Tyr Thr Phe Gly Gln Gly Thr Lys Leu Gln Ile Thr
                100                 105                 110

Arg

<210> SEQ ID NO 36
<211> LENGTH: 109
<212> TYPE: PRT
<213> ORGANISM: Artificial Sequence
<220> FEATURE:
<223> OTHER INFORMATION: Emibetuzumab-WYW VL

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Phe Cys Gln Gln Tyr Trp Tyr Trp Met
                85                  90                  95

Tyr Thr Phe Gly Gly Gly Thr Lys Val Glu Ile Lys Arg
            100                 105

<210> SEQ ID NO 37
<211> LENGTH: 108
<212> TYPE: PRT
<213> ORGANISM: Artificial Sequence
<220> FEATURE:
<223> OTHER INFORMATION: Pertuzumab-WYW VL

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Trp Tyr Trp Met Tyr
                85                  90                  95
```

```
Thr Phe Gly Gln Gly Thr Lys Val Glu Ile Lys Arg
            100                 105

<210> SEQ ID NO 38
<211> LENGTH: 120
<212> TYPE: PRT
<213> ORGANISM: Artificial Sequence
<220> FEATURE:
<223> OTHER INFORMATION: HT0 VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Lys Arg Gly Tyr Ala Met Asp Tyr Trp Gly Gln
            100                 105                 110

Gly Thr Thr Val Thr Val Ser Ser
        115                 120

<210> SEQ ID NO 39
<211> LENGTH: 116
<212> TYPE: PRT
<213> ORGANISM: Artificial Sequence
<220> FEATURE:
<223> OTHER INFORMATION: HT0-01 VH

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Thr Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: HT0-02 VH
```

```
<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Phe Asp Leu Trp Gly Gln Gly Thr Thr Val
            100                 105                 110

Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: HT0-03 VH

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Gly Phe Asp Leu Trp Gly Gln Gly Thr Thr
            100                 105                 110

Val Thr Val Ser Ser
        115

<210> SEQ ID NO 42
<211> LENGTH: 116
<212> TYPE: PRT
<213> ORGANISM: Artificial Sequence
<220> FEATURE:
<223> OTHER INFORMATION: HT0-04 VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45
```

```
Ser Ala Ile Asn Pro Tyr Asn Asp Gly Asn Tyr Tyr Ala Asp Ser Val
    50                  55                  60

Lys Gly Arg Phe Thr Ile Ser Arg Asp Asn Ser Arg Lys Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Tyr Trp Met Asp Leu Trp Gly Gln Gly Thr Thr Val
                100                 105                 110

Thr Val Ser Ser
        115

<210> SEQ ID NO 43
<211> LENGTH: 5
<212> TYPE: PRT
<213> ORGANISM: Artificial Sequence
<220> FEATURE:
<223> OTHER INFORMATION: CDR1

<400> SEQUENCE: 43

Ser Tyr Val Met His
1               5

<210> SEQ ID NO 44
<211> LENGTH: 17
<212> TYPE: PRT
<213> ORGANISM: Artificial Sequence
<220> FEATURE:
<223> OTHER INFORMATION: CDR2

<400> SEQUENCE: 44

Ala Ile Asn Pro Tyr Asn Asp Gly Asn Tyr Tyr Ala Asp Ser Val Lys
1               5                   10                  15

Gly

<210> SEQ ID NO 45
<211> LENGTH: 11
<212> TYPE: PRT
<213> ORGANISM: Artificial Sequence
<220> FEATURE:
<223> OTHER INFORMATION: HT0 VH

<400> SEQUENCE: 45

Gly Ala Arg Lys Arg Gly Tyr Ala Met Asp Tyr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: HT0-01 VH

<400> SEQUENCE: 46

Gly Trp Tyr Trp Met Asp Leu
1               5

<210> SEQ ID NO 47
<211> LENGTH: 7
<212> TYPE: PRT
<213> ORGANISM: Artificial Sequence
<220> FEATURE:
<223> OTHER INFORMATION: HT0-02 VH

<400> SEQUENCE: 47
```

```
Gly Trp Tyr Trp Phe Asp Leu
1               5
```

<210> SEQ ID NO 48
<211> LENGTH: 8
<212> TYPE: PRT
<213> ORGANISM: Artificial Sequence
<220> FEATURE:
<223> OTHER INFORMATION: HT0-03 VH

<400> SEQUENCE: 48

```
Gly Trp Tyr Trp Gly Phe Asp Leu
1               5
```

<210> SEQ ID NO 49
<211> LENGTH: 7
<212> TYPE: PRT
<213> ORGANISM: Artificial Sequence
<220> FEATURE:
<223> OTHER INFORMATION: HT0-04 VH

<400> SEQUENCE: 49

```
Tyr Trp Tyr Trp Met Asp Leu
1               5
```

<210> SEQ ID NO 50
<211> LENGTH: 114
<212> TYPE: PRT
<213> ORGANISM: Artificial Sequence
<220> FEATURE:
<223> OTHER INFORMATION: hT4-3 WWW VL

<400> SEQUENCE: 50

```
Asp Leu Val Met Thr Gln Ser Pro Ser Leu Ser Ala Ser Val Gly
1               5                   10                  15

Asp Arg Val Thr Ile Thr Cys Lys Ser Gln Ser Leu Phe Asn Ser
                20                  25                  30

Arg Thr Arg Lys Asn Tyr Leu Ala Trp Tyr Gln Lys Pro Gly Lys
        35                  40                  45

Ala Pro Lys Leu Leu Ile Tyr Trp Ala Ser Thr Arg Glu Ser Gly Val
50                      55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Trp Trp Met Tyr Thr Phe Gly Gln Gly Thr Lys Val Glu Ile
            100                 105                 110

Lys Arg
```

<210> SEQ ID NO 51
<211> LENGTH: 9
<212> TYPE: PRT
<213> ORGANISM: Artificial Sequence
<220> FEATURE:
<223> OTHER INFORMATION: hT4 3 WWW VL

<400> SEQUENCE: 51

```
Gln Gln Tyr Trp Trp Trp Met Tyr Thr
1               5
```

<210> SEQ ID NO 52
<211> LENGTH: 116
<212> TYPE: PRT

<213> ORGANISM: Artificial Sequence
<220> FEATURE:
<223> OTHER INFORMATION: HT0-01 WWW VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Trp Trp Met Asp Leu Trp Gly Gln Gly Thr Thr Val
            100                 105                 110

Thr Val Ser Ser
        115

<210> SEQ ID NO 53
<211> LENGTH: 7
<212> TYPE: PRT
<213> ORGANISM: Artificial Sequence
<220> FEATURE:
<223> OTHER INFORMATION: HT0-01 WWW VH

<400> SEQUENCE: 53

Gly Trp Trp Trp Met Asp Leu
1               5

<210> SEQ ID NO 54
<211> LENGTH: 116
<212> TYPE: PRT
<213> ORGANISM: Artificial Sequence
<220> FEATURE:
<223> OTHER INFORMATION: Humira-01 VH

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Tyr Trp Met Asp Leu Trp Gly Gln Gly Thr Leu Val
            100                 105                 110

Thr Val Ser Ser
        115

<210> SEQ ID NO 55

-continued

```
<211> LENGTH: 116
<212> TYPE: PRT
<213> ORGANISM: Artificial Sequence
<220> FEATURE:
<223> OTHER INFORMATION: Herceptin-01 VH

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Trp Tyr Trp Met Asp Leu Trp Gly Gln Gly Thr Leu Val
            100                 105                 110

Thr Val Ser Ser
        115

<210> SEQ ID NO 56
<211> LENGTH: 116
<212> TYPE: PRT
<213> ORGANISM: Artificial Sequence
<220> FEATURE:
<223> OTHER INFORMATION: Avastin-01 VH

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Gly Trp Tyr Trp Met Asp Leu Trp Gly Gln Gly Thr Leu Val
            100                 105                 110

Thr Val Ser Ser
        115

<210> SEQ ID NO 57
<211> LENGTH: 116
<212> TYPE: PRT
<213> ORGANISM: Artificial Sequence
<220> FEATURE:
<223> OTHER INFORMATION: CT10 VH

<400> SEQUENCE: 57

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Phe
            20                  25                  30

Ser Met Ser Trp Val Arg Gln Ala Pro Gly Lys Gly Leu Glu Trp Val
            35                  40                  45

Ser Tyr Ile Ser Arg Thr Ser His Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Leu Val
            100                 105                 110

Thr Val Ser Ser
            115

<210> SEQ ID NO 58
<211> LENGTH: 116
<212> TYPE: PRT
<213> ORGANISM: Artificial Sequence
<220> FEATURE:
<223> OTHER INFORMATION: CT11 VH

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Asp Asp Phe
            20                  25                  30

Ser Met Ser Trp Val Arg Gln Ala Pro Gly Lys Gly Leu Glu Trp Val
            35                  40                  45

Ser Tyr Ile Ser Arg Thr Ser His Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Leu Val
            100                 105                 110

Thr Val Ser Ser
            115

<210> SEQ ID NO 59
<211> LENGTH: 116
<212> TYPE: PRT
<213> ORGANISM: Artificial Sequence
<220> FEATURE:
<223> OTHER INFORMATION: CT12 VH

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Asp Asp Phe
            20                  25                  30

Ser Met Ser Trp Val Arg Gln Ala Pro Gly Lys Gly Leu Glu Trp Val
            35                  40                  45

Ser Tyr Ile Ser Arg Thr Ser His Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Leu Val
            100                 105                 110

Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: hT4-59 VL

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
            100                 105                 110

Lys Arg

<210> SEQ ID NO 61
<211> LENGTH: 114
<212> TYPE: PRT
<213> ORGANISM: Artificial Sequence
<220> FEATURE:
<223> OTHER INFORMATION: hT4-60 VL

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Asp Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
            100                 105                 110

Lys Arg

<210> SEQ ID NO 62
<211> LENGTH: 114
```

```
<212> TYPE: PRT
<213> ORGANISM: Artificial Sequence
<220> FEATURE:
<223> OTHER INFORMATION: hT4-61 VL

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Asp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
                100                 105                 110

Lys Arg

<210> SEQ ID NO 63
<211> LENGTH: 114
<212> TYPE: PRT
<213> ORGANISM: Artificial Sequence
<220> FEATURE:
<223> OTHER INFORMATION: hT4-62 VL

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Asp Asp Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
                100                 105                 110

Lys Arg

<210> SEQ ID NO 64
<211> LENGTH: 114
<212> TYPE: PRT
<213> ORGANISM: Artificial Sequence
<220> FEATURE:
<223> OTHER INFORMATION: hT4-63 VL

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Ser Asp Leu Asn Ser
            20                  25                  30
```

Arg Asp Gly Lys Asn Tyr Leu Ala Trp Tyr Gln Gln Lys Pro Gly Lys
            35                  40                  45

Ala Pro Lys Leu Leu Ile Tyr Asp Asp Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Phe Cys Gln Gln
                 85                  90                  95

Tyr Trp Tyr Trp Met Tyr Thr Phe Gly Gln Gly Thr Lys Val Glu Ile
                100                 105                 110

Lys Arg

<210> SEQ ID NO 65
<211> LENGTH: 114
<212> TYPE: PRT
<213> ORGANISM: Artificial Sequence
<220> FEATURE:
<223> OTHER INFORMATION: hT4 VL

<400> SEQUENCE: 65

Asp Leu Val Met Thr Gln Ser Pro Ser Ser Leu Ser Ala Ser Val Gly
 1                   5                  10                  15

Asp Arg Val Thr Ile Thr Cys Lys Ser Ser Gln Ser Leu Phe Asn Ser
                 20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Tyr His Met Tyr Thr Phe Gly Gln Gly Thr Lys Val Glu Ile
                100                 105                 110

Lys Arg

<210> SEQ ID NO 66
<211> LENGTH: 114
<212> TYPE: PRT
<213> ORGANISM: Artificial Sequence
<220> FEATURE:
<223> OTHER INFORMATION: hT4-D1A VL

<400> SEQUENCE: 66

Ala Leu Val Met Thr Gln Ser Pro Ser Ser Leu Ser Ala Ser Val Gly
 1                   5                  10                  15

Asp Arg Val Thr Ile Thr Cys Lys Ser Ser Gln Ser Leu Phe Asn Ser
                 20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Tyr His Met Tyr Thr Phe Gly Gln Gly Thr Lys Val Glu Ile

Lys Arg

<210> SEQ ID NO 67
<211> LENGTH: 114
<212> TYPE: PRT
<213> ORGANISM: Artificial Sequence
<220> FEATURE:
<223> OTHER INFORMATION: hT4-M95A VL

<400> SEQUENCE: 67

```
Asp Leu Val Met Thr Gln Ser Pro Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Tyr His Ala Tyr Thr Phe Gly Gln Gly Thr Lys Val Glu Ile
                100                 105                 110
```

Lys Arg

<210> SEQ ID NO 68
<211> LENGTH: 114
<212> TYPE: PRT
<213> ORGANISM: Artificial Sequence
<220> FEATURE:
<223> OTHER INFORMATION: hT4-D1E VL

<400> SEQUENCE: 68

```
Glu Leu Val Met Thr Gln Ser Pro Ser Leu Ser Ala Ser Val Gly
1               5                   10                  15

Asp Arg Val Thr Ile Thr Cys Lys Ser Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Tyr His Met Tyr Thr Phe Gly Gln Gly Thr Lys Val Glu Ile
                100                 105                 110
```

Lys Arg

<210> SEQ ID NO 69
<211> LENGTH: 112
<212> TYPE: PRT
<213> ORGANISM: Artificial Sequence
<220> FEATURE:
<223> OTHER INFORMATION: hT4-M95L VL

<400> SEQUENCE: 69

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Tyr His Leu Tyr Thr Phe Gly Gln Gly Thr Lys Val Glu Ile
            100                 105                 110
```

<210> SEQ ID NO 70
<211> LENGTH: 114
<212> TYPE: PRT
<213> ORGANISM: Artificial Sequence
<220> FEATURE:
<223> OTHER INFORMATION: hT4-Y91A VL

<400> SEQUENCE: 70

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ala Tyr Tyr His Met Tyr Thr Phe Gly Gln Gly Thr Lys Val Glu Ile
            100                 105                 110

Lys Arg
```

<210> SEQ ID NO 71
<211> LENGTH: 114
<212> TYPE: PRT
<213> ORGANISM: Artificial Sequence
<220> FEATURE:
<223> OTHER INFORMATION: hT4-Y92A VL

<400> SEQUENCE: 71

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80
```

```
Ile Ser Ser Leu Gln Pro Glu Asp Phe Ala Thr Tyr Tyr Cys Gln Gln
                85                  90                  95

Tyr Ala Tyr His Met Tyr Thr Phe Gly Gln Gly Thr Lys Val Glu Ile
            100                 105                 110

Lys Arg

<210> SEQ ID NO 72
<211> LENGTH: 114
<212> TYPE: PRT
<213> ORGANISM: Artificial Sequence
<220> FEATURE:
<223> OTHER INFORMATION: hT4-Y93A VL

<400> SEQUENCE: 72

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala His Met Tyr Thr Phe Gly Gln Gly Thr Lys Val Glu Ile
            100                 105                 110

Lys Arg

<210> SEQ ID NO 73
<211> LENGTH: 114
<212> TYPE: PRT
<213> ORGANISM: Artificial Sequence
<220> FEATURE:
<223> OTHER INFORMATION: hT4-H94A VL

<400> SEQUENCE: 73

Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
                20                  25                  30

Arg Thr Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Tyr Ala Met Tyr Thr Phe Gly Gln Gly Thr Lys Val Glu Ile
            100                 105                 110

Lys Arg

<210> SEQ ID NO 74
<211> LENGTH: 114
<212> TYPE: PRT
```

<213> ORGANISM: Artificial Sequence
<220> FEATURE:
<223> OTHER INFORMATION: hT4-AAA VL

<400> SEQUENCE: 74

```
Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Tyr Ala Ala Ala Met Tyr Thr Phe Gly Gln Gly Thr Lys Val Glu Ile
            100                 105                 110

Lys Arg
```

<210> SEQ ID NO 75
<211> LENGTH: 114
<212> TYPE: PRT
<213> ORGANISM: Artificial Sequence
<220> FEATURE:
<223> OTHER INFORMATION: hT4-Y96A VL

<400> SEQUENCE: 75

```
Asp Leu Val Met Thr Gln Ser Pro Ser Ser Leu Ser Ala Ser Val Gly
1               5                   10                  15

Asp Arg Val Thr Ile Thr Cys Lys Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Tyr Tyr Tyr His Met Ala Thr Phe Gly Gln Gly Thr Lys Val Glu Ile
            100                 105                 110

Lys Arg
```

<210> SEQ ID NO 76
<211> LENGTH: 108
<212> TYPE: PRT
<213> ORGANISM: Artificial Sequence
<220> FEATURE:
<223> OTHER INFORMATION: hT4-01 VL

<400> SEQUENCE: 76

```
Asp Leu Val Met Thr Gln Ser Pro Ser Ser Leu Ser Ala Ser Val Gly
1               5                   10                  15

Asp Arg Val Thr Ile Thr Cys Lys Ala Ser Gln Gly Leu Ser Ser Tyr
            20                  25                  30

Leu Ala Trp Tyr Gln Gln Lys Pro Gly Lys Ala Pro Lys Leu Leu Ile
```

```
                35                  40                  45
Tyr Trp Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Tyr His Met Tyr
                 85                  90                  95

Thr Phe Gly Gln Gly Thr Lys Val Glu Ile Lys Arg
                100                 105

<210> SEQ ID NO 77
<211> LENGTH: 114
<212> TYPE: PRT
<213> ORGANISM: Artificial Sequence
<220> FEATURE:
<223> OTHER INFORMATION: hT4-02 VL

<400> SEQUENCE: 77

Asp Leu Val Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Tyr Ser
                 20                  25                  30

Ser Asn Asn Lys Asn Tyr Leu Ala Trp Tyr Gln Gln Lys Pro Gly Lys
             35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Tyr His Met Tyr Thr Phe Gly Gln Gly Thr Lys Val Glu Ile
                100                 105                 110

Lys Arg

<210> SEQ ID NO 78
<211> LENGTH: 114
<212> TYPE: PRT
<213> ORGANISM: Artificial Sequence
<220> FEATURE:
<223> OTHER INFORMATION: hT4-03 VL

<400> SEQUENCE: 78

Asp Leu Val Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Asp Ser
                 20                  25                  30

Asp Asp Gly Asn Thr Tyr Leu Ala Trp Tyr Gln Gln Lys Pro Gly Lys
             35                  40                  45

Ala Pro Lys Leu Leu Ile Tyr Trp Leu Ser Tyr Arg Ala Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Tyr His Met Tyr Thr Phe Gly Gln Gly Thr Lys Val Glu Ile
                100                 105                 110

Lys Arg
```

```
<210> SEQ ID NO 79
<211> LENGTH: 9
<212> TYPE: PRT
<213> ORGANISM: Artificial Sequence
<220> FEATURE:
<223> OTHER INFORMATION: VL-CDR3 of TMab4, TMab4-D1A and TMab4-D1E

<400> SEQUENCE: 79

Gln Gln Tyr Tyr Tyr His Met Tyr Thr
1               5

<210> SEQ ID NO 80
<211> LENGTH: 9
<212> TYPE: PRT
<213> ORGANISM: Artificial Sequence
<220> FEATURE:
<223> OTHER INFORMATION: VL-CDR3 of TMab4-M95A

<400> SEQUENCE: 80

Gln Gln Tyr Tyr Tyr His Ala Tyr Thr
1               5

<210> SEQ ID NO 81
<211> LENGTH: 9
<212> TYPE: PRT
<213> ORGANISM: Artificial Sequence
<220> FEATURE:
<223> OTHER INFORMATION: VL-CDR3 of TMab4-M95L and TMab4-3 D1E M95L

<400> SEQUENCE: 81

Gln Gln Tyr Tyr Tyr His Leu Tyr Thr
1               5

<210> SEQ ID NO 82
<211> LENGTH: 9
<212> TYPE: PRT
<213> ORGANISM: Artificial Sequence
<220> FEATURE:
<223> OTHER INFORMATION: VL-CDR3 of TMab4-Y91A

<400> SEQUENCE: 82

Gln Gln Ala Tyr Tyr His Met Tyr Thr
1               5

<210> SEQ ID NO 83
<211> LENGTH: 9
<212> TYPE: PRT
<213> ORGANISM: Artificial Sequence
<220> FEATURE:
<223> OTHER INFORMATION: VL-CDR3 of TMab4-Y92A

<400> SEQUENCE: 83

Gln Gln Tyr Ala Tyr His Met Tyr Thr
1               5

<210> SEQ ID NO 84
<211> LENGTH: 9
<212> TYPE: PRT
<213> ORGANISM: Artificial Sequence
<220> FEATURE:
<223> OTHER INFORMATION: VL-CDR3 of TMab4-Y93A

<400> SEQUENCE: 84

Gln Gln Tyr Tyr Ala His Met Tyr Thr
1               5
```

<210> SEQ ID NO 85
<211> LENGTH: 9
<212> TYPE: PRT
<213> ORGANISM: Artificial Sequence
<220> FEATURE:
<223> OTHER INFORMATION: VL-CDR3 of TMab4-H94A

<400> SEQUENCE: 85

Gln Gln Tyr Tyr Tyr Ala Met Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: VL-CDR3 of TMab4-AAA, CT01-AAA and CTWWW-AAA

<400> SEQUENCE: 86

Gln Gln Tyr Ala Ala Ala Met Tyr Thr
1               5

<210> SEQ ID NO 87
<211> LENGTH: 9
<212> TYPE: PRT
<213> ORGANISM: Artificial Sequence
<220> FEATURE:
<223> OTHER INFORMATION: VL-CDR3 of TMab4-Y96A

<400> SEQUENCE: 87

Gln Gln Tyr Tyr Tyr His Met Ala Thr
1               5

<210> SEQ ID NO 88
<211> LENGTH: 9
<212> TYPE: PRT
<213> ORGANISM: Artificial Sequence
<220> FEATURE:
<223> OTHER INFORMATION: VL-CDR3 of TMab4-RYR

<400> SEQUENCE: 88

Gln Gln Tyr Arg Tyr Arg Met Tyr Thr
1               5

<210> SEQ ID NO 89
<211> LENGTH: 9
<212> TYPE: PRT
<213> ORGANISM: Artificial Sequence
<220> FEATURE:
<223> OTHER INFORMATION: VL-CDR3 of TMab4-IYI

<400> SEQUENCE: 89

Gln Gln Tyr Ile Tyr Ile Met Tyr Thr
1               5

<210> SEQ ID NO 90
<211> LENGTH: 9
<212> TYPE: PRT
<213> ORGANISM: Artificial Sequence
<220> FEATURE:
<223> OTHER INFORMATION: VL-CDR3 of TMab4-GYG

<400> SEQUENCE: 90

Gln Gln Tyr Gly Tyr Gly Met Tyr Thr
1               5

<210> SEQ ID NO 91
<211> LENGTH: 9
<212> TYPE: PRT
<213> ORGANISM: Artificial Sequence
<220> FEATURE:
<223> OTHER INFORMATION: VL-CDR3 of TMab4-3 M95X
<220> FEATURE:
<221> NAME/KEY: misc_feature
<222> LOCATION: (7)..(7)
<223> OTHER INFORMATION: Xaa can be any naturally occurring amino acid

<400> SEQUENCE: 91

Gln Gln Tyr Trp Tyr Trp Xaa Tyr Thr
1               5

<210> SEQ ID NO 92
<211> LENGTH: 9
<212> TYPE: PRT
<213> ORGANISM: Artificial Sequence
<220> FEATURE:
<223> OTHER INFORMATION: VL-CDR3 of TMab4-3 Y91H

<400> SEQUENCE: 92

Gln Gln His Trp Tyr Trp Met Tyr Thr
1               5

<210> SEQ ID NO 93
<211> LENGTH: 9
<212> TYPE: PRT
<213> ORGANISM: Artificial Sequence
<220> FEATURE:
<223> OTHER INFORMATION: VL-CDR3 of TMab4-3 Y91D

<400> SEQUENCE: 93

Gln Gln Asp Trp Tyr Trp Met Tyr Thr
1               5

<210> SEQ ID NO 94
<211> LENGTH: 9
<212> TYPE: PRT
<213> ORGANISM: Artificial Sequence
<220> FEATURE:
<223> OTHER INFORMATION: VL-CDR3 of TMab4-3 L2E T97I

<400> SEQUENCE: 94

Gln Gln Tyr Trp Tyr Trp Met Tyr Ile
1               5

<210> SEQ ID NO 95
<211> LENGTH: 9
<212> TYPE: PRT
<213> ORGANISM: Artificial Sequence
<220> FEATURE:
<223> OTHER INFORMATION: VL-CDR3 of TMab4-3 L2E T90L

<400> SEQUENCE: 95

Gln Leu Tyr Trp Tyr Trp Met Tyr Thr
1               5

<210> SEQ ID NO 96
<211> LENGTH: 9
<212> TYPE: PRT
<213> ORGANISM: Artificial Sequence
<220> FEATURE:
<223> OTHER INFORMATION: VL-CDR3 of TMab4-3 Q90H M95A

<400> SEQUENCE: 96

Gln His Tyr Trp Tyr Trp Ala Tyr Thr

<210> SEQ ID NO 97
<211> LENGTH: 8
<212> TYPE: PRT
<213> ORGANISM: Artificial Sequence
<220> FEATURE:
<223> OTHER INFORMATION: VL-CDR3 of TMab4-3 L8-1

<400> SEQUENCE: 97

Gln Gln Tyr Trp Tyr Trp Met Thr
1               5

<210> SEQ ID NO 98
<211> LENGTH: 8
<212> TYPE: PRT
<213> ORGANISM: Artificial Sequence
<220> FEATURE:
<223> OTHER INFORMATION: VL-CDR3 of TMab4-3 L8-2

<400> SEQUENCE: 98

Gln Gln Trp Tyr Trp Met Pro Thr
1               5

<210> SEQ ID NO 99
<211> LENGTH: 10
<212> TYPE: PRT
<213> ORGANISM: Artificial Sequence
<220> FEATURE:
<223> OTHER INFORMATION: VL-CDR3 of TMab4-3 L10-1

<400> SEQUENCE: 99

Gln Gln Tyr Trp Tyr Trp Pro Met Tyr Thr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: VL-CDR3 of TMab4-3 L10-2

<400> SEQUENCE: 100

Gln Gln Tyr Trp Tyr Trp Tyr Met Tyr Thr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: VL-CDR3 of TMab4-3 L10-3

<400> SEQUENCE: 101

Gln Gln Tyr Trp Tyr Trp Tyr Met Tyr Thr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: VL-CDR3 of TMab4-3 L11-1

<400> SEQUENCE: 102

Gln Gln Tyr Trp Tyr Trp Leu Tyr Met Tyr Thr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: VL-CDR3 of TMab4-3 L11-2

<400> SEQUENCE: 103

Gln Gln Tyr Pro Trp Tyr Trp Pro Met Tyr Thr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: VH-CDR3 of CT, CT-3 and CT-WWW

<400> SEQUENCE: 104

Gly Ala Tyr Lys Arg Gly Tyr Ala Met Asp Tyr
1               5                   10

<210> SEQ ID NO 105
<211> LENGTH: 7
<212> TYPE: PRT
<213> ORGANISM: Artificial Sequence
<220> FEATURE:
<223> OTHER INFORMATION: VH-CDR3 of CT02

<400> SEQUENCE: 105

Gly Trp Tyr Trp Phe Asp Leu
1               5

<210> SEQ ID NO 106
<211> LENGTH: 8
<212> TYPE: PRT
<213> ORGANISM: Artificial Sequence
<220> FEATURE:
<223> OTHER INFORMATION: VH-CDR3 of CT03

<400> SEQUENCE: 106

Gly Trp Tyr Trp Gly Met Asp Leu
1               5

<210> SEQ ID NO 107
<211> LENGTH: 7
<212> TYPE: PRT
<213> ORGANISM: Artificial Sequence
<220> FEATURE:
<223> OTHER INFORMATION: VH-CDR3 of CT01-AAA L102x
<220> FEATURE:
<221> NAME/KEY: misc_feature
<222> LOCATION: (7)..(7)
<223> OTHER INFORMATION: Xaa can be any naturally occurring amino acid

<400> SEQUENCE: 107

Gly Trp Tyr Trp Met Asp Xaa
1               5

<210> SEQ ID NO 108
<211> LENGTH: 7
<212> TYPE: PRT
<213> ORGANISM: Artificial Sequence
<220> FEATURE:
<223> OTHER INFORMATION: VH-CDR3 of CTWWW-AAA

<400> SEQUENCE: 108

```
Gly Trp Trp Trp Met Asp Leu
1               5

<210> SEQ ID NO 109
<211> LENGTH: 13
<212> TYPE: PRT
<213> ORGANISM: Artificial Sequence
<220> FEATURE:
<223> OTHER INFORMATION: VH-CDR1 of CT10 VH

<400> SEQUENCE: 109

Ala Ala Ser Gly Phe Thr Phe Ser Asp Phe Ser Met Ser
1               5                  10

<210> SEQ ID NO 110
<211> LENGTH: 17
<212> TYPE: PRT
<213> ORGANISM: Artificial Sequence
<220> FEATURE:
<223> OTHER INFORMATION: VH-CDR2 of CT10 and CT11

<400> SEQUENCE: 110

Tyr Ile Ser Arg Thr Ser His Thr Thr Tyr Tyr Ala Asp Ser Val Lys
1               5                   10                  15

Gly

<210> SEQ ID NO 111
<211> LENGTH: 13
<212> TYPE: PRT
<213> ORGANISM: Artificial Sequence
<220> FEATURE:
<223> OTHER INFORMATION: VH-CDR1 of CT11 and CT12

<400> SEQUENCE: 111

Ala Ala Ser Gly Phe Thr Asp Asp Phe Ser Met Ser
1               5                   10

<210> SEQ ID NO 112
<211> LENGTH: 17
<212> TYPE: PRT
<213> ORGANISM: Artificial Sequence
<220> FEATURE:
<223> OTHER INFORMATION: VH-CDR2 of CT12

<400> SEQUENCE: 112

Tyr Ile Ser Arg Thr Ser His Thr Thr Asp Tyr Ala Asp Ser Val Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: VH-CDR1 of hT4-59, hT4-61 and hT4-62

<400> SEQUENCE: 113

Lys Ser Ser Gln Ser Leu Leu Asn Ser Arg Asp Gly Lys Asn Tyr Leu
1               5                   10                  15

Ala

<210> SEQ ID NO 114
<211> LENGTH: 7
<212> TYPE: PRT
```

```
<213> ORGANISM: Artificial Sequence
<220> FEATURE:
<223> OTHER INFORMATION: VH-CDR2 of hT4-59 and hT4-61

<400> SEQUENCE: 114

Trp Ala Ser Thr Arg Glu Ser
1               5

<210> SEQ ID NO 115
<211> LENGTH: 17
<212> TYPE: PRT
<213> ORGANISM: Artificial Sequence
<220> FEATURE:
<223> OTHER INFORMATION: VH-CDR1 of hT4-60 and hT4-63

<400> SEQUENCE: 115

Lys Ser Ser Gln Ser Asp Leu Asn Ser Arg Asp Gly Lys Asn Tyr Leu
1               5                   10                  15

Ala

<210> SEQ ID NO 116
<211> LENGTH: 7
<212> TYPE: PRT
<213> ORGANISM: Artificial Sequence
<220> FEATURE:
<223> OTHER INFORMATION: VH-CDR2 of hT4-61

<400> SEQUENCE: 116

Asp Ala Ser Thr Arg Glu Ser
1               5

<210> SEQ ID NO 117
<211> LENGTH: 7
<212> TYPE: PRT
<213> ORGANISM: Artificial Sequence
<220> FEATURE:
<223> OTHER INFORMATION: VH-CDR2 of hT4-62 and hT4-63

<400> SEQUENCE: 117

Asp Asp Ser Thr Arg Glu Ser
1               5

<210> SEQ ID NO 118
<211> LENGTH: 18
<212> TYPE: PRT
<213> ORGANISM: Artificial Sequence
<220> FEATURE:
<223> OTHER INFORMATION: VL-CDR1

<400> SEQUENCE: 118

Lys Ser Ser Gln Ser Leu Phe Asn Ser Arg Thr Arg Lys Asn Tyr Leu
1               5                   10                  15

Ala Trp

<210> SEQ ID NO 119
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 119

Trp Tyr Trp Met Asp Leu
1               5
```

```
<210> SEQ ID NO 120
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 120

Trp Tyr Trp Phe Asp Leu
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 121

Trp Trp Trp Met Asp Leu
1               5

<210> SEQ ID NO 122
<211> LENGTH: 9
<212> TYPE: PRT
<213> ORGANISM: Artificial Sequence
<220> FEATURE:
<223> OTHER INFORMATION: VL-CDR3 of CTWWW-WWW

<400> SEQUENCE: 122

Gln Gln Tyr Trp Trp Trp Met Thr Tyr
1               5
```

The invention claimed is:

1. A cytosol-penetrating antibody comprising a light chain variable region ("VL") and a heavy chain variable region ("VH"), wherein the VL comprises a sequence represented by the following formula: Z2-X1-X2-X3-Z1,
wherein Z2, X1, X2, X3, and Z1 are the $90^{th}$, $92^{nd}$, $93^{rd}$, $94^{th}$, and
$95^{th}$ amino acid of the VL as defined by the Kabat numbering system, respectively,
wherein X1-X2-X3 is an endosomal escape motif,
wherein each of X1 and X2 is selected from the group consisting of tryptophan (W), tyrosine (Y), histidine (H) and phenylalanine (F), and X3 is selected from the group consisting of tryptophan (W), tyrosine (Y), and phenylalanine (F),
wherein Z1 is selected from the group consisting of methionine (M), isoleucine (I), leucine (L), histidine (H), asparaginic acid (D), and glutamic acid (E),
wherein Z2 is selected from the group consisting of glutamine (Q), leucine (L), and histidine (H),
wherein the first amino acid of the VL is asparaginic acid (D) or glutamic acid (E), and
wherein the antibody exhibits an ability to escape from endosomes into the cytosol.

2. The cytosol-penetrating antibody of claim 1, wherein the endosomal escape motif X1-X2-X3 comprises a sequence selected from the group consisting of W—W—W, W—Y—W, and Y—W-W (where W is tryptophan, and Y is tyrosine).

3. The cytosol-penetrating antibody of claim 1, wherein the CDR3 of the light chain variable region comprises a sequence selected from the group consisting of SEQ ID NOS: 9, 10, 24 and 51.

4. The cytosol-penetrating antibody of claim 1, wherein the light chain variable region comprises a sequence selected from the group consisting of SEQ ID NOS: 2, 3, 13 to 23, 25 to 37, 50, and 60 to 64.

5. The cytosol-penetrating antibody of claim 1, wherein the antibody is an intact immunoglobulin G-format antibody.

6. A composition for delivering an active substance into cytosol, the composition comprising the cytosol-penetrating antibody according to claim 1 and the active substance.

7. The composition of claim 6, wherein the active substance is selected from the group consisting of peptides, proteins, toxins, antibodies, antibody fragments, RNAs, siRNAs, DNAs, small molecule drugs, nanoparticles, and liposomes.

8. A cytosol-penetrating antibody comprising a light chain variable region and a heavy chain variable region,
wherein the light chain variable region comprises a CDR1 of SEQ ID NO: 6 and a CDR2 of SEQ ID NO: 7;
wherein the heavy chain variable region comprises a CDR1 of SEQ ID NO: 43 and a CDR2 of SEQ ID NO: 44;
and the heavy variable chain region or the light chain variable region or both comprise a CDR3 comprising the sequence X1-X2-X3, wherein each of X1, X2 and X3, individually, is either tryptophan (W) or tyrosine (Y);
wherein X3 is the $94^{th}$ residue of the light chain variable region or the $98^{th}$ residue of the heavy chain variable region, as defined by the Kabat numbering system.

9. The cytosol-penetrating antibody of claim 8, wherein the heavy chain variable region comprises a CDR3 comprising the sequence X1-X2-X3, wherein each of X1, X2 and X3 is, individually, either tryptophan (W) or tyrosine (Y).

10. The cytosol-penetrating antibody of claim 8, wherein the light chain variable region comprises a CDR3 comprising the sequence X1-X2-X3, wherein each of X1, X2 and X3 is, individually, either tryptophan (W) or tyrosine (Y).

11. The cytosol-penetrating antibody of claim 9, wherein X1 and X3 are tryptophan (W) and X2 is tyrosine (Y).

12. The cytosol-penetrating antibody of claim 9, wherein X1, X2 and X3 are tryptophan (W).

13. The cytosol-penetrating antibody of claim 10, wherein X1 and X3 are tryptophan (W) and X2 is tyrosine (Y).

14. The cytosol-penetrating antibody of claim 10, wherein X1, X2 and X3 are tryptophan (W).

15. A cytosol-penetrating antibody comprising a VL and a VH, wherein the VH comprises a sequence represented by the following formula: X1-X2-X3-Z1,
wherein X1, X2, X3, and Z1 are the $96^{th}$, $97^{th}$, and $98^{th}$, residue of the VH, respectively,
wherein Z1 is the and $102^{nd}$ amino acid of the VH as defined by the Kabat numbering system and, respectively,
wherein X1-X2-X3 is an endosomal escape motif, and each of X1, X2, and X3 is selected from the group consisting of tryptophan (W), tyrosine (Y), histidine (H), and phenylalanine (F),
wherein Z1 is selected from the group consisting of methionine (M), isoleucine (I), leucine (L), histidine (H), asparaginic acid (D), and glutamic acid (E),
wherein the first amino acid of the VH is asparaginic acid (D) or glutamic acid (E); and
wherein the antibody exhibits an ability to escape from endosomes into the cytosol.

16. The cytosol-penetrating antibody of claim 15, wherein the endosomal escape motif X1-X2-X3 of the heavy chain variable region comprises a sequence selected from the group consisting of W—W—W, W—W—H, W—Y—W, Y—W—W, W—Y—H, and Y—W-H (where W is tryptophan, Y is tyrosine, and H is histidine).

17. The cytosol-penetrating antibody of claim 15, wherein the CDR3 of the heavy chain variable region comprises a sequence selected from the group consisting of SEQ ID NOS: 46 to 49, and 53.

18. The cytosol-penetrating antibody of claim 15, wherein the heavy chain variable region comprises a sequence selected from the group consisting of SEQ ID NOS: 39 to 42, 52, and 54 to 59.

19. The cytosol-penetrating antibody of claim 15, wherein the antibody is an intact immunoglobulin G-format antibody.

20. A composition for delivering an active substance into cytosol, the composition comprising the cytosol-penetrating antibody according to claim 15 and the active substance.

21. The composition of claim 20, wherein the active substance is selected from the group consisting of peptides, proteins, toxins, antibodies, antibody fragments, RNAs, siRNAs, DNAs, small molecule drugs, nanoparticles, and liposomes.

22. An antigen-binding fragment of the antibody of claim 15.

23. The cytosol-penetrating antibody of claim 15, wherein each of X1, X2 and X3, individually, is either tryptophan (W) or tyrosine (Y).

24. The cytosol-penetrating antibody of claim 15, wherein X1 and X3 are tryptophan (W) and X2 is tyrosine (Y).

25. The cytosol-penetrating antibody of claim 15, wherein X1, X2 and X3 are tryptophan (W).

26. A cytosol-penetrating antibody, comprising a VL and a VH, wherein the VH comprises a sequence represented by the following formula: X1-X2-X3-Z1,
wherein X1, X2, and X3 are contiguous,
wherein X1, X2, and X3 are the $96^{th}$, $97^{th}$, and $98^{th}$ amino acid of the VH as defined by the Kabat numbering system, respectively,
wherein two amino acids are present between X3 and Z1,
wherein X1-X2-X3-Z1 is a sequence selected from the group consisting of W—Y-W-M-D-L (SEQ ID NO: 119), W—Y—W—F-D-L (SEQ ID NO: 120), and W—W-W-M-D-L (SEQ ID NO: 121), wherein W is tryptophan, M is methionine, D is asparaginic acid, L is leucine, and F is phenylalanine;
wherein the first amino acid of the VH is asparaginic acid (D) or glutamic acid (E), and
wherein the antibody exhibits an ability to escape from endosomes into the cytosol.

27. The cytosol-penetrating antibody of claim 1, wherein the VH comprises a sequence represented by the following formula:
X1-X2-X3-Z1,
wherein X1, X2, and X3 and Z1 are the $96^{th}$, $97^{th}$, and $98^{th}$, and
$102^{nd}$ amino acid of the VH as defined by the Kabat numbering system respectively,
wherein X1-X2-X3 is an endosomal escape motif, and each of X1, X2, and X3 is selected from the group consisting of tryptophan (W), tyrosine (Y), histidine (H), and phenylalanine (F),
wherein Z1 is selected from the group consisting of methionine (M), isoleucine (I), leucine (L), histidine (H), asparaginic acid (D), and glutamic acid (E),
wherein the first amino acid of the VH is asparaginic acid (D) or glutamic acid (E); and
wherein the antibody exhibits an ability to escape from endosomes into the cytosol.

* * * * *